US009512057B2

(12) United States Patent
Hoppe et al.

(10) Patent No.: US 9,512,057 B2
(45) Date of Patent: Dec. 6, 2016

(54) 3-HYDROXYPROPIONIC ACID COMPOSITIONS

(71) Applicants: Cargill, Incorporated, Wayzata, MI (US); Dow Global Technologies LLC, Midland, MI (US)

(72) Inventors: Cindy Hoppe, Superior, CO (US); Sarah M. Hoyt, Boulder, CO (US); Robert Tengler, Longmont, CO (US); David DeCoster, Lyons, CO (US); Bradley Harkrader, New York, NY (US); Patrick H. Au-Yeung, Midland, MI (US); Sanjib Biswas, Midland, MI (US); Pedro R. Vargas, II, Midland, MI (US); Raymond P. Roach, Midland, MI (US); Timothy Charles Frank, Midland, MI (US)

(73) Assignees: Cargill, Incorporated, Wayzata, MI (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/213,616

(22) Filed: Mar. 14, 2014

(65) Prior Publication Data

US 2015/0057455 A1 Feb. 26, 2015

Related U.S. Application Data

(60) Provisional application No. 61/792,887, filed on Mar. 15, 2013.

(51) Int. Cl.
| | | |
|---|---|---|
| *C07C 59/01* | (2006.01) | |
| *B01D 1/06* | (2006.01) | |
| *B01D 1/22* | (2006.01) | |
| *B01D 5/00* | (2006.01) | |

(52) U.S. Cl.
CPC .............. *C07C 59/01* (2013.01); *B01D 1/065* (2013.01); *B01D 1/222* (2013.01); *B01D 5/006* (2013.01)

(58) Field of Classification Search
CPC ......... B01D 1/065; B01D 1/222; B01D 5/006; C07C 59/01
See application file for complete search history.

(56) References Cited

U.S. PATENT DOCUMENTS

| | | |
|---|---|---|
| 2,408,889 A | 10/1946 | Short |
| 2,464,768 A | 3/1949 | Redmon et al. |
| 2,469,701 A | 5/1949 | Redmon |
| 2,798,053 A | 7/1957 | Brown et al. |
| 3,904,685 A | 9/1975 | Shahidi et al. |
| 3,915,921 A | 10/1975 | Schlatzer, Jr. |
| 4,029,577 A | 6/1977 | Godlewski et al. |
| 4,268,641 A | 5/1981 | Koenig et al. |
| 4,301,266 A | 11/1981 | Muenster et al. |
| 4,303,468 A | 12/1981 | Laguilharre et al. |
| 4,431,547 A | 2/1984 | Dubin |
| 4,581,829 A | 4/1986 | Becker et al. |
| 4,666,983 A | 5/1987 | Tsubakimoto et al. |
| 4,685,915 A | 8/1987 | Hasse et al. |
| 4,708,997 A | 11/1987 | Stanley, Jr. et al. |
| 4,734,478 A | 3/1988 | Tsubakimoto et al. |
| 4,857,610 A | 8/1989 | Chmelir et al. |
| 4,952,505 A | 8/1990 | Cho |
| 4,985,518 A | 1/1991 | Alexander et al. |
| 5,009,653 A | 4/1991 | Osborn, III |
| 5,093,472 A | 3/1992 | Bresciani |
| 5,135,677 A | 8/1992 | Yamaguchi et al. |
| 5,145,906 A | 9/1992 | Chambers et al. |
| 5,180,798 A | 1/1993 | Nakamura et al. |
| 5,252,474 A | 10/1993 | Gewain et al. |
| 5,274,073 A | 12/1993 | Gruber et al. |
| 5,331,059 A | 7/1994 | Engelhardt et al. |
| 5,342,899 A | 8/1994 | Graham et al. |
| 5,350,799 A | 9/1994 | Woodrum et al. |
| 5,426,199 A | 6/1995 | Lundquist |
| 5,470,928 A | 11/1995 | Harwood et al. |
| 5,510,307 A | 4/1996 | Narayanan et al. |

(Continued)

FOREIGN PATENT DOCUMENTS

| | | |
|---|---|---|
| CN | 101573451 A | 11/2009 |
| EP | 1124789 B1 | 9/2004 |
| EP | 1036190 B1 | 5/2005 |
| EP | 1305439 B1 | 6/2006 |
| EP | 1124979 B1 | 8/2006 |
| EP | 1731604 A1 | 12/2006 |
| EP | 1105514 B1 | 2/2008 |
| EP | 1778840 B1 | 6/2008 |
| EP | 1975236 A2 | 10/2008 |
| EP | 1654212 B1 | 7/2009 |

(Continued)

OTHER PUBLICATIONS

English translation of JP2013-023481, Feb. 2013, pp. 1-24.*
U.S. Appl. No. 14/536,201, filed Nov. 7, 2014, Hoppe et al.
U.S. Appl. No. 14/536,295, filed Nov. 7, 2014, Lipscomb et al.
U.S. Appl. No. 14/552,199, filed Nov. 24, 2014, Lynch.
U.S. Appl. No. 14/575,927, filed Dec. 18, 2014, Lynch et al.
U.S. Appl. No. 14/341,223, filed Jul. 25, 2014, Lynch et al.
European search report and opinion dated Sep. 8, 2014 for EP Application No. 10819620.5.
International search report and written opinion dated Aug. 12, 2014 for PCT/US2014/029767.

(Continued)

*Primary Examiner* — Paul A Zucker
*Assistant Examiner* — Mark Luderer
(74) *Attorney, Agent, or Firm* — Howson & Howson LLP; Colleen M. Schaller

(57) ABSTRACT

Methods and systems for producing high purity 3-hydroxypropionic acid (3-HP) from an aqueous medium, such as a fermentation broth, are described. Aqueous 3-HP solution can be purified by flash evaporation wherein the 3-HP is vaporized at an elevated temperature without conversion to acrylic acid. This process can be integrated with downstream processes for producing other chemical and consumer products.

11 Claims, 22 Drawing Sheets

(56) References Cited

U.S. PATENT DOCUMENTS

| | | |
|---|---|---|
| 5,510,526 A | 4/1996 | Baniel et al. |
| 5,558,656 A | 9/1996 | Bergman |
| 5,723,639 A | 3/1998 | Datta et al. |
| 5,817,870 A | 10/1998 | Haas et al. |
| 5,827,255 A | 10/1998 | Crainic |
| 5,876,983 A | 3/1999 | Sugimoto et al. |
| 6,004,773 A | 12/1999 | Araki et al. |
| 6,013,494 A | 1/2000 | Nakamura et al. |
| 6,087,140 A | 7/2000 | Cameron et al. |
| 6,284,495 B1 | 9/2001 | Sato et al. |
| 6,297,319 B1 | 10/2001 | Nagasuna et al. |
| 6,472,188 B1 | 10/2002 | Lee et al. |
| 6,489,508 B1 | 12/2002 | Van Gansbeghe et al. |
| 6,534,679 B2 | 3/2003 | Eyal et al. |
| 6,623,944 B2 | 9/2003 | Rieping |
| 6,709,919 B2 | 3/2004 | Tu |
| 6,723,799 B2 | 4/2004 | Sun et al. |
| 6,852,517 B1 | 2/2005 | Suthers et al. |
| 6,960,455 B2 | 11/2005 | Livshits et al. |
| 7,090,008 B2 | 8/2006 | Read |
| 7,141,154 B2 | 11/2006 | Lin et al. |
| 7,153,663 B2 | 12/2006 | Payne et al. |
| 7,166,743 B2 | 1/2007 | Zhong et al. |
| 7,186,541 B2 | 3/2007 | Gokarn et al. |
| 7,186,856 B2 | 3/2007 | Meng et al. |
| 7,223,567 B2 | 5/2007 | Ka-Yiu et al. |
| 7,279,598 B2 | 10/2007 | Meng et al. |
| 7,285,406 B2 | 10/2007 | Payne et al. |
| 7,309,597 B2 | 12/2007 | Liao et al. |
| 7,326,557 B2 | 2/2008 | San et al. |
| 7,358,071 B2 | 4/2008 | Payne et al. |
| 7,393,676 B2 | 7/2008 | Gokarn et al. |
| 7,524,660 B2 | 4/2009 | Caimi et al. |
| 7,538,247 B2 | 5/2009 | Craciun et al. |
| 7,638,316 B2 | 12/2009 | Gokarn et al. |
| 7,678,869 B2 | 3/2010 | Matyjaszewski et al. |
| 7,687,661 B2 | 3/2010 | Lilga et al. |
| 7,826,975 B2 | 11/2010 | Maranas et al. |
| 7,833,761 B2 | 11/2010 | Terashita et al. |
| 7,943,362 B2 | 5/2011 | Frost |
| 8,048,624 B1 | 11/2011 | Lynch |
| 8,076,111 B2 | 12/2011 | Fukui et al. |
| 8,652,816 B2 | 2/2014 | Lynch |
| 8,883,464 B2 | 11/2014 | Lynch |
| 2002/0164729 A1 | 11/2002 | Skraly et al. |
| 2003/0101486 A1 | 5/2003 | Facciotti et al. |
| 2003/0191146 A1 | 10/2003 | Kabbash et al. |
| 2003/0211131 A1 | 11/2003 | Martin et al. |
| 2003/0233675 A1 | 12/2003 | Cao et al. |
| 2003/0235892 A1 | 12/2003 | Katz et al. |
| 2004/0009466 A1 | 1/2004 | Maranas et al. |
| 2004/0076982 A1 | 4/2004 | Gokarn et al. |
| 2004/0152159 A1 | 8/2004 | Causey et al. |
| 2004/0152174 A1 | 8/2004 | Cervin et al. |
| 2004/0209337 A1 | 10/2004 | Frost et al. |
| 2004/0210087 A1 | 10/2004 | Meng et al. |
| 2004/0214294 A1 | 10/2004 | Rieping |
| 2005/0054060 A1 | 3/2005 | Chateau et al. |
| 2005/0196758 A1 | 9/2005 | Rock et al. |
| 2005/0221466 A1 | 10/2005 | Liao et al. |
| 2005/0222458 A1 | 10/2005 | Craciun et al. |
| 2005/0233031 A1 | 10/2005 | Hughes |
| 2005/0239179 A1 | 10/2005 | Skraly et al. |
| 2005/0272135 A1 | 12/2005 | Datta et al. |
| 2005/0283029 A1 | 12/2005 | Meng et al. |
| 2006/0014977 A1 | 1/2006 | Miller et al. |
| 2006/0084098 A1 | 4/2006 | Gill et al. |
| 2007/0010708 A1 | 1/2007 | Ness |
| 2007/0015936 A1 | 1/2007 | Meng |
| 2007/0027342 A1 | 2/2007 | Meng et al. |
| 2007/0087403 A1 | 4/2007 | Bestel-Corre et al. |
| 2007/0107080 A1 | 5/2007 | Liao et al. |
| 2007/0148749 A1 | 6/2007 | Yasuda et al. |
| 2007/0184524 A1 | 8/2007 | Gokarn et al. |
| 2007/0219390 A1 | 9/2007 | Zacher et al. |
| 2007/0245431 A1 | 10/2007 | Metz et al. |
| 2008/0076167 A1 | 3/2008 | Gokarn et al. |
| 2008/0119626 A1 | 5/2008 | Fujimaru |
| 2008/0124785 A1 | 5/2008 | Liao et al. |
| 2008/0193989 A1 | 8/2008 | Verser et al. |
| 2008/0199926 A1 | 8/2008 | Burgard et al. |
| 2009/0017514 A1 | 1/2009 | Datta et al. |
| 2009/0023006 A1 | 1/2009 | Bub et al. |
| 2009/0031453 A1 | 1/2009 | Jessen et al. |
| 2009/0053783 A1 | 2/2009 | Gokarn et al. |
| 2009/0076297 A1 | 3/2009 | Bogan, Jr. et al. |
| 2009/0082286 A1 | 3/2009 | Huang et al. |
| 2009/0111151 A1 | 4/2009 | Julien et al. |
| 2009/0203097 A1 | 8/2009 | Flint et al. |
| 2009/0234146 A1 | 9/2009 | Cooney et al. |
| 2009/0291480 A1 | 11/2009 | Jessen et al. |
| 2009/0298144 A1 | 12/2009 | Tsobanakis et al. |
| 2009/0305369 A1 | 12/2009 | Donaldson et al. |
| 2009/0325248 A1* | 12/2009 | Marx .................. C12P 7/40 |
| | | 435/141 |
| 2010/0099910 A1 | 4/2010 | Meng et al. |
| 2010/0151536 A1 | 6/2010 | Baynes et al. |
| 2010/0210017 A1 | 8/2010 | Gill et al. |
| 2011/0089016 A1 | 4/2011 | Winkelaar et al. |
| 2011/0105791 A1 | 5/2011 | Kuppinger |
| 2011/0125118 A1 | 5/2011 | Lynch |
| 2011/0144377 A1 | 6/2011 | Eliot et al. |
| 2011/0183391 A1 | 7/2011 | Frost |
| 2011/0244575 A1 | 10/2011 | Lipscomb et al. |
| 2011/0275851 A1 | 11/2011 | Orjuela et al. |
| 2011/0306732 A1 | 12/2011 | Fujino et al. |
| 2012/0010372 A1 | 1/2012 | Fujino |
| 2012/0041232 A1 | 2/2012 | Lynch |
| 2012/0244586 A1 | 9/2012 | Gokarn et al. |
| 2012/0264902 A1 | 10/2012 | Lipscomb et al. |
| 2013/0071893 A1 | 3/2013 | Lynch et al. |
| 2013/0122541 A1 | 5/2013 | Lynch et al. |
| 2013/0189787 A1 | 7/2013 | Lynch |
| 2013/0345470 A1 | 12/2013 | Tengler et al. |
| 2014/0045231 A1 | 2/2014 | Lynch |
| 2014/0135526 A1 | 5/2014 | Lynch |
| 2014/0309451 A1 | 10/2014 | Tengler et al. |

FOREIGN PATENT DOCUMENTS

| | | |
|---|---|---|
| EP | 1975236 A3 | 9/2009 |
| EP | 1706457 B1 | 2/2012 |
| JP | H 09-505463 | 6/1997 |
| JP | 2013-023481 * | 2/2013 |
| WO | WO 98/21339 A1 | 5/1998 |
| WO | WO 98/55442 A1 | 12/1998 |
| WO | WO 00/56693 A1 | 9/2000 |
| WO | WO 01/16346 A1 | 3/2001 |
| WO | WO 01/38284 A1 | 5/2001 |
| WO | WO 02/34784 A2 | 5/2002 |
| WO | WO 02/42418 A2 | 5/2002 |
| WO | WO 03/040690 A2 | 5/2003 |
| WO | WO 02/042418 A3 | 6/2003 |
| WO | WO 03/062173 A2 | 7/2003 |
| WO | WO 03/082795 A2 | 10/2003 |
| WO | WO 2004/018621 A2 | 3/2004 |
| WO | WO 2004/033646 A2 | 4/2004 |
| WO | WO 2004/018621 A3 | 9/2004 |
| WO | WO 03/040690 A3 | 10/2004 |
| WO | WO 2005/003074 A1 | 1/2005 |
| WO | WO 2005/047498 A1 | 5/2005 |
| WO | WO 03/062173 A3 | 11/2005 |
| WO | WO 2005/105770 A2 | 11/2005 |
| WO | WO 2005/118719 A2 | 12/2005 |
| WO | WO 2005/105770 A3 | 3/2006 |
| WO | WO 2004/033646 A3 | 5/2006 |
| WO | WO 2005/118719 A3 | 9/2006 |
| WO | WO 2006/121755 A2 | 11/2006 |
| WO | WO 2007/012078 A1 | 1/2007 |
| WO | WO 2007/030830 A2 | 3/2007 |
| WO | WO 2007/047680 A2 | 4/2007 |
| WO | WO 2006/121755 A3 | 6/2007 |
| WO | WO 2007/030830 A3 | 10/2007 |
| WO | WO 2007/042494 A2 | 10/2007 |

(56) References Cited

FOREIGN PATENT DOCUMENTS

| | | |
|---|---|---|
| WO | WO 2007/042494 A3 | 11/2007 |
| WO | WO 2007/047680 A3 | 11/2007 |
| WO | WO 2008/027742 A1 | 3/2008 |
| WO | WO 2008/028002 A1 | 3/2008 |
| WO | WO 2008/089102 A2 | 7/2008 |
| WO | WO 2008/091627 A2 | 7/2008 |
| WO | WO 2008/145737 A1 | 12/2008 |
| WO | WO 2008/089102 A3 | 1/2009 |
| WO | WO 2009/031737 A1 | 3/2009 |
| WO | WO 2008/091627 A3 | 5/2009 |
| WO | WO 2009/062190 A2 | 5/2009 |
| WO | WO 2009/094485 A1 | 7/2009 |
| WO | WO 2009/062190 A3 | 9/2009 |
| WO | WO 2009/111513 A1 | 9/2009 |
| WO | WO 2009/155086 A2 | 12/2009 |
| WO | WO 2011/002892 A2 | 1/2011 |
| WO | WO 2011/038364 A1 | 3/2011 |
| WO | WO2011038364 * | 3/2011 |
| WO | WO 2011/063304 A1 | 5/2011 |
| WO | WO 2011/063363 A2 | 5/2011 |
| WO | WO 2011/063363 A3 | 8/2011 |
| WO | WO 2011/094457 A1 | 8/2011 |
| WO | WO 2012/054400 A1 | 4/2012 |
| WO | WO 2012/129450 A1 | 9/2012 |

OTHER PUBLICATIONS

Notice of allowance dated Jul. 11, 2014 for U.S. Appl. No. 13/498,468.
Office action dated Jul. 3, 2014 for U.S. Appl. No. 13/916,534.
Office action dated Jul. 10, 2014 for U.S. Appl. No. 12/891,790.
Office action dated Sep. 12, 2014 for U.S. Appl. No. 13/916,534.
Notice of allowance dated Nov. 21, 2014 for U.S. Appl. No. 13/916,534.
Office action dated Dec. 16, 2014 for U.S. Appl. No. 12/952,149.
Xu, Xiaowei. Fatty acid synthase inhibitors: research advances. Journal of international pharmaceutical research, 2009 vol. 36 (2): 105-108, 120. (English abstract).
U.S. Appl. No. 12/891,760, filed Sep. 27, 2010, Lynch.
U.S. Appl. No. 12/891,790, filed Sep. 27, 2010, Lynch.
U.S. Appl. No. 14/179,188, filed Feb. 12, 2014, Lipscomb.
U.S. Appl. No. 14/182,822, filed Feb. 18, 2014, Gill et al.
U.S. Appl. No. 14/213,605, filed Mar. 14, 2014, Hoppe et al.
U.S. Appl. No. 14/246,372, filed Apr. 7, 2014, Lynch et al.
U.S. Appl. No. 14/275,752, filed May 12, 2014, Lynch et al.
Agriculture Project Fact Sheet. U.S. Department of Energy, Office of Industrial Technologies. 2001. Chemicals From Lignocellulose, http://www.oit.doe.gov/agriculture/factsheets/lignocellulose.pdf (Apr. 21, 2004).
Alber, et al. Malonyl-coenzyme A reductase in the modified 3-hydroxypropionate cycle for autotrophic carbon fixation in archaeal *Metallosphaera* and *Sulfolobus* spp. J Bacteriol. Dec. 2006;188(24):8551-9.
Anton, et al. Sequencing and overexpression of the *Escherichia coli* aroE gene encoding shikimate dehydrogenase. Biochem J. Jan. 15, 1988;249(2):319-26.
Asano, et al. A new enzymatic method of acrylamide production. Agricultural and Biological Chemistry. 1982; 46(5):1183-1190.
Bailey, et al. Inverse metabolic engineering: A strategy for directed genetic engineering of useful phenotypes. BBiotechnol Bioeng. Sep. 5, 2002;79(5):568-79.
Bailey. Toward a science of metabolic engineering. Science. Jun. 21, 1991;252(5013):1668-75.
Barbin, et al. Induction of specific base-pair substitutions in *E. coli* trpA mutants by chloroethylene oxide, a carcinogenic vinyl chloride metabolite. Mutat Res. Nov.-Dec. 1985;152(2-3):147-56.
Bastian, et al. Engineered ketol-acid reductoisomerase and alcohol dehydrogenase enable anaerobic 2-methylpropan-1-ol production at theoretical yield in *Escherichia coli*. Metab Eng. May 2011;13(3):345-52.

Beguin et al. The biological degradation of cellulose. FEMS Microbiol Rev. Jan. 1994;13(1):25-58.
Bergler et al. Sequences of the envM gene and of two mutated alleles in *Escherichia coli*. J Gen Microbiol. Oct. 1992;138(10):2093-100.
Bergler, et al. The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA. Eur J Biochem. Dec. 15, 1996;242(3):689-94.
Bloch, et al. Control mechanisms in the synthesis of saturated fatty acids. Annu Rev Biochem. 1977;46:263-98.
Bonner, et al. A core catalytic domain of the TyrA protein family: arogenate dehydrogenase from Synechocystis. Biochem J. Aug. 15, 2004;382(Pt 1):279-91.
Brock, et al. Naturally occurring adenines within mRNA coding sequences affect ribosome binding and expression in *Escherichia coli*. J Bacteriol. Jan. 2007;189(2):501-10. Epub Nov. 3, 2006.
Broun, et al. Catalytic plasticity of fatty acid modification enzymes underlying chemical diversity of plant lipids. Science. Nov. 13, 1998;282(5392):1315-7.
Brown, et al. Synthesis of labeled acrylamide and N-methylolacrylamide (NMA) : 15N-acrylamide, 13C-NMA, 15N-NMA, and 13C,15N-NMA. Journal of labelled compounds & radiopharmaceuticals. 2005; 48(14):1031-1039.
Bunch, et al. The ldhA gene encoding the fermentative lactate dehydrogenase of *Escherichia coli*. Microbiology. Jan. 1997;143 (Pt 1):187-95.
Canada, et al. Directed evolution of toluene ortho-monooxygenase for enhanced 1-naphthol synthesis and chlorinated ethene degradation. J Bacteriol. Jan. 2002;184(2):344-9.
Chang, et al. Acetate metabolism in a pta mutant of *Escherichia coli* W3110: importance of maintaining acetyl coenzyme A flux for growth and survival. J Bacteriol. Nov. 1999;181(21):6656-63.
Chao, et al. Selective production of L-aspartic acid and L-phenylalanine by coupling reactions of aspartase and aminotransferase in *Escherichia coli*. Enzyme Microb Technol. Jul. 1, 2000;27(1-2):19-25.
Chica, et al. Semi-rational approaches to engineering enzyme activity: combining the benefits of directed evolution and rational design. Curr Opin Biotechnol. Aug. 2005;16(4):378-84.
Cho, et al. Simultaneous synthesis of enantiomerically pure (S)-amino acids and (R)-amines using coupled transaminase reactions. Biotechnol Bioeng. Mar. 30, 2003;81(7):783-9.
Chotani, et al. The commercial production of chemicals using pathway engineering. Biochim Biophys Acta. Dec. 29, 2000;1543(2):434-455.
Cleusix, et al Inhibitory activity spectrum of reuterin produced by Lactobacillus reuteri against intestinal bacteria. BMC Microbiol. Nov. 12, 2007;7:101.
Cowan, et al. Characterization of the major promoter for the plasmid-encoded sucrose genes scrY, scrA, and scrB. J Bacteriol. Dec. 1991;173(23):7464-70.
Crameri, et al. DNA shuffling of a family of genes from diverse species accelerates directed evolution . Nature. Jan. 15, 1998;391(6664):288-91.
Cronan, et al. Genetic and biochemical analyses of pantothenate biosynthesis in *Escherichia coli* and *Salmonella typhimurium*.J Bacteriol. Mar. 1982;149(3):916-22.
Cronan, J.E., Beta-Alanine Synthesis in *Escherichia coli* J Bacteriol. Mar. 1980;141(3):1291-7.
Cronk, et al. Cloning, crystallization and preliminary characterization of a beta-carbonic anhydrase from *Escherichia coli*. Acta Crystallogr D Biol Crystallogr. Sep. 2000;56(Pt 9):1176-9.
Daruwala, et al. Menaquinone (vitamin K2) biosynthesis: overexpression, purification, and characterization of a new isochorismate synthase from *Escherichia coli*. J. Bacteriol. May 1997;179(10):3133-8.
De Mendoza, et al Thermal regulation of membrane lipid fluidity in bacteria. Trends Biochem. Sci. 1983; 8:49-52.
Dell'Aquila, et al. Acid-base balance in peritoneal dialysis. J Nephrol. Mar.-Apr. 2006;19 Suppl 9:S104-7.

(56) References Cited

OTHER PUBLICATIONS

Den, et al. Enzymatic Conversion of β-Hydroxypropionate to Malonic Semialdehyde*. J Biol Chem Jul. 1959;234(7):1666-1671.
Devos, et al. Practical limits of function prediction. Proteins. Oct. 1, 2000;41(1):98-107.
Dewick, P. Chapter 4. The Shikimate Pathway: Aromatic Amino Acids and Phenylpropanoids. Medicinal Natural Products: A Biosynthetic Approach, Second Edition (2002): 121-166.
Diaz, et al. Characterization of the hca cluster encoding the dioxygenolytic pathway for initial catabolism of 3-phenylpropionic acid in *Escherichia coli* K-12. J Bacteriol. Jun. 1998;180(11):2915-23.
Dohr, et al. Engineering of a functional human NADH-dependent cytochrome P450 system. Proc Natl Acad Sci U S A. Jan. 2, 2001;98(1):81-6.
Drake, et al. Structure of the EntB multidomain nonribosomal peptide synthetase and functional analysis of its interaction with the EntE adenylation domain. Chem Biol. Apr. 2006;13(4):409-19.
Duncan, et al. Lactate-utilizing bacteria, isolated from human feces, that produce butyrate as a major fermentation product. Appl Environ Microbiol. Oct. 2004;70(10):5810-7.
Duncan, et al. The overexpression and complete amino acid sequence of *Escherichia coli* 3-dehydroquinase. Biochem J. Sep. 1, 1986;238(2):475-83.
Energetics Incorporated. 2003. Industrial Bioproducts: Today and Tomorrow. U.S. Department of Energy, Office of Energy Efficiency and Renewable Energy, Office of the Biomass Program, Washington, D.C.
Eppink, et al. Switch of coenzyme specificity of p-hydroxybenzoate hydroxylase. J Mol Biol. Sep. 10, 1999;292(1):87-96.
Epstein, et al. Oil: A Life Cycle Analysis of its Health and Environmental Impacts. The Center for Health and the Global Environment, Harvard Medical School. Mar. 2002. www.med.harvard.edu/chge/oil.html.
European search report and opinion dated Jul. 18, 2013 for EP Application No. 09801031.7.
European search report and opinion dated Sep. 23, 2013 for EP Application No. 10832342.9.
European search report dated Jan. 3, 2013 for Application No. 09813810.0.
European search report dated Jul. 2, 2010 for Application No. 08727619.2.
Farmer, et al. Improving lycopene production in *Escherichia coli* by engineering metabolic control. Nat Biotechnol. May 2000;18(5):533-7.
Fernando, et al. Biorefineries: current status, challenges and future direction Energ. Fuel. May 2006; 20:1727-1737.
Figge, et al. Methionine biosynthesis is *Escherichia coli* and *Corynebacterium glutamicum*. Microbiol Monogro. 2007; 5:163-193.
Fodor, et al. Light-Directed, Spatially Addressable Parallel Chemical Synthesis. Science. Feb. 15, 1991;251(4995):767-73.
Funa, et al. A novel quinone-forming monooxygenase family involved in modification of aromatic polyketides. J Biol Chem. Apr. 15, 2005;280(15):14514-23. Epub Feb. 8, 2005.
GenBank Accession No. AAC74497.1; Apr. 24, 2007. 2 pgs.
GenBank Accession No. NP 415816.1; available 1997.
GenBank Accession No. NP 415933.1; available 1997.
GenBank Accession No. NP 418045.4; available 1997.
GenBank Accession No. X81461 AF473544 (Sep. 7, 1994).
GenBank Accession No. AAS20429.1 (Jan. 19, 2004).
Giladi, et al. FolM, a new chromosomally encoded dihydrofolate reductase in *Escherichia coli*. J Bacteriol. Dec. 2003;185(23):7015-8.
Gill, et al. Genome-wide screening for trait conferring genes using DNA microarrays. Proc Natl Acad Sci U S A. May 14, 2002;99(10):7033-8. Epub May 7, 2002.
Ginkel, et al. Identification and cloning of the *Mycobacterium avium* folA gene, required for dihydrofolate reductase activity. FEMS Microbiol Left. Nov. 1, 1997;156(1):69-78.
Gokarn, et al. Metabolic analysis of *Escherichia coli* in the presence and absence of the carboxylating enzymes phosphoenolpyruvate carboxylase and pyruvate carboxylase. Appl Environ Microbiol. May 2000;66(5):1844-50.
Goodwin, et al. Purification and characterization of methylmalonate-semialdehyde dehydrogenase from rat liver. Identity to malonate-semialdehyde dehydrogenase. J Biol Chem. Sep. 5, 1989;264(25):14965-71.
Gray, et al. Monofunctional chorismate mutase from Bacillus subtilis: purification of the protein, molecular cloning of the gene, and overexpression of the gene product in *Escherichia coli*. Biochemistry. Jan. 16, 1990;29(2):376-83.
Gronenborn. Overproduction of phage lambda repressor under control of the lac promotor of *Escherichia coli*. Mol Gen Genet. Nov. 17, 1976;148(3):243-50.
Gulmezian, et al. Genetic evidence for an interaction of the UbiG O-methyltransferase with UbiX in *Escherichia coli* coenzyme Q biosynthesis. J Bacteriol. Sep. 2006;188(17):6435-9.
Hall, et al. Structure-function analysis of NADPH:nitrate reductase from Aspergillus nidulans: analysis of altered pyridine nucleotide specificity in vivo. Microbiology. Jun. 2000;146 ( Pt 6):1399-406.
Hatzimanikatis, et al. Exploring the diversity of complex metabolic networks. Bioinformatics. Apr. 15, 2005;21(8):1603-9. Epub Dec. 21, 2004.
He, et al. A T42M substitution in bacterial 5-enolpyruvylshikimate-3-phosphate synthase (EPSPS) generates enzymes with increased resistance to glyphosate. Biosci Biotechnol Biochem. Jun. 2003;67(6):1405-9.
Heath, et al. Enoyl-acyl carrier protein reductase (fabI) plays a determinant role in completing cycles of fatty acid elongation in *Escherichia coli*. J Biol Chem. Nov. 3, 1995;270(44):26538-42.
Henry, et al. Discovery of novel routes for the biosynthesis of industrial chemicals: 3-Hydroxypropanoate. Slides. AICHE Annual Meeting. Nov. 8, 2007. Salt Lake City, UT.
Herter, et al. Autotrophic $CO_2$ Fixation by *Chloroflexus aurantiacus*: Study of Glyoxylate Formation and Assimilation via the 3-Hydroxypropionate Cycle. J Bacteriol Jul. 2001;183(14):4305-4316.
Hondorp et al. Oxidation of cysteine 645 of cobalamin-independent methionine synthase causes a methionine limitation in *Escherichia coli*. J Bacteriol. May 2009;191(10):3407-10. Epub Mar. 13, 2009.
Hügler, et al. Malonyl-Coenzyme A Reductase from *Chloroflexus aurantiacus*, a Key Enzyme of the 3-Hydroxypropionate Cycle for Autotrophic $CO_2$ Fixation. J Bacteriol May 2002;184(9):2404-2410.
International search report and written opinion dated Nov. 22, 2013 for PCT/US2013/046888.
International search report and written report dated Jun. 3, 2011 for PCT Application No. US2010/057690.
International search report dated Feb. 3, 2011 for PCT Application No. US2010/050436.
International search report dated Jun. 4, 2010 for PCT Application No. US2009/51607.
International search report dated Jun. 16, 2011 for PCT Application No. US2011/022790.
International search report dated Dec. 5, 2008 for PCT Application No. US08/50921.
International search report dated Apr. 29, 2010 for PCT Application No. US2009/57058.
Ivanova, et al. Genome sequence of Bacillus cereus and comparative analysis with Bacillus anthracis. Nature. May 1, 2003;423(6935):87-91.
Jiang, et al. Cloning and Expression of aroG Gene of *E. coli* and Its Co-expression with pheA and tyrB Genes. Sheng Wu Hua Xue Yu Sheng Wu Wu Li Xue Bao (Shanghai). 1998;30(6):593-596. (In Chinese with English abstract).
Joike, et al. Amino acid substitutions affecting catalytic activity and subunit interactions of aminodeoxychorismate synthase in *E. coli*. Abstracts of the General Meeting of the American Society for Microbiology. 2002; 102:275-276, and 102nd General Meeting of the American Society for Microbiology; Salt Lake, UT, USA; May 19-23, 2002.

(56) References Cited

OTHER PUBLICATIONS

Kapol, et al. Purification and characterization of 2-oxoglutarate decarboxylase of Leuconostoc oenos. Journal of General Microbiology 136 (1990), 1497-1499.

Kern, et al. Engineering primary metabolic pathways of industrial micro-organisms. J Biotechnol. Mar. 30, 2007;129(1):6-29. Epub Dec. 2, 2006.

Kim et al. Extractive Recovery of Products from Fermentation Broths. Biotechnol. Bioprocess Eng., 1999; 4:1-11.

Kim, et al. The Rut pathway for pyrimidine degradation: novel chemistry and toxicity problems. J Bacteriol. Aug. 2010;192(16):4089-102. Epub Apr. 16, 2010.

Kim, et al. Dihydrolipoamide dehydrogenase mutation alters the NADH sensitivity of pyruvate dehydrogenase complex of *Escherichia coli* K-12. J Bacteriol. Jun. 2008;190(11):3851-8. Epub Mar. 28, 2008.

Kim, et al. Effect of overexpression of Actinobacillus succinogenes phosphoenolpyruvate carboxykinase on succinate production in *Escherichia coli*. Appl Environ Microbiol. Feb. 2004;70(2):1238-41.

Kimchi-Sarfaty, et al. A "silent" polymorphism in the MDR1 gene changes substrate specificity. Science. Jan. 26, 2007;315(5811):525-8. Epub Dec. 21, 2006.

Kisselev. Polypeptide release factors in prokaryotes and eukaryotes: same function, different structure. Structure. Jan. 2002;10(1):8-9.

Kizer, et al. Application of functional genomics to pathway optimization for increased isoprenoid production. Appl Environ Microbiol. May 2008;74(10):3229-41. doi: 10.1128/AEM.02750-07. Epub Mar. 14, 2008.

Kleerebezem, et al. The qmeA (ts) mutation of *Escherichia coli* is localized in the fabI gene, which encodes enoyl-ACP reductase. Res Microbiol. Oct. 1996;147(8):609-13.

Kozliak, et al. Expression of proteins encoded by the *Escherichia coli* cyn operon: carbon dioxide-enhanced degradation of carbonic anhydrase. J Bacteriol. Sep. 1994;176(18):5711-7.

Kozliak, et al. Role of bicarbonate/CO2 in the inhibition of *Escherichia coli* growth by cyanate. J Bacteriol. Jun. 1995;177(11):3213-9.

Kurcok, et al. Reactions of β-lactones with potassium alkoxides and their complexes with 18-crown-6 in aprotic solvents. Journal of Organic Chemistry. 1993; 58(16):4219-4220.

Kwon, et al. A physiology study of *Escherichia coli* overexpressing phosphoenolpyruvate carboxykinase. Biosci Biotechnol Biochem. Apr. 2008;72(4):1138-41.

Kwon, et al. Influence of Gluconeogenic Phosphoenolpyruvate Carboxykinase (PCK) Expression on Succinic Acid Fermentation in *Escherichia coli* Under High Bicarbonate Condition. Journal of Microbiology and Biotechnology. 2006; 16(9):1448-1452.

Langlois, et al. A new preparation of trifluoromethanesulfinate salts. Journal of Fluorine Chemistry. 2007; 128(7):851-856.

Lennen, et al. A process for microbial hydrocarbon synthesis: Overproduction of fatty acids in *Escherichia coli* and catalytic conversion to alkanes. Biotechnol Bioeng. Jun. 1, 2010;106(2):193-202.

Li, et al. Characterization of two temperature-inducible promoters newly isolated from B. subtilis. Biochem Biophys Res Commun. Jul. 13, 2007;358(4):1148-53. Epub May 22, 2007.

Li, et al. Effect of poxB gene knockout on metabolism in *Escherichia coli* based on growth characteristics and enzyme activities. World Journal of Microbiology and Biotechnology V 23(4). Apr. 2007. p. 573-580.

Liang, et al. Fe2(SO4)3•4H2O/concentrated H2SO4: an efficient catalyst for esterification. Journal of Chemical Research, Synopses. 2004; 3:226-227.

Lipscomb, et al. Poster—Understanding production of 3-Hydroxypropionic Acid (3-HP) in a genomic context. OPX Biotechnologies. Metabolic Engineering. Sep. 17, 2008.

Lutke-Eversloh, et al. Feedback inhibition of chorismate mutase/prephenate dehydrogenase (TyrA) of *Escherichia coli*: generation and characterization of tyrosine-insensitive mutants. Appl Environ Microbiol. Nov. 2005;71(11):7224-8.

Lynch, et al. SCALEs: multiscale analysis of library enrichment. Nat Methods. Jan. 2007;4(1):87-93.

Lynch, M. Rapid optimization of microorganisms for the cost superior production of chemicals & fuels. OPX Biotechnologies. Sep. 15, 2008.

Magnuson et al. Regulation of fatty acid biosynthesis in *Escherichia coli*. Microbiol Rev. Sep. 1993;57(3):522-42.

Martin, et al. Engineering a mevalonate pathway in *Escherichia coli* for production of terpenoids. Nat Biotechnol. Jul. 2003;21(7):796-802. Epub Jun. 1, 2003.

Mehta, et al. Aminotransferases: demonstration of homology and division into evolutionary subgroups. Eur J Biochem. Jun. 1, 1993;214(2):549-61.

Meng, et al. Nucleotide sequence of the *Escherichia coli* cad operon: a system for neutralization of low extracellular pH. J Bacteriol. Apr. 1992;174(8):2659-69.

Milton, et al. In vitro mutagenesis and overexpression of the *Escherichia coli* trpA gene and the partial characterization of the resultant tryptophan synthase mutant alpha-subunits. J Biol Chem. Dec. 15, 1986;261(35):16604-15.

Mohan, et al. Effect of process parameters on 3-hydroxypropionic acid production from glycerol using a recombinant *Escherichia coli*. Appl Microbiol Biotechnol. Sep. 2009;84(4):649-57. Abstract only.

Moreau. Diversion of the metabolic flux from pyruvate dehydrogenase to pyruvate oxidase decreases oxidative stress during glucose metabolism in nongrowing *Escherichia coli* cells incubated under aerobic, phosphate starvation conditions. J Bacteriol. Nov. 2004;186(21):7364-8.

Moreau. The lysine decarboxylase CadA protects *Escherichia coli* starved of phosphate against fermentation acids. J Bacteriol. Mar. 2007;189(6):2249-61. Epub Jan. 5, 2007.

Moureu, et al. Acide acrylique et ethers acryliques. Acides et ethers halogeno-propioniques. Annales de Chimie (Cachan, France); vol. <9> 15; (1921); p. 249 (in French with English abstract).

Moureu, et al. Acide acrylique et ethers acryliques. Acides et ethers halogeno-propioniques. Seances de l'Academie des Sciences; vol. 172; (1921); p. 1269 (in French with English abstract).

Muday, et al. The tyrosine repressor negatively regulates aroH expression in *Escherichia coli*. Bacteriol. Jun. 1991;173(12):3930-2.

Nackley, et al. Human catechol-O-methyltransferase haplotypes modulate protein expression by altering mRNA secondary structure. Science. Dec. 22, 2006;314(5807):1930-3.

NCBI Reference Sequence: NP_414657.1 (Jan. 16, 1997).
NCBI Reference Sequence: NP_415792.1 (Jan. 16, 1997).
NCBI Reference Sequence: NP_416366.1 (Jan. 16, 1997).
NCBI Reference Sequence: NP_418812.1 (Jan. 16, 1997).
NCBI Reference Sequence: YP_001277512.1 (Jun. 6, 2007).
NCBI Reference Sequence: YP_001433009.1 (Sep. 4, 2007).
NCBI Reference Sequence: YP_001636209.1 (Dec. 21, 2007).
NCBI Reference Sequence: YP_002462600.1 (Dec. 29, 2008).
NCBI Reference Sequence: ZP_01039179.1 (Jan. 16, 2006).
NCBI Reference Sequence: ZP_01626393.1 (Dec. 15, 2006).
NCBI Reference Sequence: ZP_04957196.1 (Sep. 15, 2008).
NCBI Reference Sequence: ZP_05125944.1 (Sep. 15, 2008).

Nexant, Inc. Chemsystems Perp Program, Acrylic Acid, 08/09-3, Jul. 2010.

Nichols, et al. Cloning and sequencing of *Escherichia coli* ubiC and purification of chorismate lyase. J Bacteriol. Aug. 1992;174(16):5309-16.

Office action dated Jan. 23, 2014 for U.S. Appl. No. 13/575,581.
Office action dated Feb. 7, 2014 for U.S. Appl. No. 12/891,790.
Office action dated Feb. 13, 2013 for U.S. Appl. No. 12/523,047.
Office action dated Feb. 13, 2014 for U.S. Appl. No. 13/062,917.
Office action dated Feb. 20, 2013 for U.S. Appl. No. 12/891,760.
Office action dated Mar. 3, 2014 for U.S. Appl. No. 13/498,468.
Office action dated Apr. 15, 2014 for U.S. Appl. No. 13/416,103.
Office action dated Apr. 29, 2011 for U.S. Appl. No. 12/328,588.
Office action dated Jun. 3, 2013 for U.S. Appl. No. 13/416,103.
Office action dated Jun. 5, 2013 for U.S. Appl. No. 13/284,337.
Office action dated Jun. 19, 2013 for U.S. Appl. No. 12/891,790.

(56) References Cited

OTHER PUBLICATIONS

Office action dated Jul. 4, 2011 for EP Applilcation No. 08727619.2.
Office action dated Jul. 11, 2012 for U.S. Appl. No. 13/055,138.
Office action dated Aug. 29, 2012 for Chinese Application No. 200980137400.4 (in Chinese with English translation).
Office action dated Sep. 17, 2010 for U.S. Appl. No. 12/328,588.
Office action dated Sep. 18, 2012 for U.S. Appl. No. 12/891,790.
Office action dated Sep. 19, 2012 for JP Application No. 2012-531103 (in Japanese with English translation).
Office action dated Sep. 19, 2013 for U.S. Appl. No. 13/055,138.
Office action dated Oct. 22, 2013 for U.S. Appl. No. 12/891,760.
Office action dated Oct. 23, 2013 for U.S. Appl. No. 12/523,047.
Office action dated Nov. 2, 2012 for U.S. Appl. No. 13/416,103.
Office action dated Nov. 27, 2012 for U.S. Appl. No. 13/284,337.
Office action dated Dec. 12, 2013 for U.S. Appl. No. 13/527,799.
Ohmiya, et al. Structure of cellulases and their applications. Biotechnol Genet Eng Rev. 1997;14:365-414.
Ohnishi, et al. A novel methodology employing *Corynebacterium glutamicum* genome information to generate a new L-lysine-producing mutant. Appl Microbiol Biotechnol. Feb. 2002;58(2):217-23.
Okamura et al. Unprecedented acetoacetyl-coenzyme A synthesizing enzyme of the thiolase superfamily involved in the mevalonate pathway. Proc Natl Acad Sci U S A. Jun. 22, 2010;107(25):11265-70. Epub Jun. 7, 2010.
Oliveira, et al. Cloning and overexpression in soluble form of functional shikimate kinase and 5-enolpyruvylshikimate 3-phosphate synthase enzymes from *Mycobacterium tuberculosis*. Protein Expr Purif. Aug. 2001;22(3):430-5.
Orjuela, et al. Presentation: Recovery of succinic acid from fermentative broth through esterification with ethanol. Department of Chemical Engineering and Materials Science. Michigan State University. East Lansing, Michigan 48824. Jun. 29, 2010.
Ozcelik et al. Metabolic engineering of aromatic group amino acid pathway in Bacillus subtilis for L-phenylalanine production. Chemical Engineering Science. 2004;59(22-23):5019-5026.
Parikh, et al. Directed evolution of RuBisCO hypermorphs through genetic selection in engineered *E. coli*. Protein Eng Des Sel. Mar. 2006;19(3):113-9. Epub Jan. 19, 2006.
Patnaik, et al. Genome shuffling of *Lactobacillus* for improved acid tolerance. Nat Biotechnol. Jul. 2002;20(7):707-12.
Pohl et al. A new perspective on thiamine catalysis. Curr Opin Biotechnol. Aug. 2004;15(4):335-42.
Ponce, et al. Cloning of the Two Pyruvate Kinase Isoenzyme StructuralGenes from *Escherichia coli*: the Relative Roles of These Enzymes in Pyruvate Biosynthesis. J Bacteriol. Oct. 1995;177(19):5719-22.
Popp, J. Sequence and overexpression of the menD gene from *Escherichia coli*. J Bacteriol. Aug. 1989;171(8):4349-54.
Prather, et al. De novo biosynthetic pathways: rational design of microbial chemical factories. Curr Opin Biotechnol. Oct. 2008;19(5):468-74. doi: 10.1016/j.copbio.2008.07.009. Epub Sep. 5, 2008.
Price-Carter, et al. Polyphosphate kinase protects *Salmonella enterica* from weak organic acid stress. Journal of Bacteriology. 2005; 187:3088-3099.
Raj, et al. Effect of process parameters on 3-hydroxypropionic acid production from glycerol using a recombinant *Escherichia coli*. Appl Microbiol Biotechnol. Sep. 2009;84(4):649-57. Epub Apr. 8, 2009.
Ramalinga, et al. A mild and efficient method for esterification and transesterification catalyzed by iodine. Tetrahedron Letters. 2002; 43(5):879-882.
Ramey, et al. Poster—Translation of genomics data into useful metabolic engineering strategies: construction of a 3-hydroxypropionic acid tolerant *E. coli*. 2010.
Ramilo, et al. Overexpression, purification, and characterization of tyrosine-sensitive 3-deoxy-D-arabino-heptulosonic acid 7-phosphate synthase from *Escherichia coli*. Protein Expr Purif. Mar. 1997;9(2):253-61.
Rathnasingh, et al. Development and evaluation of efficient recombinant *Escherichia coli* strains for the production of 3-hydroxypropionic acid from glycerol. Biotechnol Bioeng. Nov. 1, 2009;104(4):729-39. doi: 10.1002/bit.22429.
Ray et al. Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.
Ren, et al. Molecular Iodine in Ionic Liquid: A Green Catalytic System for Esterification and Transesterification. Synthetic Communications. 2010; 40(11):1670-1676.
Rodriguez, et al. Structure-cytoprotective activity relationship of simple molecules containing an alpha,beta-unsaturated carbonyl system. J Med Chem. Jun. 6, 1997;40(12):1827-34.
Roe, et al. Inhibition of *Escherichia coli* growth by acetic acid: a problem with methionine biosynthesis and homocysteine toxicity. Microbiology. Jul. 2002;148(Pt 7):2215-22.
Saier, et al. The catabolite repressor/activator (Cra) protein of enteric bacteria. J Bacteriol. Jun. 1996;178(12):3411-7.
Sauna, et al. Silent polymorphisms speak: how they affect pharmacogenomics and the treatment of cancer. Cancer Res. Oct. 15, 2007;67(20):9609-12.
Schmidt-Dannert, et al. Molecular breeding of carotenoid biosynthetic pathways. Nat Biotechnol. Jul. 2000;18(7):750-3.
Seffernick, et al. Melamine deaminase and atrazine chlorohydrolase: 98 percent identical but functionally different. J Bacteriol. Apr. 2001;183(8):2405-10.
Sen, et al. Developments in directed evolution for improving enzyme functions. Appl Biochem Biotechnol. Dec. 2007;143(3):212-23.
Service. Sugary Recipe Boosts Grow-Your-Own Plastics. Science. Jun. 30, 2006;312(5782):1861.
Singh, et al. Genes restoring redox balance in fermentation-deficient *E. coli* NZN111. Metab Eng. Nov. 2009;11(6):347-54. Epub Jul. 21, 2009.
Sousa, et al. The ARO4 gene of *Candida albicans* encodes a tyrosine-sensitive DAHP synthase: evolution, functional conservation and phenotype of Aro3p-, Aro4p-deficient mutants. Microbiology. May 2002;148(Pt 5):1291-303.
Stephanopoulos, et al. Network Rigidity and Metabolic Engineering in Metabolite Overproduction. Science. Jun. 21, 1991;252(5013):1675-81.
Stephanopoulos. Challenges in engineering microbes for biofuels production. Science. Feb. 9, 2007;315(5813):801-4.
Stim, et al. Nucleotide sequence of the adi gene, which encodes the biodegradative acid-induced arginine decarboxylase of *Escherichia coli*. J Bacteriol. Mar. 1993;175(5):1221-34.
Straathoff, et al. Feasibility of acrylic acid production by fermentation. Appl Microbiol Biotechnol. Jun. 2005;67(6):727-34.
Strauss, et al. Enzymes of a novel autotrophic CO2 fixation pathway in the phototrophic bacterium Chloroflexus aurantiacus, the 3-hydroxypropionate cycle. Eur J Biochem. Aug. 1, 1993;215(3):633-43.
Sun, et al. ZrOCl2 x 8H2O: an efficient, cheap and reusable catalyst for the esterification of acrylic acid and other carboxylic acids with equimolar amounts of alcohols. Molecules. Apr. 10, 2006;11(4):263-71.
Takamura, et al. Changes in the intracellular concentration of acetyl-CoA and malonyl-CoA in relation to the carbon and energy metabolism of *Escherichia coli* K12. J Gen Microbiol. Aug. 1988;134(8):2249-53.
Third party submission under 37 C.F.R Section 1.290 dated Sep. 17, 2012 against U.S. Appl. No. 13/284,337.
Tian, et al. *Mycobacterium tuberculosis* appears to lack an alpha-ketoglutarate dehydrogenase and encodes pyruvate dehydrogenase in widely separated genes. Mol Microbiol. Aug. 2005;57(3):859-68.
Tian, et al. Variant tricarboxylic acid cycle in *Mycobacterium tuberculosis*: Identification of alpha-ketoglutarate decarboxylase. Proc Natl Acad Sci U S A. Jul. 26, 2005;102(30):10670-5. Epub Jul. 18, 2005.
Tomar, A. Master Thesis. Production of Pyruvate by *Escherichia coli* Using Metabolic Engineering. The University of Georgia, May 2002, pp. 1-171.

(56) References Cited

OTHER PUBLICATIONS

Tunnicliff, et al. The inhibition by substrate analogues of gamma-aminobutyrate aminotransferase from mitochondria of different subcellular fractions of rat brain. Can J Biochem. Apr. 1977;55(4):479-84.
Turlin, et al. 3-phenylpropionate catabolism and the *Escherichia coli* oxidative stress response. Res Microbiol. Apr. 2005;156(3):312-21. Epub Jan. 27, 2005.
Vedantam, et al. Characterization of mutations contributing to sulfathiazole resistance in *Escherichia coli*. Antimicrob Agents Chemother. Jan. 1998;42(1):88-93.
Warnecke, et al. A genomics approach to improve the analysis and design of strain selections. Metab Eng. May-Jul. 2008;10(3-4):154-65.
Warnecke, et al. Engineering of Organic Acid Tolerance Genes in *E. coli* for Biorefinery Applications. 2006 AIChE Annual meeting in San Francisco, California, Nov. 12-17, 2006, https://aiche.confex.comlaiche/2006/techprogram/P67122.HTM.
Warnecke, et al. Identification of a 21 amino acid peptide conferring 3-hydroxypropionic acid stress-tolerance to *Escherichia coli*. Biotechnol Bioeng. May 2012;109(5):1347-52. doi: 10.1002/bit.24398. Epub Jan. 2, 2012.
Warnecke, et al. Organic acid toxicity, tolerance, and production in *Escherichia coli* biorefining applications. Microbial Cell Factories. 2005;4(25):1-8.
Warnecke, et al. Rapid dissection of a complex phenotype through genomic-scale mapping of fitness altering genes. Metab Eng. May 2010;12(3):241-50.
Wasewar, et al. Fermentation of Glucose to Lactic Acid Coupled with Reactive Extraction: A Review. Ind. Eng. Chem. Res. 2004; 43:5969-5982.
Waterson, et al. Enoyl coenzyme A hydratase (crotonase). Catalytic properties of crotonase and its possible regulatory role in fatty acid oxidation. J Biol Chem. Aug. 25, 1972;247(16):5258-65.
Welch, et al. Extensive mosaic structure revealed by the complete genome sequence of uropathogenic *Escherichia coli*. Proc Natl Acad Sci U S A. Dec. 24, 2002;99(26):17020-4. Epub Dec. 5, 2002.
Werpy, et al. Pacific Northwest National Laboratory. Top Value Added Chemicals From Biomass, vol. 1—Results of Screening for Potential candidates From Sugars and Synthesis Gas, U.S. Department of Energy, Aug. 2004.
Whisstock, et al. Prediction of protein function from protein sequence and structure. Q Rev Biophys. Aug. 2003;36(3):307-40.
White, et al. The overexpression, purification and complete amino acid sequence of chorismate synthase from *Escherichia coli* K12 and its comparison with the enzyme from Neurospora crassa. Biochem J. Apr. 15, 1988;251(2):313-22.
Wishart, et al. A single mutation converts a novel phosphotyrosine binding domain into a dual-specificity phosphatase. J Biol Chem. Nov. 10, 1995;270(45):26782-5.
Witkowski, et al. Conversion of a beta-ketoacyl synthase to a malonyl decarboxylase by replacement of the active-site cysteine with glutamine. Biochemistry. Sep. 7, 1999;38(36):11643-50.
Yee, et al. On the role of helix 0 of the tryptophan synthetase alpha chain of *Escherichia coli*. J Biol Chem. Jun. 21, 1996;271(25):14754-63.
Yoshida, et al. Identification of PhoB binding sites of the yibD and ytfK promoter regions in *Escherichia coli*. J Microbiol. Apr. 2011;49(2):285-9. Epub May 3, 2011.
Zha, et al. Improving cellular malonyl-CoA level in *Escherichia coli* via metabolic engineering. Metab Eng. May 2009;11(3):192-8. Epub Feb. 5, 2009.
Zhang, et al. Inhibiting bacterial fatty acid synthesis. J Biol Chem. Jun. 30, 2006;281(26):17541-4. Epub Apr. 28, 2006.
Zhao et al. Binding of two flaviolin substrate molecules, oxidative coupling, and crystal structure of Streptomyces coelicolor A3(2) cytochrome P450 158A2. J Biol Chem. Mar. 25, 2005;280(12):11599-607. Epub Jan. 19, 2005.
Zhou, et al. Interdomain communication between the thiolation and thioesterase domains of EntF explored by combinatorial mutagenesis and selection. Chem Biol. Aug. 2006;13(8):869-79.
European Search Report dated Sep. 2, 2016 issued in corresponding EP application No. 14763233.5.

\* cited by examiner

US 9,512,057 B2

3-HYDROXYPROPIONIC ACID COMPOSITIONS

CROSS-REFERENCE

This application claims the benefit of U.S. Provisional Application 61/792,887, filed on Mar. 15, 2013, which application is incorporated herein by reference in its entirety.

BACKGROUND

3-Hydroxypropionate ("3-HP", CAS No. 503-66-2) is a carboxylic acid that is a highly attractive chemical feedstock for the production of many large market commodity chemicals currently produced from petroleum derivatives. For example, commodity products that can be readily produced using 3-HP include acrylic acid (AA), 1,3-propanediol, methyl-acrylate, and acrylamide. The sum value of these commodity chemicals is currently estimated to exceed several billion dollars annually in the U.S. In addition, manufacture of the same commodities via the clean, cost-effective production of 3-HP from biomass will substitute renewable feedstocks for non-renewable resources.

Production of 3-HP is only one important part of the 3-HP procurement process. Another critical step in the process of 3-HP procurement is the purification of 3-HP, whether from a medium used for biological production (e.g., fermentation broth) or a medium used for chemical synthesis. Of particular interest is providing a process for the purification of 3-HP regardless of the form of the 3-HP, for example purification of 3-HP from a medium (such as a fermentation medium) where it exists in a salt form such as a sodium or calcium salt.

Purification of 3-HP is particularly challenging. 3-HP is very hydrophilic and, as a result, is very difficult to separate from water. Traditional distillation techniques to purify 3-HP are ineffective because 3-HP decomposes (e.g., dehydrates to acrylic acid) at elevated temperatures before it vaporizes.

A variety of other purification methods have been explored for the purification of carboxylic acids, primarily lactic acid. These purification methods, however, often employ organic solvents, solid adsorbents, reactive amines, and/or energy-intensive processes.

There remains a need for methods of purifying 3-HP that minimize the use of organic solvents, highly acidic solutions, and other chemicals.

SUMMARY

In some cases, this disclosure provides compositions comprising at least about 90% by weight of a biologically produced 3-HP. In some cases, the composition comprises at least about 95%, or at least about 98% by weight of a biologically produced 3-HP.

In some cases, a composition described in this disclosure has a $^{14}C$ concentration of at least 1 part per trillion carbon, or about 1.2 parts per trillion carbon.

In some cases, a composition described in this disclosure comprises less than about 10% by weight of acrylic acid. In some cases, the composition comprises less than about 5%, or less than about 1% by weight of acrylic acid.

In some cases, this disclosure provides downstream chemical product produced from the compositions purified as described herein. In some cases the downstream chemical product is selected from the group consisting of acrylic acid (AA), 1,3-propanediol, methyl acrylate, acrylamide, propiolactone, ethyl-3-3-HP, malonic acid, acrylonitrile, butyl acrylate, 3-HP amide, and ethyl acrylate.

In some cases, this disclosure provides consumer products produced using 3-HP or a downstream chemical product of 3-HP. In some cases, the consumer product comprises 3-HP or a downstream chemical product or 3-HP with a $^{14}C$ concentration of at least 1 part per trillion carbon.

In some cases, this disclosure provides a method of vaporizing 3-HP from a solution, comprising: (a) providing an aqueous solution of 3-HP; (b) heating the aqueous solution of 3-HP to a first temperature under a first pressure, thereby generating a heated aqueous solution of 3-HP; and (c) exposing the heated aqueous solution of 3-HP to a second temperature under a second pressure, thereby generating a vapor comprising 3-HP (e.g., a vapor comprising 3-HP, water, and possibly other volatile components).

In some cases, the second pressure is lower than the first pressure, thereby generating a pressure difference. In some cases, the first temperature is lower than the second temperature, thereby generating a temperature difference. In some cases, the first temperature is approximately the same as the second temperature.

In some cases, the heated aqueous solution of 3-HP is exposed to the second temperature for about 0.01 to about 1000 seconds. In some cases, the heated aqueous solution of 3-HP is exposed to the second temperature for less than about 300 seconds.

In some cases, the vapor comprising 3-HP is condensed, to generate a condensed 3-HP solution. In some cases, the condensing is performed in a first condenser. In some cases, the condensing is performed in a second condenser or further condenser. In some cases, the second condenser or further condenser may be used to condense vapor comprising 3-HP that does not condense in the first condenser or the second condenser. In some cases, the first condenser is operated at a temperature higher than the temperature of the second condenser.

In some cases, the condensed 3-HP solution is concentrated to generate a concentrated 3-HP solution. In some cases, the concentrated 3-HP solution comprises about 70% to about 80% by weight of 3-HP.

In some cases, the aqueous solution of 3-HP is concentrated prior to heating to the first temperature under the first pressure.

In some cases, the aqueous solution of 3-HP is clarified prior to heating to the first temperature under the first pressure. In some cases, the clarifying is performed by a method selected from the group consisting of filtration, centrifugation, and combinations thereof.

In some cases, substantially all the aqueous solution of 3-HP is maintained in a liquid state after heating the aqueous solution of 3-HP to the first temperature under the first pressure.

In some cases, the first temperature is at or below about 26° C. and the first pressure is at least about 0.03 bar, or the first temperature is at or below about 52° C. and the first pressure is at least about 0.14 bar, or the first temperature is at or below about 67° C. and the first pressure is at least about 0.28 bar, or the first temperature is at or below about 80° C. and the first pressure is at least about 0.48 bar, or the first temperature is at or below about 90° C. and the first pressure is at least about 0.69 bar, or the first temperature is at or below about 100° C. and the first pressure is at least about 1 bar, or the first temperature is at or below about 114° C. and the first pressure is at least about 1.7 bar, or the first temperature is at or below about 125° C. and the first pressure is at least about 2.3 bar, or the first temperature is at or below about 135° C. and the first pressure is at least about 3.2 bar, or the first temperature is at or below about 145° C. and the first pressure is at least about 4.1 bar, or the first temperature is at or below about 155° C. and the first pressure is at least about 5.4 bar, or the first temperature is at or below about 164° C. and the first pressure is at least about 6.9 bar, or the first temperature is at or below about 172° C. and the first pressure is at least about 8.3 bar, or the first temperature is at or below about 189° C. and the first pressure is at least about 12 bar, or the first temperature is at or below about 200° C. and the first pressure is at least about 16 bar, or the first temperature is at or below about 210° C. and the first pressure is at least about 19 bar.

In some cases, the pressure difference is sufficient to vaporize the heated aqueous solution of 3-HP at the second temperature. In some cases, the temperature difference is sufficient to vaporize the heated aqueous solution of 3-HP at the second pressure.

In some cases, the second temperature is about 170° C. to about 270° C., and the second pressure is about 1 mbar to about 200 mbar. In some cases, the pressure difference is about 0.5 bar to about 20 bar. In some cases, the pressure difference is about 0.5 bar to about 2 bar.

In some cases, less than about 20% of the 3-HP is converted to acrylic acid during purification. In some cases, less than about 10% of the 3-HP is converted to acrylic acid during purification. In some cases less than about 5% of the 3-HP is converted to acrylic acid during purification. In some cases less than about 1% of the 3-HP is converted to acrylic acid during purification.

In some cases, at least about 80% of 3-HP in the vapor comprising 3-HP is in a monomeric form. In some cases, at least about 90% of 3-HP in the vapor comprising 3-HP is in a monomeric form. In some cases, at least about 95% of 3-HP in the vapor comprising 3-HP is in a monomeric form.

In some cases, the concentrated 3-HP solution comprises 3-HP:acrylic acid in a molar ratio range of about 25 to about 200. In some cases, the concentrated 3-HP solution comprises 3-HP:acrylic acid at a molar ratio of about 100.

In some cases, the aqueous solution of 3-HP is a fermentation broth. In some cases, the aqueous solution of 3-HP is derived from a fermentation broth. In some cases, the 3-HP has been produced by a microorganism. In some cases, the 3-HP has been chemically synthesized.

In some cases, at least a portion of the 3-HP in the aqueous solution exists as an ammonium salt. In some cases, a substantial portion of the 3-HP in the aqueous solution exists as an ammonium salt. In some cases, at least about 60% of the 3-HP in the aqueous solution exists as an ammonium salt. In some cases, at least about 70% of the 3-HP in the aqueous solution exists as an ammonium salt. In some cases, at least about 80% of the 3-HP in the aqueous solution exists as an ammonium salt. In some cases, at least about 90% of the 3-HP in the aqueous solution exists as an ammonium salt.

In some cases, this disclosure provides a vapor comprising 3-HP produced according to any of the methods described herein. In some cases, this disclosure provides a condensed 3-HP solution produced according to any of the methods described herein. In some cases, this disclosure provides a concentrated 3-HP solution produced according to any of the methods described herein.

In some cases, this disclosure provides systems for purifying 3-HP, comprising: (a) a first vessel at a first temperature under a first pressure, wherein the first vessel is configured to receive an aqueous solution of 3-HP and to generate a heated aqueous solution of 3-HP; (b) a second vessel at a second temperature under a second pressure, wherein the second vessel is configured to convert at least a portion of the heated aqueous solution of 3-HP to a vapor comprising 3-HP; and (c) a first condenser, wherein the first condenser is configured to condense at least a portion of the vapor comprising 3-HP.

In some cases, the first temperature is in a range of about ambient temperature to about 240° C. In some cases, the second temperature is in a range of about 175° C. to about 280° C.

In some cases, the first temperature is lower than the second temperature, thereby generating a temperature difference. In some cases, the second pressure is lower than the first pressure, thereby generating a pressure difference.

In some cases, the temperature difference is in a range of about 20 to about 60° C. In some cases, the pressure difference is in a range of about 0.5 to about 20 bar.

In some cases, a system provided in this disclosure comprises a second condenser, or a further condenser. In some cases the first condenser is operated at a temperature higher than the temperature of the second condenser.

In some cases, the first temperature is at or below about 26° C. and the first pressure is at least about 0.03 bar, or the first temperature is at or below about 52° C. and the first pressure is at least about 0.14 bar, or the first temperature is at or below about 67° C. and the first pressure is at least about 0.28 bar, or the first temperature is at or below about 80° C. and the first pressure is at least about 0.48 bar, or the first temperature is at or below about 90° C. and the first pressure is at least about 0.69 bar, or the first temperature is at or below about 100° C. and the first pressure is at least about 1 bar, or the first temperature is at or below about 114° C. and the first pressure is at least about 1.7 bar, or the first temperature is at or below about 125° C. and the first pressure is at least about 2.3 bar, or the first temperature is at or below about 135° C. and the first pressure is at least about 3.2 bar, or the first temperature is at or below about 145° C. and the first pressure is at least about 4.1 bar, or the first temperature is at or below about 155° C. and the first pressure is at least about 5.4 bar, or the first temperature is at or below about 164° C. and the first pressure is at least about 6.9 bar, or the first temperature is at or below about 172° C. and the first pressure is at least about 8.3 bar, or the first temperature is at or below about 189° C. and the first pressure is at least about 12 bar, or the first temperature is at or below about 200° C. and the first pressure is at least about 16 bar, or the first temperature is at or below about 210° C. and the first pressure is at least about 19 bar.

In some cases, the temperature difference is sufficient to vaporize the heated aqueous solution of 3-HP at the second pressure. In some cases, the pressure difference is sufficient to vaporize the heated aqueous solution of 3-HP at the second temperature.

In some cases, the second temperature is about 170° C. to about 270° C., and the second pressure is about 1 mbar to about 200 mbar. In some cases, the pressure difference is about 0.5 bar to about 20 bar. In some cases, the pressure difference is about 0.5 bar to about 2 bar.

In some cases, this disclosure provides methods of producing a 3-HP solution, comprising: (a) providing an aqueous solution of 3-HP; (b) heating the aqueous solution of 3-HP to a first temperature under a first pressure, thereby generating a heated aqueous solution of 3-HP, wherein substantially all the heated aqueous solution of 3-HP is maintained in a liquid state; (c) exposing the heated aqueous solution of 3-HP to a second temperature under a second pressure, thereby generating a vapor comprising 3-HP (e.g., a vapor comprising 3HP, water, and possibly other volatile components), wherein: (1) the second pressure is lower than the first pressure, thereby generating a pressure difference, wherein the pressure difference is sufficient to vaporize the heated aqueous solution of 3-HP at the second temperature; and/or (2) the first temperature is lower than the second temperature, thereby generating a temperature difference, wherein the temperature difference is sufficient to vaporize the heated aqueous solution of 3-HP at the second pressure; (d) condensing the vapor comprising 3-HP to produce the 3-HP solution, wherein the first temperature is at or below about 26° C. and the first pressure is at least about 0.03 bar, or the first temperature is at or below about 52° C. and the first pressure is at least about 0.14 bar, or the first temperature is at or below about 67° C. and the first pressure is at least about 0.28 bar, or the first temperature is at or below about 80° C. and the first pressure is at least about 0.48 bar, or the first temperature is at or below about 90° C. and the first pressure is at least about 0.69 bar, or the first temperature is at or below about 100° C. and the first pressure is at least about 1 bar, or the first temperature is at or below about 114° C. and the first pressure is at least about 1.7 bar, or the first temperature is at or below about 125° C. and the first pressure is at least about 2.3 bar, or the first temperature is at or below about 135° C. and the first pressure is at least about 3.2 bar, or the first temperature is at or below about 145° C. and the first pressure is at least about 4.1 bar, or the first temperature is at or below about 155° C. and the first pressure is at least about 5.4 bar, or the first temperature is at or below about 164° C. and the first pressure is at least about 6.9 bar, or the first temperature is at or below about 172° C. and the first pressure is at least about 8.3 bar, or the first temperature is at or below about 189° C. and the first pressure is at least about 12 bar, or the first temperature is at or below about 200° C. and the first pressure is at least about 16 bar, or the first temperature is at or below about 210° C. and the first pressure is at least about 19 bar, and wherein the second temperature is about 170° C. to about 270° C., and the second pressure is about 1 mbar to about 200 mbar.

In some cases, the first temperature and the second temperature are different. In some cases, the first pressure and the second pressure are different. In some cases, the second pressure is lower than the second temperature and the first temperature is lower than the second temperature.

In some cases, this disclosure provides methods of decomposing ammonium 3-HP (A3-HP) to form 3-HP and ammonia by thermal salt splitting from an aqueous solution comprising A3-HP. In some cases, the method comprises: (a) providing an aqueous solution of A3-HP; (b) heating said aqueous solution of A3-HP in a device to an appropriate operating temperature and under an appropriate operating pressure; (c) generating 3-HP vapor, ammonia, and water vapor from the aqueous solution; (d) condensing the generated vapor in a first partial condenser operating at an appropriately high condensing temperature to selectively condense 3-HP vapor, and allowing uncondensed water and ammonia to leave the condenser at high temperature; and (e) condensing the water and ammonia in a second total condenser.

In some cases, the operating temperature during the method of thermal salt splitting is between 140 to 250° C. and preferably between 185 to 220° C. In some cases, the operating pressure is between 10 to 760 mmHg and preferably between 50 to 120 mmHg. In some cases, the first condenser is operated at a temperature higher than the second condenser. In some cases, the temperature of the first (partial) condenser is between 25 to 220° C. and preferably between 100 to 150° C. In some cases, the temperature of the second condenser is between 5 to 100° C. In some cases, the method further comprises using a third condenser, wherein water condenses in the second condenser, and ammonia condenses in the third condenser. In some cases, the second condenser is operated at a temperature higher than the third condenser. In some cases, the appropriate temperature for the third (total) condenser is between −87° C. and −33° C. In some cases, the aqueous solution of A3-HP may be from a fermentation broth, whole or purified, or concentrated in a device by removing water. In some cases, the 3-HP collected from the first condenser is immediately cooled to room temperature or below to minimize undesirable side reaction such as oligomer or amide formation. In some cases, multiple partial condensers operating at appropriate temperatures can be employed to separate any acrylic acid formed in the thermal salt splitting process.

In some cases, this disclosure provides a method of decomposing A3-HP to form 3-HP and ammonia by thermal salt splitting from an aqueous solution of A3-HP, comprising: (a) providing an aqueous solution of A3-HP; (b) heating said aqueous solution of A3-HP in a device to an appropriate operating temperature and under an appropriate operating pressure; and (c) generating 3-HP vapor, ammonia, and water vapor from the aqueous solution leaving other high boiling impurities behind;

In some cases, the operating temperature during the method of thermal salt splitting is between 140 to 250° C. and preferably between 170 to 220° C. In some cases, the operating pressure is between 10 to 760 mmHg and preferably between 50 to 120 mmHg. In some cases, the aqueous solution of A3-HP may be from a fermentation broth, whole or purified, or concentrated in a device by removing water.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

I. Definitions

Figure 1:
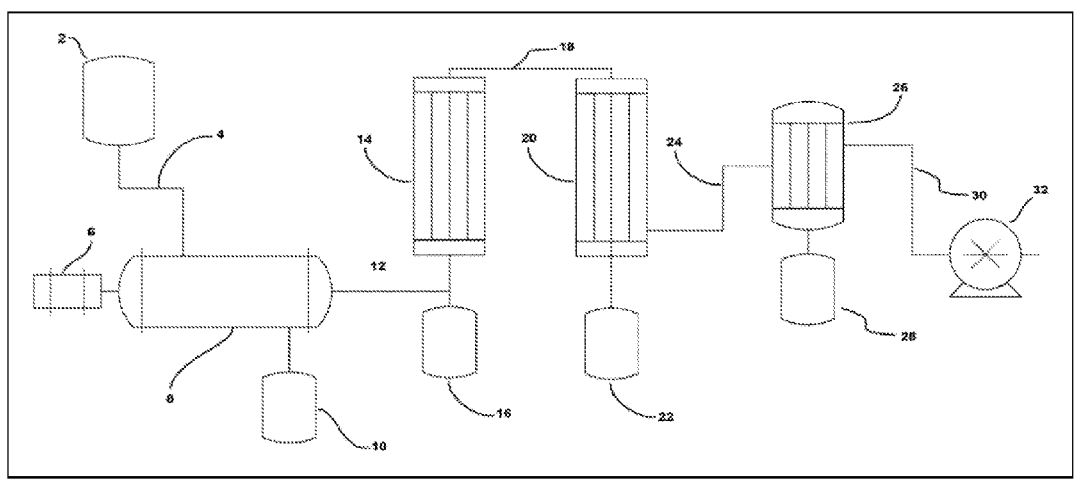
FIG. 1 illustrates an evaporation purification process that utilizes selective condensation.

As used herein, the singular forms "a," "an," and "the" are intended to include the plural forms as well, unless the context clearly indicates otherwise. Furthermore, to the extent that the terms "including," "includes," "having," "has," "with," "such as," or variants thereof, are used in either the specification and/or the claims, such terms are not limiting and are intended to be inclusive in a manner similar to the term "comprising".

"3-HP" means 3-hydroxypropionic acid (CAS number 503-66-2).

"AA" means acrylic acid (CAS number 79-10-7).

The term "flash evaporation" generally refers to a process by which a heated liquid stream encounters a sudden reduction in pressure. This results in rapid volatilization and cooling of the liquid, enabling separation of the volatile and non-volatile components of the liquid. When flash evaporation is performed on a fermentation medium, as in some embodiments described in this disclosure, higher boiling organic components, salts, and other non-volatile components of the medium will remain in the residual composition as either a liquid or solid, while water and volatile carboxylic acids evaporate overhead and are recovered by condensation.

The term "fermentation broth" generally refers to a mixture derived from a microbial fermentation process. A fermentation broth may be a mixture obtained from a microbial fermentation process without any purification or separation.

Alternatively, a fermentation broth may be a mixture obtained from a microbial fermentation procedure after purification or separation. A fermentation broth may be clarified. A fermentation broth may contain whole cells or may be substantially free of whole cells. Additionally, a fermentation broth may be treated, for example, with a lysing agent to release 3-HP from cells.

As used herein the term "about" refers to ±5%. For example, a value of "about 10" would include a range of 9.5 to 10.5. When the term "about" is used, the specified value is explicitly contemplated. For example, a value of "about 10" also includes a value of exactly 10.

The term "comprising" (and related terms such as "comprise" or "comprises" or "having" or "including") is not intended to exclude that other certain embodiments, for example an embodiment of any composition, method, or process, or the like, described herein, may "consist of" or "consist essentially of" the described features.

II. Overview

The present disclosure provides methods for purifying 3-HP from aqueous medium. Any suitable aqueous medium may be used. In some cases, an aqueous medium is a fermentation broth. The purified 3-HP may be stored or used directly to produce other downstream chemicals, for example, acrylamide, 1,3-propanediol, acrylic acid, 3-HP esters, 3-HP amide, and acrylic esters. A variety of industrial and consumer products can be further derived from 3-HP or chemical products produced from 3-HP.

The purification may involve heating an aqueous solution of 3-HP to a first temperature under a first pressure, and then exposing the heated aqueous solution of 3-HP to a second temperature under a second pressure. In some embodiments, the first temperature is lower than the second temperature. In some embodiments, the second pressure is lower than the first pressure. The temperature and/or pressure change may lead to vaporization of at least a portion of 3-HP and other volatile components, such as water and other organic acids. This vaporization may separate 3-HP from other non-volatile or less volatile components, for example, organic or inorganic salts, proteins, sugars, and lipids. Thereafter, the vapor comprising 3-HP may be condensed to produce a 3-HP solution. Such a 3-HP solution may be further concentrated to generate a concentrated 3-HP solution. The vapor comprising 3-HP, 3-HP solution, or concentrated 3-HP solution may be used in a dehydration reaction to produce, for example, acrylic acid. In a particular embodiment, the vapor comprising 3-HP is fed directly to a reactor, such as a dehydration reactor, to produce a downstream product, such as acrylic acid. Additionally, the purified 3-HP may be reacted with an alcohol, for example, a short chain alcohol, to produce a 3-HP ester.

In some embodiments, the aqueous 3-HP solution is produced by a fermentation process. A crude fermentation broth may be clarified (e.g., by filtration, precipitation, or centrifugation) to obtain a clarified fermentation broth prior to the purification. In some embodiments, addition of acids prior to or during the purification is not needed. In some embodiments, the pH of the clarified fermentation broth is in a range of about 4.5 to about 7.0, about 5.0 to about 6.5, or about 5.5 to about 6.0. In some embodiments, at least a portion of the 3-HP exists as an ammonium salt, and preferably a substantially amount of the 3-HP is in an ammonium salt form. Utilizing the 3-HP ammonium salt in the purification method of the present invention provides multiple cost advantages, including allowing for recycling of ammonia to fermentation, eliminating the cost to add acid prior to and/or during the purification, avoiding the need to utilize equipment fabricated from costly acid-resistant metals that will not degrade in acidic conditions, and the minimization of byproducts (e.g., ammonium salts) that would require additional processing to remove and additional cost for disposal. In some cases, 3-HP may exist as at least about 60%, at least about 70%, at least about 80%, at least about 90%, or at least about 95% ammonium salt.

The methods described herein may allow the purification of 3-HP with very low conversion to acrylic acid. In some embodiment, less than about 20%, less than about 15%, less than about 10%, less than about 9%, less than about 8%, less than about 7%, less than about 6%, less than about 5%, less than about 4%, less than about 3%, less than about 2%, or less than about 1% of 3-HP is converted to acrylic acid. The low conversion may be due to short residence time of the 3-HP at a high temperature (e.g., 120° C. or higher). In some embodiments, the residence time of 3-HP at high temperature (e.g., the amount of time the 3-HP liquid is in contact with the high temperature surface of the evaporator) is less than about 0.01, less than about 0.1, less than about 1, less than about 2, less than about 5, less than about 10, less than about 20, less than about 50, less than about 80, less than about 100, less than about 500 seconds, less than about 600 seconds, less than about 700 seconds, less than about 800 seconds, or less than about 1000 seconds.

III. Purification of 3-HP

With only 3 carbons, a carboxyl group and a hydroxyl group, 3-HP is highly hydrophilic and very difficult to separate from an aqueous medium. Traditional organic acid isolation approaches often rely on a biphasic liquid-liquid extraction process to isolate the acid. However, the extraction efficiency of 3-HP from water with an organic solvent is usually low. For example, U.S. Pat. No. 7,279,598 describes a process for separating and recovering 3-HP from acrylic acid using counter current extraction of the aqueous solution with ethyl acetate. After extraction, the remaining aqueous acid comprises 3-HP.

Purification of 3-HP at an elevated temperature is considered difficult. 3-HP is known to dehydrate to give acrylic acid at elevated temperatures (e.g., greater than 217° C.). In addition, carboxylic acids such as 3-HP generally exist in an equilibrium between the acid form and the deprotonated (salt) form in an aqueous solution. It is generally believed that the acid form is volatile while the salt form is not. Therefore, to distill an organic acid from an aqueous solution, a strong acid, for example hydrochloric acid or sulfuric acid, is routinely added to shift the equilibrium to the acid form.

Applicants have discovered that 3-HP can be purified from an aqueous solution by heating the bulk solution and then vaporizing it under a vacuum at an elevated temperature. Furthermore, the pH of the aqueous solution can be between about 0 to about 8, and preferably is greater than 4.5, which is above the pKa of 3-HP. Utilizing a pH of greater than 4.5 avoids or minimizes the need to use acid-resistant equipment and harmful chemicals for 3-HP purification.

The aqueous solution of 3-HP may have a pH in the range of about 4.5 to about 7.5, about 5.0 to about 7.0, or about 5.5. to about 6.5. In some cases, the aqueous solution of 3-HP may have a pH in the range of about 4.5 to about 5.0, about 5.0 to about 5.5, about 5.5 to about 6.5, about 6.5 to about 7.0, or about 7.0 to about 7.5. In some cases, the aqueous solution of 3-HP may have a pH of at least about 4.5, at least about 5.0, at least about 5.5, at least about 6.0, at least about 6.5, at least about 7.0, or at least about 7.5. In some cases, the aqueous solution of 3-HP may have a pH of less than about 7.5, less than about 7.0, less than about 6.5, less than about 6.0, less than about 5.5, less than about 5.0, or less than about 4.5.

In one embodiment, the aqueous solution has a pH of about 6.5. In another embodiment, the aqueous solution has a pH of about 4.5. The aqueous solution may be a fermentation broth comprising, for example, water, 3-HP, ammonia, lipids, sugars, proteins and other organic or inorganic additives necessary for fermentation. At a pH of about 4.5 and higher, a substantial amount of 3-HP may exists as an ammonium salt. Applicants unexpectedly discovered that the ammonium salt of 3-HP can be substantially vaporized to provide free 3-HP, thus reducing or eliminating the need for an acidification step or the addition of solvents or reactive amines. Furthermore, using a 3-HP solution in the pH range of about 4.5 to about 7.5 may substantially reduce the acid catalyzed dehydration reaction that produces acrylic acid, thereby producing 3-HP with high purity.

The concentration of 3-HP in the aqueous solution is not particularly limited, and any suitable concentration may be used. For example, the concentration may be in a range of about 30 to about 50 g/L, about 50 to about 100 g/L, or about 100 to about 500 g/L. The concentration of 3-HP may be about 30, about 50, about 100, about 200, about 300, about 400, about 500, or about 850 g/L. The concentration of 3-HP may be at least about 30, at least about 50, at least about 100, at least about 200, at least about 300, at least about 400, at least about 500, or at least about 850 g/L. The concentration of 3-HP may be at less than about 30, less than about 50, less than about 100, less than about 200, less than about 300, less than about 400, less than about 500, or less than about 850 g/L.

In some cases, the purification may be carried out by first providing a solution of 3-HP in a first vessel at a first temperature under a first pressure and then transferring the bulk solution to a second vessel at a second temperature under a second pressure, and then transferring vapor from the second vessel to a third vessel in which the 3-HP is condensed out of the vapor.

The first temperature may be in a range of about 20 to about 200° C., about 60 to about 150° C., or about 75 to about 100° C. The first temperature may be about ambient temperature, about 80, about 120, about 125, about 130, about 135, about 140, about 145, about 150, about 155, about 160, about 165, about 170, about 175, about 180, about 185, about 190, about 195, or about 200° C. The first temperature may be at least about ambient temperature, at least about 80, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, or at least about 200° C. The first temperature may be less than about ambient temperature, less than about 80, less than about 120, less than about 125, less than about 130, less than about 135, less than about 140, less than about 145, less than about 150, less than about 155, less than about 160, less than about 165, less than about 170, less than about 175, less than about 180, less than about 185, less than about 190, less than about 195, or less than about 200° C.

The first pressure may be in a range of about 5 to about 100 psi. The first pressure may be about 5, about 10, about 15, about 20, about 25, about 30, about 35, about 40, about 45, about 50, about 55, about 60, about 65, about 70, about 75, about 80, about 85, about 90, about 95, or about 100 psi. The first pressure may be at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 psi. The first pressure may be less than about 5, less than about 10, less than about 15, less than about 20, less than about 25, less than about 30, less than about 35, less than about 40, less than about 45, less than about 50, less than about 55, less than about 60, less than about 65, less than about 70, less than about 75, less than about 80, less than about 85, less than about 90, less than about 95, or less than about 100 psi.

In a particular embodiment, the first temperature is about 150° C. and the first pressure is about 75 psi. In an alternative embodiment, the first temperature is about 80° C. and the first pressure is about 20 psi.

In some embodiments, the second temperature is the same or higher than the first temperature. The second temperature may be in a range of about 170° C. to about 280° C., about 190° C. to about 260° C., or about 210° C. to about 240° C. The second temperature may be about 170, about 175, about 180, about 185, about 190, about 195, about 200, about 205, about 210, about 215, about 220, about 225, about 230, about 235, about 240, about 245, about 250, about 255, about 260, about 265, or about 270° C. The second temperature may be at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, at least about 250, at least about 255, at least about 260, at least about 265, or at least about 270° C. The second temperature may be less than about 170, less than about 175, less than about 180, less than about 185, less than about 190, less than about 195, less than about 200, less than about 205, less than about 210, less than about 215, less than about 220, less than about 225, less than about 230, less than about 235, less than about 240, less than about 245, less than about 250, less than about 255, less than about 260, less than about 265, or less than about 270° C.

In some embodiments, the second pressure is in a range of about 1 to about 200 mbar, about 10 to about 180 mbar, or about 20 to about 160 mbar. The second pressure may be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 60, about 65, about 70, about 75, about 80, about 85, about 90, about 95, about 100, about 110, about 120, about 130, about 140, about 150, about 160, about 170, about 180, about 190, or about 200 mbar. The second pressure may be at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 60, at least about 65, at least about 70, at least about 75, at least about 80, at least about 85, at least about 90, at least about 95, at least about 100, at least about 110, at least about 120, at least about 130, at least about 140, at least about 150, at least about 160, at least about 170, at least about 180, at least about 190, or at least about 200 mbar. The second pressure may be less than about 1, less than about 2, less than about 3, less than about 4, less than about 5, less than about 6, less than about 7, less than about 8, less than about 9, less than about 10, less than about 11, less than about 12, less than about 13, less than about 14, less than about 15, less than about 16, less than about 17, less than about 18, less than about 19, less than about 20, less than about 21, less than about 22, less than about 23, less than about 24, less than about 25, less than about 26, less than about 27, less than about 28, less than about 29, less than about 30, less than about 31, less than about 32, less than about 33, less than about 34, less than about 35, less than about 36, less than about 37, less than about 38, less than about 39, less than about 40, less than about 41, less than about 42, less than about 43, less than about 44, less than about 45, less than about 46, less than about 47, less than about 48, less than about 49, less than about 50, less than about 51, less than about 52, less than about 53, less than about 54, less than about 55, less than about 60, less than about 65, less than about 70, less than about 75, less than about 80, less than about 85, less than about 90, less than about 95, less than about 100, less than about 110, less than about 120, less than about 130, less than about 140, less than about 150, less than about 160, less than about 170, less than about 180, less than about 190, or less than about 200 mbar.

In some embodiments, the second temperature is higher than the first temperature and the second pressure is lower than the first pressure. The difference between the first and second temperature may be in a range of about 5 to about 100° C., about 10 to about 90° C., or about 20 to about 80° C. The difference between the first and second temperature may be about 5, about 10, about 15, about 20, about 25, about 30, about 35, about 40, about 45, about 50, about 55, about 60, about 65, about 70, about 75, about 80, about 85, or about 90° C. The difference between the first and second temperature may be at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, or at least about 90° C. The difference between the first and second temperature may be less about 5, less than about 10, less than about 15, less than about 20, less than about 25, less than about 30, less than about 35, less than about 40, less than about 45, less than about 50, less than about 55, less than about 60, less than about 65, less than about 70, less than about 75, less than about 80, less than about 85, or less than about 90° C.

The difference between the first and second pressure may be in a range of about 0.5 bar to about 20 bar, about 1 bar to about 10 bar, about 1 bar to about 5 bar, or about 0.5 bar to 2 bar. The difference between the first and second pressure may be about 1, about 2, about 3, about 4, about 5, about 6, about 7, about 8, about 9, about 10, about 11, about 12, about 13, about 14, about 15, about 16, about 17, about 18, about 19, or about 20 bar. The difference between the first and second pressure may be at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 bar. The difference between the first and second pressure may be less than about 1, less than about 2, less than about 3, less than about 4, less than about 5, less than about 6, less than about 7, less than about 8, less than about 9, less than about 10, less than about 11, less than about 12, less than about 13, less than about 14, less than about 15, less than about 16, less than about 17, less than about 18, less than about 19, or less than about 20 bar.

The third vessel may be a heat exchanger or column in which the condensation of 3-HP takes place. The vapor from the second vessel is cooled in the third vessel to a temperature in a range of about 30° C. to about 220° C., about 40° C. to about 160° C., or about 50° C. to about 100° C. The temperature of the third vessel may be about 30, about 50, about 70, about 90, about 110, about 130, about 150, about 170, about 190, about 210, or about 220° C. The temperature of the third vessel may be at least about 30, at least about 50, at least about 70, at least about 90, at least about 110, at least about 130, at least about 150, at least about 170, at least about 190, at least about 210, or at least about 220° C. The temperature of the third vessel may be less than about 30, less than about 50, less than about 70, less than about 90, less than about 110, less than about 130, less than about 150, less than about 170, less than about 190, less than about 210, or less than about 220° C.

The pressure in the third vessel may be about 1 mbar to about 1000 mbar, about 10 mbar to about 500 mbar, or about 50 mbar to about 100 mbar. The pressure in the third vessel may be may be about 1, about 10, about 50, about 100, about 150, about 200, about 250, about 300, about 350, about 400, about 450, about 500, about 550, about 600, about 650, about 700, about 750, about 800, about 850, about 900, about 950, or about 1000 mbar. The pressure in the third vessel may be may be at least about 1, about 10, about 50, about 100, about 150, about 200, about 250, about 300, about 350, about 400, about 450, about 500, about 550, about 600, about 650, about 700, about 750, about 800, about 850, about 900, about 950, or about 1000 mbar. The pressure in the third vessel may be may be at least about 1, at least about 10, at least about 50, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, or at least about 1000 mbar. The pressure in the third vessel may be may be less than about 1, less than about 10, less than about 50, less than about 100, less than about 150, less than about 200, less than about 250, less than about 300, less than about 350, less than about 400, less than about 450, less than about 500, less than about 550, less than about 600, less than about 650, less than about 700, less than about 750, less than about 800, less than about 850, less than about 900, less than about 950, or less than about 1000 mbar.

The transfer of an aqueous solution from the first vessel to the second vessel may be controlled by a metering pump or by a valve, for example a needle valve. The aqueous solution of 3-HP may be moved through the needle valve by a pressure difference between two vessels.

The residence at the second temperature time may be important for limiting the dehydration of 3-HP to acrylic acid (AA). In some embodiments, a short residence time may be used to minimize dehydration of 3-HP to acrylic acid (AA). In some cases, the residence time may be in a range of about 0.01 to about 1,000 seconds, about 1 to about 100 seconds, or about 5 to about 50 seconds. The residence time may be about 0.01, about 0.1, about 0.5, about 1, about 1.5, about 2, about 2.5, about 3, about 3.5, about 4.0, about 4.5, about 5.0, about 5.5, about 6.0, about 6.5, about 7.0, about 7.5, about 8.0, about 8.5, about 9.0, about 10, about 12, about 15, about 18, about 20, about 25, about 30, about 35, about 40, about 45, about 50, about 55, about 60, about 65, about 70, about 75, about 80, about 85, about 90, about 95, about 100 seconds, about 150 seconds, about 200 seconds, about 250 seconds, or about 300 seconds. The residence time may be less than about 0.01, less than about 0.1, less than about 0.5, less than about 1, less than about 1.5, less than about 2, less than about 2.5, less than about 3, less than about 3.5, less than about 4.0, less than about 4.5, less than about 5.0, less than about 5.5, less than about 6.0, less than about 6.5, less than about 7.0, less than about 7.5, less than about 8.0, less than about 8.5, less than about 9.0, less than about 10, less than about 12, less than about 15, less than about 18, less than about 20, less than about 25, less than about 30, less than about 35, less than about 40, less than about 45, less than about 50, less than about 55, less than about 60, less than about 65, less than about 70, less than about 75, less than about 80, less than about 85, less than about 90, less than about 95, less than about 100 seconds, less than about 150 seconds, less than about 200 seconds, less than about 250 seconds, or less than about 300 seconds. Under these conditions, generally less than about 20%, less than about 15%, less than about 10%, less than about 9%, less than about 8%, less than about 7%, less than about 6%, less than about 5%, less than about 4%, less than about 3%, less than about 2%, or less than about 1% of 3-HP is converted to acrylic acid.

The aqueous solution of 3-HP may exist in different states in different vessels. For example, the aqueous solution may be in a substantially liquid state in a first vessel. Upon being transferred to a second vessel, the liquid may be substantially vaporized. In some embodiments, at least about 70%, at least about 75%, at least about 80%, at least about 85%, at least about 90%, at least about 95%, or about 100% of the aqueous solution exists as a liquid in the first vessel. In some embodiments, at least about 50%, at least about 60%, at least about 70%, or at least about 85% of the aqueous solution exists as vapor in the second vessel, and at least about 50%, at least about 60%, at least about 70%, at least about 80%, at least about 85%, at least about 90%, or at least about 95% of the vapor from the second vessel is transferred to the third vessel. The vaporization in the second vessel and condensation of 3-HP in third vessel may lead to efficient separation of 3-HP, water and other organic acids from non-volatile impurities such as inorganic salts, lipids, proteins, carbohydrates, or other organic components. Condensation of the vapor may provide a 3-HP solution with improved purity compared to the original solution. In addition, by controlling the temperature and/or pressure in the second vessel, volatile components with different boiling points may be separated in the third vessel, for example by fractional condensation.

In one example, selective condensation of 3-HP in the presence of water may be achieved because 3-HP condenses at a higher temperature and the water (which has a lower boiling point than 3-HP) remains in the vapor phase. The condensation residue may contain 3-HP and other less volatile or non-volatile components. This residue can be subjected to another round of the purification procedure as described herein, thereby producing substantially water-free 3-HP.

In certain embodiments, selective condensation with two condensers is envisioned. For example, when a near neutral 3-HP fermentation broth is fed to the purification process, the 3-HP may be condensed away from water, other organic acids and ammonia components by using a high temperature condenser. The high temperature condenser may be operated at a temperature range of about 30 to about 100° C., about 40 to about 90° C., or about 50 to about 80° C., with the pressure ranging from about 50 to about 100 mbar, about 60 to about 90 mbar, or about 70 to about 80 mbar. Water may be subsequently condensed with acetic, propionic and acrylic acids, and ammonia using a low temperature condenser. The low temperature condenser may be operated at a temperature sufficiently low enough to condense water at the operating pressure, and may be in the range of about 10 to about 40° C., about 15 to about 35° C., or about 20 to about 30° C., with the pressure ranging from about 50 to about 100 mbar, about 60 to about 90 mbar, or about 70 to about 80 mbar.

The composition derived from the methods described herein may have a high 3-HP purity either with respect to the overall composition, or with respect to the nonaqueous components of the composition (i.e., all components of the composition other than water). A composition derived from the methods described herein may contain approximately 1 to approximately 60% water by weight and approximately 40% to approximately 99% nonaqueous components by weight, or less than about 50%, about 40%, about 30% or about 20% water by weight (all with the balance being nonaqueous components). The 3-HP purity within the nonaqueous components or the overall composition may be in a range of about 70% to about 99.5% by weight, about 75% to about 99% by weight, about 80% to about 95% by weight, or about 85% to about 90% by weight. The 3-HP purity within the nonaqueous components or the overall composition may be about 90%, about 91%, about 92%, about 93%, about 94%, about 95%, about 96%, about 97%, about 98%, about 99%, about 99.5%, or about 99.9% by weight. The 3-HP purity within the nonaqueous components or the overall composition may be at least about 70%, at least about 75%, at least about 80%, at least about 85%, at least about 90%, at least about 92%, at least about 94%, at least about 95%, or at least about 98%.

In some embodiments, 3-HP derived from the methods described herein may include acrylic acid. The amount of acrylic acid may be in a range of about 0.01 to 100,000 ppm, about 0.1 to 100,000 ppm, about 1 to 100,000 ppm, about 10 to 10,000 ppm, or about 100 to 1,000 ppm. The amount of acrylic acid may be about 0.01, about 0.05, about 0.1, about 0.5, about 1, about 2, about 3, about 4, about 5, about 6, about 7, about 8, about 9, about 10, about 15, about 20, about 25, about 30, about 35, about 40, about 45, about 60, about 65, about 70, about 75, about 80, about 85, about 90, about 95, about 100, about 150, about 200, about 250, about 300, about 350, about 400, about 450, about 500, about 600, about 700, about 800, about 900, about 1,000, about 2,000, about 3,000, about 4,000, about 5,000, about 6,000, about 7,000, about 8,000, about 9,000, about 10,000, about 20,000, about 50,000, or about 100,000 ppm. The amount of acrylic acid may be less than about 0.01, less than about 0.05, less than about 0.1, less than about 0.5, less than about 1, less than about 2, less than about 3, less than about 4, less than about 5, less than about 6, less than about 7, less than about 8, less than about 9, less than about 10, less than about 15, less than about 20, less than about 25, less than about 30, less than about 35, less than about 40, less than about 45, less than about 60, less than about 65, less than about 70, less than about 75, less than about 80, less than about 85, less than about 90, less than about 95, less than about 100, less than about 150, less than about 200, less than about 250, less than about 300, less than about 350, less than about 400, less than about 450, less than about 500, less than about 600, less than about 700, less than about 800, less than about 900, less than about 1,000, less than about 2,000, less than about 3,000, less than about 4,000, less than about 5,000, less than about 6,000, less than about 7,000, less than about 8,000, less than about 9,000, less than about 10,000, less than about 20,000, less than about 50,000, or less than about 100,000 ppm.

The amount of acrylic acid may be about 0.5% to about 5%, about 1% to about 4%, or about 2% to about 3% by weight. The amount of acrylic acid may be less than about 5% by weight, less than about 4% by weight, less than about 3% by weight, less than about 2% by weight, less than 1% by weight, or less than 0.5% by weight.

Systems and Devices

In one aspect, the present disclosure provides systems and devices for purifying 3-HP from an aqueous medium via flash evaporation. A system in accordance with the present invention is schematically shown in FIG. 1, and includes: a first vessel 2 that acts as a feed tank, a second vessel 8 that is an evaporator; a third vessel 14 and a fourth vessel 20, which are condensers; collection pots 16 and 22 associated with the third and fourth vessels, respectively; cold trap 26 and its associated collection pot 28; and a pump 32. Although the embodiment illustrated in FIG. 1 shows two condensers, in accordance with the present invention the system may include one, two, three or more condensers.

More specifically, and with continued reference to FIG. 1, the first vessel 2 is configured to receive an aqueous feed of a composition comprising 3-HP. In some embodiments, the aqueous feed is a fermentation broth. The aqueous 3-HP is maintained in first vessel 2 at a first temperature under a first pressure. The 3-HP composition is transferred to second vessel 8 where it is adjusted to a second temperature at a second pressure. The 3-HP composition is transferred via feed line 4 which, in accordance with certain embodiments, may be pre-heated. Feed line 4 may be pre-heated to a temperature at or about the first temperature or at or about the second temperature or to a temperature in between these temperatures. In some embodiments, the aqueous 3-HP is vaporized in the second vessel 8. In some embodiments, the vaporization is performed by flash evaporation. The flash evaporation may be performed using a thin film evaporator, a falling film or wiped film evaporator, or a rotary evaporator. In some cases, a rotary evaporator may be preferable. As illustrated in FIG. 1, second vessel 8 is a rotary flash evaporator. The driving force for the movement of an aqueous feed from the first vessel 2 to the second vessel 8 may be the pressure difference between the two vessels created by pump 32. The fermentation broth may be clarified prior to vaporization in the second vessel 8 through the use of a filtration system or a centrifuge (not shown). An aqueous feed may be clarified by a filtration system or centrifuge either prior to entering the first vessel 2, or between the first vessel 2 and second vessel 8.

With continued reference to FIG. 1, the system may further comprise at least one condenser 14 that is configured to condense at least a portion of vapor comprising 3-HP from the second vessel 8, thereby producing a 3-HP solution with improved purity compared to that of the aqueous feed. The system may comprise two, three, four, five, six, seven or more condensers, each of which may be operated at the same or different temperatures. In some embodiments, the system comprises two condensers as shown in FIG. 1. For example, the system may comprise a first condenser 14 having a collection pot 16, and a second condenser 20 having a collection pot 22. During operation, the condensate formed by condensers 14 and 16 is collected in the collection pots 20 and 22, and the distillate from condenser 14 is transferred to condenser 20 via first distillate line 18. In some cases, the first condenser 14 is operated at a higher temperature than that of second condenser 20. The temperature of the first condenser 14 may be at least about 5, at least about 10, at least about 15, at least about 20, at least about 25, at least about 30, at least about 35, at least about 40, at least about 45, at least about 50, at least about 60, at least about 70, or at least about 80° C. higher than that of the second condenser 20. In accordance with the embodiment shown in FIG. 1, the distillate from condenser 20 passes through a second distillate line 24 and into a cold trap 26. The distillate from condenser 20 is further cooled and the condensate is collected in cold trap collection pot 28. The temperature of the cold trap may be in the range of about –30 to –80, about –40 to –70, or about –50 to –60° C.

The system may further comprise an evaporator (not shown) to remove at least a portion of solvent, such as water, from either: (1) the 3-HP feed (e.g. the aqueous feed or fermentation broth) to concentrate the 3-HP feed prior to evaporation, or (2) the condensed 3-HP solution to provide a concentrated 3-HP solution. The concentration of 3-HP in the concentrated solution may be about 70% to about 80% by weight, about 75% to about 85% by weight, about 80% to about 90% by weight, or about 85% to about 95% by weight.

Other systems and devices are provided elsewhere in this application, for example the rolled film evaporator system (FIG. 21) and the partial condenser system (FIG. 22) discussed in more detail in the descriptions of the respective figures.

IV. Fermentation Broth

The fermentation broth used herein contains 3-HP. A variety of microbial systems for producing 3-HP have been described in the art, for example, US Publication Nos. 2011/0125118 and 2008/0199926, and U.S. Pat. No. 6,852,517, which are herein incorporated by reference for their teaching of 3-HP production pathways and methods of microbial 3-HP production. It is understood that these references and the following discussion provide examples to which the present invention can be applied. They are meant to be illustrative. As one of ordinary skill in the art will readily understand, the present invention can be applied to a variety of microbial systems which produce 3-HP and related compounds.

The microbial systems may comprise a carbon source, one or more microorganisms, and suitable media and culture conditions. The fermentation may be carried out in a bioproduction reactor. After fermenting for a certain period of time, the crude cell broth obtained may be further processed to yield high purity 3-HP or downstream products, using the methods provided in this disclosure.

The carbon source may be any carbon source suitable for the intended metabolic pathway. Suitable carbon source may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, corn steep liquor, sugar beet molasses, and barley malt. Additionally the carbon substrates may also be one-carbon substrates such as carbon dioxide, carbon monoxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity.

The microorganism may have one or more natural, introduced, or enhanced 3-HP bio-production pathways. The microorganism may comprise an endogenous 3-HP production pathway. The endogenous 3-HP production pathway may be enhanced to increase 3-HP production. On the other hand, the microorganism may not comprise an endogenous 3-HP production pathway. In this case, the pathway can be introduced through, for example, genetic engineering. A microorganism may be selected from bacteria, cyanobacteria, filamentous fungi, and yeasts. Since 3-HP produced during fermentation may be toxic to the microorganism used in the process, the microorganism may further comprise modifications to increase tolerance to 3-HP.

Microorganisms may include, but are not limited to, any gram negative organisms, more particularly a member of the family Enterobacteriaceae, such as *E. coli, Oligotropha carboxidovorans*, or *Pseudomononas* sp.; any gram positive microorganism, for example *Bacillus subtilis, Lactobacillus* sp. or *Lactococcus* sp.; a yeast, for example *Saccharomyces cerevisiae, Pichia pastoris* or *Pichia stipitis*; and other groups or microbial species. More particularly, suitable microbial hosts for the bio-production of 3-HP generally include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula*, and *Saccharomyces*. Hosts that may be particularly of interest include: *Oligotropha carboxidovorans* (such as strain OM5), *Escherichia coli, Alcaligenes eutrophus (Cupriavidus necator), Bacillus licheniformis, Paenibacillus macerans, Rhodococcus erythropolis, Pseudomonas putida, Lactobacillus plantarum, Enterococcus faecium, Enterococcus gallinarum, Enterococcus faecalis, Bacillus subtilis*, and *Saccharomyces cerevisiae*.

There may be a variety of pathways and/or mechanisms to increase 3-HP production, for example, reducing the activity of fatty acid synthase and/or enhancing the activity of malonyl-CoA reductase. The modulation of the pathways can be achieved by a variety of methods described in the art, such as those provided in WO/2011/038364, WO/2011/063363, and WO/2011/094457, which are hereby incorporated by reference in their entirety. Also incorporated by reference for the teachings of particular enzymes and metabolic pathways are U.S. Pat. No. 7,943,362 and US Publication No. US2011/0183391. In addition, one or more additives may be added to the cell culture to modulate fatty acid synthase or malonyl-CoA reductase to increase the production of 3-HP.

In addition to an appropriate carbon source, bio-production media may contain suitable minerals, salts, cofactors, buffers and other components, known to those skilled in the art, suitable for the growth of the cultures and promotion of the enzymatic pathways necessary for the production of 3-HP or other products.

Typically cells are grown at a temperature in the range of about 25° C. to about 40° C. (or up to 70° C. for thermophilic microorganisms) in an appropriate medium comprising water. Suitable growth media include common commercially prepared media such as Luria Bertani (LB) broth, M9 minimal media, Sabouraud Dextrose (SD) broth, yeast medium (YM) broth, yeast synthetic minimal media (Ymin), and minimal media such as M9 minimal media. Other defined or synthetic growth media may also be used, and the appropriate medium for growth of the particular microorganism will be known by one skilled in the art of microbiology or bio-production science. In various embodiments a minimal media may be developed and used that does not comprise, or that has a low level of certain components, for example less than 10, 5, 2 or 1 g/L of a complex nitrogen source including but not limited to yeast extract, peptone, tryptone, soy flour, corn steep liquor, or casein. These minimal medias may also be supplemented with vitamin mixtures including biotin, vitamin B12 and derivatives of vitamin B12, thiamin, pantothenate and other vitamins. Minimal medias may also comprise simple inorganic nutrient sources containing less than 28, 17, or 2.5 mM phosphate, less than 25 or 4 mM sulfate, and/or less than 130 or 50 mM total nitrogen.

Bio-production media may contain suitable carbon substrates for the intended metabolic pathways. As described elsewhere in this disclosure, suitable carbon substrates may include carbon monoxide, carbon dioxide, various monomeric and oligomeric sugars, amines, and amino acids.

Suitable pH ranges for bio-production may be between pH 3.0 to pH 10.0, where pH 6.0 to pH 8.0 is a typical pH range for the initial condition. However, the actual culture conditions for a particular embodiment are not meant to be limited by these pH ranges.

Bio-production may be performed under aerobic, microaerobic, or anaerobic conditions, with or without agitation and with or without external heating or cooling.

The amount of 3-HP or other product(s) produced in a bio-production medium generally can be determined using a number of methods known in the art, for example, high performance liquid chromatography (HPLC), gas chromatography (GC), or GC/mass spectroscopy (MS).

Any suitable microorganism, including the microorganisms described in this disclosure, may be introduced into an industrial bio-production system where the microorganisms converts a carbon source into 3-HP in a commercially viable operation. The bio-production system includes the introduction of such a microorganism into a bioreactor vessel, with a carbon source substrate and bio-production media suitable for growing the microorganism, and maintaining the bio-production system within a suitable temperature range (and dissolved oxygen concentration range if the reaction is aerobic or microaerobic) for a suitable time to obtain a desired conversion of a portion of the substrate molecules to 3-HP. The fermentation process may be monitored by measuring the concentration of 3-HP in crude fermentation broth. Industrial bio-production systems and their operation are well-known to those skilled in the arts of chemical engineering and bioprocess engineering.

Bio-production may be performed under aerobic, microaerobic, or anaerobic conditions, with or without agitation. The operation of cultures and populations of microorganisms to achieve aerobic, microaerobic and anaerobic conditions are known in the art, and dissolved oxygen levels of a liquid culture comprising a nutrient media and such microorganism populations may be monitored to maintain or confirm a desired aerobic, microaerobic or anaerobic condition.

V. Biosignatures

3-HP obtained from the methods described herein and any downstream chemical or consumer products derived therefrom may have a unique biosignature. This unique biosignature results from cosmic radiation that produces $^{14}C$ ("radiocarbon") in the stratosphere by neutron bombardment of nitrogen:

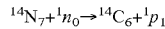

$$^{14}N_7 + {}^{1}n_0 \rightarrow {}^{14}C_6 + {}^{1}p_1$$

$^{14}C$ has a half-life of about 5,730 years and its concentration stays approximately constant across the globe due to rapid mixing of the atmosphere. Since living organisms utilize carbon from the atmosphere, the level of $^{14}C$ with respect to all other carbon forms in living organisms is approximately the same as the level of $^{14}C$ in the atmosphere. Currently, the $^{14}C$ level in the atmosphere is about 1.2 parts per trillion carbon. On the other hand, following death, organisms lose $^{14}C$ due to the beta decay of $^{14}C$ to give $^{14}N$. Therefore, fossil fuels, or products derived from fossil fuels, generally have a lower level of $^{14}C$ than that of products derived from living organisms. The level of $^{14}C$ can be measured by liquid scintillation beta spectrometry or mass spectrometry.

The 3-HP fermentation broth feed utilized in the current process is produced from biological processes and, as such, has a $^{14}C$ level distinct from 3-HP produced from petroleum-based processes. This $^{14}C$ level serves as a unique biosignature which will be detectable in any downstream chemical or consumer products derived from the purified 3-HP produced biologically. In some embodiments, the 3-HP and any derived downstream chemical or consumer products have a $^{14}C$ level of about 0.8, about 1.0, or about 1.2 parts per trillion carbon. In some embodiments, the 3-HP and any derived downstream chemical or consumer products have a $^{14}C$ level of at least about 0.8, at least about 1.0, or at least about 1.2 parts per trillion carbon.

VI. Downstream Chemical and Consumer Products

3-HP purified according to the methods provided in this disclosure may be converted to various other products having industrial uses including, but not limited to, acrylamide, acrylic acid, esters of acrylic acid, 1,3-propanediol, and other chemicals, collectively referred to as "downstream chemical products" or "downstream products." In some instances the conversion is associated with the separation and/or purification steps. These downstream chemical products are useful for producing a variety of consumer products which are described in more detail below. The methods of the present invention include steps to produce downstream products of 3-HP.

As a C3 building block, 3-HP offers much potential in a variety of chemical conversions to commercially important intermediates, industrial end products, and consumer products. For example, 3-HP may be converted to acrylic acid, acrylates (e.g., acrylic acid salts and esters), 1,3-propanediol, malonic acid, ethyl-3-hydroxypropionate, ethyl ethoxy propionate, propiolactone, acrylamide, or acrylonitrile.

Additionally, 3-HP may be oligomerized or polymerized to form poly(3-hydroxypropionate) homopolymers, or co-polymerized with one or more other monomers to form various co-polymers. Because 3-HP has only a single stereoisomer, polymerization of 3-HP is not complicated by the stereo-specificity of monomers during chain growth. This is in contrast to (S)-2-hydroxypropanoic acid (also known as lactic acid), which has two (D, L) stereoisomers that must be considered during its polymerizations.

As will be further described, 3-HP can be converted into derivatives starting (i) substantially as the protonated form of 3-hydroxypropionic acid; (ii) substantially as the deprotonated form, 3-hydroxypropionate; or (iii) as mixtures of the protonated and deprotonated forms. Generally, the fraction of 3-HP present as the acid versus the salt will depend on the pH, the presence of other ionic species in solution, temperature (which changes the equilibrium constant relating the acid and salt forms), and, to some extent, pressure. Many chemical conversions may be carried out from either of the 3-HP forms, and overall process economics will typically dictate the form of 3-HP for downstream conversion.

Acrylic acid obtained from 3-HP purified by the methods described in this disclosure may be further converted to various polymers. For example, the free-radical polymerization of acrylic acid takes place by polymerization methods known to the skilled worker and can be carried out, for example, in an emulsion or suspension in aqueous solution or another solvent. Initiators, such as but not limited to organic peroxides, are often added to aid in the polymerization. Among the classes of organic peroxides that may be used as initiators are diacyls, peroxydicarbonates, monoperoxycarbonates, peroxyketals, peroxyesters, dialkyls, and hydroperoxides. Another class of initiators is azo initiators, which may be used for acrylate polymerization as well as co-polymerization with other monomers. U.S. Pat. Nos. 5,470,928; 5,510,307; 6,709,919; and 7,678,869 teach various approaches to polymerization using a number of initiators, including organic peroxides, azo compounds, and other chemical types, and are incorporated by reference for such teachings as applicable to the polymers described herein.

Accordingly, it is further possible for co-monomers, such as crosslinkers, to be present during the polymerization. The free-radical polymerization of the acrylic acid obtained from dehydration of 3-HP, as produced herein, in at least partly neutralized form and in the presence of crosslinkers is practiced in certain embodiments. This polymerization may result in hydrogels which can then be comminuted, ground and, where appropriate, surface-modified, by known techniques.

An important commercial use of polyacrylic acid is for superabsorbent polymers. This specification hereby incorporates by reference Modern Superabsorbent Polymer Technology, Buchholz and Graham (Editors), Wiley-VCH, 1997, in its entirety for its teachings regarding superabsorbent polymers components, manufacture, properties and uses. Superabsorbent polymers are primarily used as absorbents for water and aqueous solutions for diapers, adult incontinence products, feminine hygiene products, and similar consumer products. In such consumer products, superabsorbent materials can replace traditional absorbent materials such as cloth, cotton, paper wadding, and cellulose fiber. Superabsorbent polymers absorb, and retain under a slight mechanical pressure, up to 25 times or more their weight in liquid. The swollen gel holds the liquid in a solid, rubbery state and prevents the liquid from leaking. Superabsorbent polymer particles can be surface-modified to produce a shell structure with the shell being more highly cross-linked than the rest of the particle. This technique improves the balance of absorption, absorption under load, and resistance to gel-blocking. It is recognized that superabsorbent polymers have uses in fields other than consumer products, including agriculture, horticulture, and medicine.

Superabsorbent polymers are prepared from acrylic acid (such as acrylic acid derived from 3-HP provided herein) and a crosslinker, by solution or suspension polymerization. Exemplary methods include those provided in U.S. Pat. Nos. 5,145,906; 5,350,799; 5,342,899; 4,857,610; 4,985,518; 4,708, 997; 5,180,798; 4,666,983; 4,734,478; and 5,331, 059, each incorporated by reference for their teachings relating to superabsorbent polymers.

Among consumer products, a diaper, a feminine hygiene product, and an adult incontinence product are made with superabsorbent polymer that itself is made substantially from acrylic acid converted from 3-HP made in accordance with the present invention.

Diapers and other personal hygiene products may be produced that incorporate superabsorbent polymers made from acrylic acid made from 3-HP which is produced and purified by the teachings of the present application. The following provides general guidance for making a diaper that incorporates such superabsorbent polymer. The superabsorbent polymer first is molded into an absorbent pad that may be vacuum formed, and in which other materials, such as a fibrous material (e.g., wood pulp) are added. The absorbent pad then is assembled with sheet(s) of fabric, generally a nonwoven fabric (e.g., made from one or more of nylon, polyester, polyethylene, and polypropylene plastics) to form diapers.

More particularly, in one non-limiting process, multiple pressurized nozzles, located above a conveyer belt, spray superabsorbent polymer particles (e.g., about 400 micron size or larger), fibrous material, and/or a combination of these onto the conveyer belt at designated spaces/intervals. The conveyor belt is perforated and under vacuum from below, so that the sprayed on materials are pulled toward the belt surface to form a flat pad. In various embodiments, fibrous material is applied first on the belt, followed by a mixture of fibrous material and the superabsorbent polymer particles, followed by fibrous material, so that the superabsorbent polymer is concentrated in the middle of the pad. A leveling roller may be used toward the end of the belt path to yield pads of uniform thickness. Each pad thereafter may be further processed, such as to cut it to a proper shape for the diaper, or the pad may be in the form of a long roll sufficient for multiple diapers. Thereafter, the pad is sandwiched between a top sheet and a bottom sheet of fabric (one generally being liquid pervious, the other liquid impervious), for example on a conveyor belt, and these are attached together, for example by gluing, heating or ultrasonic welding, and cut into diaper-sized units (if not previously so cut). Additional features may be provided, such as elastic components, strips of tape, etc., for fit and ease of wearing by a person.

The ratio of the fibrous material to polymer particles is known to affect performance characteristics. In some cases, this ratio is between 75:25 and 90:10 (see e.g., U.S. Pat. No. 4,685,915, incorporated by reference for its teachings of diaper manufacture). Other disposable absorbent articles may be constructed in a similar fashion, such as absorbent articles for adult incontinence, feminine hygiene (sanitary napkins), tampons, etc. (see, for example, U.S. Pat. Nos. 5,009,653; 5,558,656; and 5,827,255 incorporated by reference for their teachings of sanitary napkin manufacture).

Low molecular weight polyacrylic acid has uses for water treatment, and as a flocculant and thickener for various applications including cosmetics and pharmaceutical preparations. For these applications, the polymer may be uncross-linked or lightly cross-linked, depending on the specific application. The molecular weights are typically from about 200 to about 1,000,000 g/mol. Preparation of these low molecular weight polyacrylic acid polymers is described in U.S. Pat. Nos. 3,904,685; 4,301,266; 2,798,053; and 5,093, 472, each of which is incorporated by reference for its teachings relating to methods to produce these polymers.

Acrylic acid may be co-polymerized with one or more other monomers selected from acrylamide, 2-acrylamido-2-methylpropanesulfonic acid, N,N-dimethylacrylamide, N-isopropylacrylamide, methacrylic acid, and methacrylamide, to name a few. The relative reactivities of the monomers affect the microstructure and thus the physical properties of the polymer. Co-monomers may be derived from 3-HP, or otherwise provided, to produce co-polymers. Ullmann's Encyclopedia of Industrial Chemistry, Polyacrylamides and Poly(Acrylic Acids), WileyVCH Verlag GmbH, Wienham (2005), is incorporated by reference herein for its teachings of polymer and co-polymer processing.

Acrylic acid can in principle be copolymerized with almost any free-radically polymerizable monomers including styrene, butadiene, acrylonitrile, acrylic esters, maleic acid, maleic anhydride, vinyl chloride, acrylamide, itaconic acid, and so on. End-use applications typically dictate the co-polymer composition, which influences properties. Acrylic acid also may have a number of optional substitutions and, after such substitutions, may be used as a monomer for polymerization, or co-polymerization reactions. As a general rule, acrylic acid (or one of its co-polymerization monomers) may be substituted by any substituent that does not interfere with the polymerization process, such as alkyl, alkoxy, aryl, heteroaryl, benzyl, vinyl, allyl, hydroxy, epoxy, amide, ethers, esters, ketones, maleimides, succinimides, sulfoxides, glycidyl and silyl (see e.g., U.S. Pat. No. 7,678, 869, incorporated by reference above, for further discussion). The following paragraphs provide a few non-limiting examples of copolymerization applications.

Paints that comprise polymers and copolymers of acrylic acid and its esters are in wide use as industrial and consumer products. Aspects of the technology for making such paints can be found in e.g., U.S. Pat. Nos. 3,687,885 and 3,891,591, incorporated by reference for their teachings of such paint manufacture. Generally, acrylic acid and its esters may form homopolymers or copolymers among themselves or with other monomers, such as amides, methacrylates, acrylonitrile, vinyl, styrene and butadiene. A desired mixture of homopolymers and/or copolymers, referred to in the paint industry as "vehicle" (or "binder") are added to an aqueous solution and agitated sufficiently to form an aqueous dispersion that includes sub-micrometer sized polymer particles. The paint cures by coalescence of these vehicle particles as the water and any other solvent evaporate. Other additives to the aqueous dispersion may include pigment, filler (e.g., calcium carbonate, aluminum silicate), solvent (e.g., acetone, benzol, alcohols, etc., although these are not found in certain no VOC paints), thickener, and additional additives depending on the conditions, applications, intended surfaces, etc. In many paints, the weight percent of the vehicle portion may range from about nine to about 26 percent, but for other paints the weight percent may vary beyond this range.

Acrylic-based polymers are used for many coatings in addition to paints. For example, for paper coating latexes, acrylic acid is used from 0.1-5.0%, along with styrene and butadiene, to enhance binding to the paper and modify rheology, freeze-thaw stability and shear stability. In this context, U.S. Pat. Nos. 3,875,101 and 3,872,037 are incorporated by reference for their teachings regarding such latexes. Acrylate-based polymers also are used in many inks, particularly UV curable printing inks. For water treatment, acrylamide and/or hydroxy ethyl acrylate are commonly co-polymerized with acrylic acid to produce low molecular-weight linear polymers. In this context, U.S. Pat. Nos. 4,431,547 and 4,029,577 are incorporated by reference for their teachings of such polymers. Co-polymers of acrylic acid with maleic acid or itaconic acid are also produced for water-treatment applications, as described in U.S. Pat. No. 5,135,677, incorporated by reference for that teaching. Sodium acrylate (the sodium salt of glacial acrylic acid) can be co-polymerized with acrylamide (which may be derived from acrylic acid via amidation chemistry) to make an anionic co-polymer that is used as a flocculant in water treatment.

For thickening agents, a variety of co-monomers can be used, such as those described in U.S. Pat. Nos. 4,268,641 and 3,915,921, incorporated by reference for their description of these co-monomers. U.S. Pat. No. 5,135,677 describes a number of co-monomers that can be used with acrylic acid to produce water-soluble polymers, and is incorporated by reference for such description.

In some cases, conversion to downstream products may be made enzymatically. For example, 3-HP may be converted to 3-HP-CoA, which then may be converted into polymerized 3-HP with an enzyme having polyhydroxy acid synthase activity (EC 2.3.1.-). Also, 1,3-propanediol can be made using polypeptides having oxidoreductase activity or reductase activity (e.g., enzymes in the EC 1.1.1.-class of enzymes). Alternatively, when creating 1,3-propanediol from 3-HP, a combination of (1) a polypeptide having aldehyde dehydrogenase activity (e.g., an enzyme from the 1.1.1.34 class) and (2) a polypeptide having alcohol dehydrogenase activity (e.g., an enzyme from the 1.1.1.32 class) can be used. Polypeptides having lipase activity may be used to form esters. Enzymatic reactions such as these may be conducted in vitro, such as using cell-free extracts, or in vivo.

Thus, various embodiments described in this disclosure, such as methods of making a chemical, include conversion steps to any downstream products of microbially produced 3-HP, including but not limited to those chemicals described herein, in the incorporated references, and known in the art. For example, in some cases, 3-HP is produced and converted to polymerized-3-HP (poly-3-HP) or acrylic acid. In some cases, 3-HP or acrylic acid can be used to produce polyacrylic acid (polymerized acrylic acid, in various forms), methyl acrylate, acrylamide, acrylonitrile, propiolactone, ethyl 3-HP, malonic acid, 1,3-propanediol, ethyl acrylate, n-butyl acrylate, hydroxypropyl acrylate, hydroxyethyl acrylate, isobutyl acrylate, 2-ethylhexyl acrylate, and acrylic acid or an acrylic acid ester to which an alkyl or aryl addition may be made, and/or to which halogens, aromatic amines or amides, and aromatic hydrocarbons may be added.

Reactions that form downstream compounds such as acrylates or acrylamides can be conducted in conjunction with use of suitable stabilizing agents or inhibiting agents reducing the likelihood of polymer formation. See, for example, U.S. Publication No. 2007/0219390, incorporated by reference in its entirety. Stabilizing agents and/or inhibiting agents include, but are not limited to, e.g., phenolic compounds (e.g., dimethoxyphenol (DMP) or alkylated phenolic compounds such as di-tert-butyl phenol), quinones (e.g., t-butyl hydroquinone or the monomethyl ether of hydroquinone (MEHQ)), and/or metallic copper or copper salts (e.g., copper sulfate, copper chloride, or copper acetate). Inhibitors and/or stabilizers can be used individually or in combinations as will be known by those of skill in the art.

In some cases, the one or more downstream compounds are recovered at a molar yield of up to about 100 percent, or a molar yield in the range from about 70 percent to about 90 percent, or a molar yield in the range from about 80 percent to about 100 percent, or a molar yield in the range from about 90 percent to about 100 percent. Such yields may be the result of single-pass (batch or continuous) or iterative separation and purification steps in a particular process.

The methods described in this disclosure can also be used to produce downstream compounds derived from 3-HP, such as but not limited to, polymerized-3-HP (poly-3-HP), acrylic acid, polyacrylic acid (polymerized acrylic acid, in various forms), copolymers of acrylic acid and acrylic esters, acrylamide, acrylonitrile, propiolactone, ethyl 3-HP, malonic acid, and 1,3-propanediol. Also, among esters that are formed are methyl acrylate, ethyl acrylate, n-butyl acrylate, hydroxypropyl acrylate, hydroxyethyl acrylate, isobutyl acrylate, and 2-ethylhexyl acrylate. These and/or other acrylic acid and/or other acrylate esters may be combined, including with other compounds, to form various known acrylic acid-based polymers. Numerous approaches may be employed for such downstream conversions, generally falling into enzymatic, catalytic (chemical conversion process using a catalyst), thermal, and combinations thereof (including some wherein a desired pressure is applied to accelerate a reaction). For example, without being limiting, acrylic acid may be made from 3-HP via a dehydration reaction, methyl acrylate may be made from 3-HP via dehydration and esterification, the latter to add a methyl group (such as using methanol), acrylamide may be made from 3-HP via dehydration and amidation reactions, acrylonitrile may be made via a dehydration reaction and forming a nitrile moiety, propiolactone may be made from 3-HP via a ring-forming internal esterification reaction, ethyl-3-HP may be made from 3-HP via esterification with ethanol, malonic acid may be made from 3-HP via an oxidation reaction, and 1,3-propanediol may be made from 3-HP via a reduction reaction. Additionally, it is appreciated that various derivatives of the derivatives of 3-HP and acrylic acid may be made, such as the various known polymers of acrylic acid and its derivatives. Production of such polymers is considered within the scope of the present invention. Copolymers containing acrylic acid and/or esters have been widely used in the pharmaceutical formulation to achieve extended or sustained release of active ingredients, for example as coating material. Downstream compounds may also be converted to consumer products such as diapers, carpet, paint, and adhesives.

Another important product, acrylamide, has been used in a number of industrial applications. Acrylamide may be produced from 3-HP, for example, without being limiting, via an esterification-amidation-dehydration sequence. Refluxing an alcohol solution of 3-HP in the presence of an acid or Lewis acid catalyst described herein would lead to a 3-HP ester. Treatment of the 3-HP ester with either an ammonia gas or an ammonium ion could yield 3-HP amide. Finally, dehydration of the 3-HP amide with dehydration reagents described elsewhere in this disclosure could produce acrylamide. The steps mentioned herein may be rearranged to produce the same final product acrylamide.

Polymerization of acrylamide can be achieved, for example, and without being limiting, by radical polymerization. Polyacrylamide polymers have been widely used as additives for treating municipal drinking water and waste water. In addition, they have found applications in gel electrophoresis, oil-drilling, papermaking, ore processing, and the manufacture of permanent press fabrics.

EXAMPLES

Example 1

Vaporization of 3-HP in a Flash Evaporator

This experiment sought to determine whether 3-HP could be purified by flash evaporation. The results showed that flash evaporation could be used to purify 3-HP from an aqueous medium with very little conversion to AA.

Figure 2:
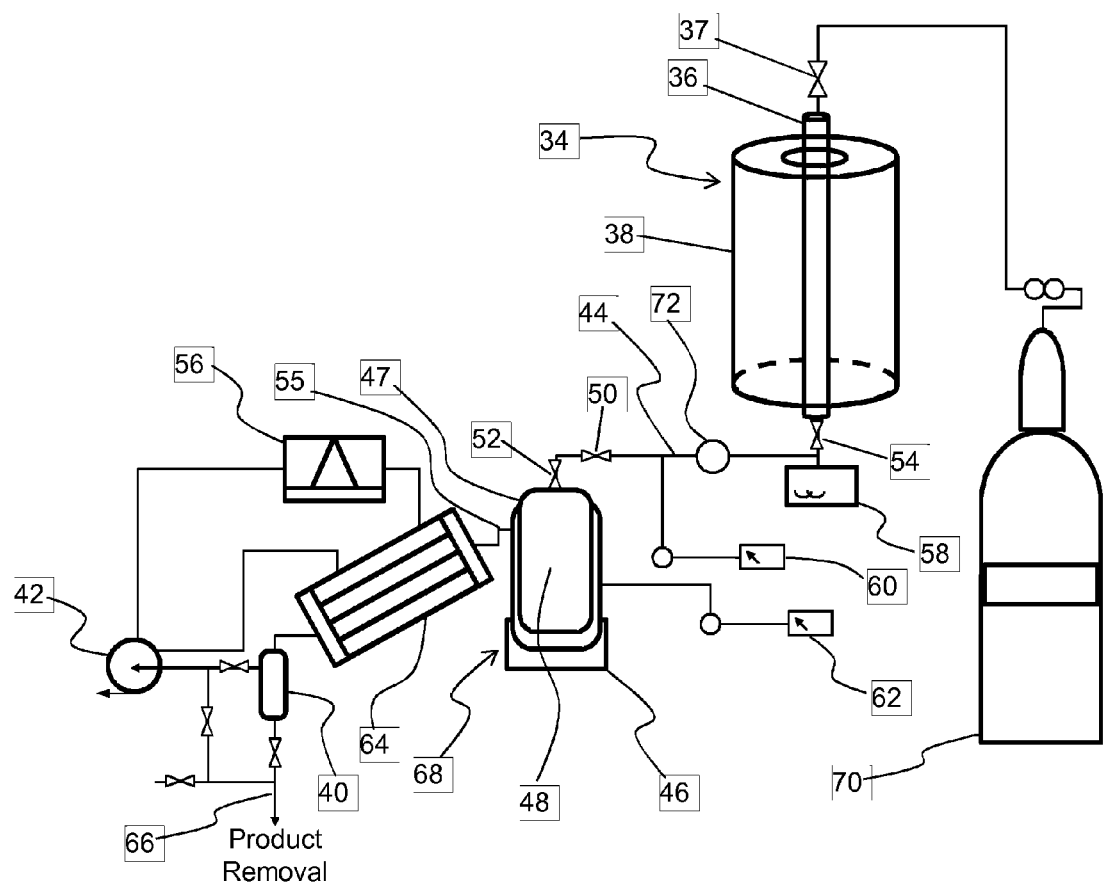
FIG. 2 is a schematic of the flash evaporation apparatus discussed in Example 1.

The flash evaporation apparatus used for these studies is shown in FIG. 2. With reference to FIG. 2, the apparatus includes a feed tank assembly 34 having a one-inch diameter feed tube 36 inside a tube furnace 38. The apparatus further includes an evaporator assembly 68. The evaporator assembly 68 includes a glass vessel 47 having a vacuum chamber 48, and further includes a heating mantle 46 configured to heat vacuum chamber 48. Feed tube 36 is connected to vacuum chamber 48 via a heated supply line 44, which is covered with heating tape that is connected to a heating tape temperature controller 60. Heated supply line 44 also includes valves 50, 52, and 54 and pressure relief valve 72. Vacuum chamber 48 is connected to distillate line 55 that allows distillate from the evaporator assembly 68 to travel to a condenser 64. A chiller 56 is included to provide cold water to condenser 64. A vacuum flask 40 is connected to condenser 64 to collect the condensate. The apparatus further includes pump 42 and nitrogen tank 70 to regulate pressure along the system.

An aqueous solution of synthetic 3-HP (150 mL; approximately 500 g/L) was placed into feed tube 36 inside of the tube furnace 38. After sealing the tube furnace 38, the temperature controllers attached to furnace 38 and the heating tape controller 60 were set to about 150° C. The vacuum chamber 48 was also heated by setting the temperature of heating mantle 46 to about 300° C. The temperature of the apparatus was allowed to equilibrate and a pressure of 16 mbar was set using a vacuum pump 42. The equilibration period was approximately two hours. At the time of sample injection, as described below, the system had the following characteristics: the glass vessel 47 was at a temperature of about 350° C.; the heating tape along heated supply line 44, between feed tank assembly 34 and evaporator assembly 68, was at a temperature of about 120° C.; the thermocouple 58 at the feed tube 36 outlet indicated a temperature of about 130° C., feed tube 36 had a pressure of about 60 psi, and vacuum chamber 48 had a pressure of about 6 mbar.

The sample was introduced ("flashed") into the vacuum chamber 48 of the evaporator assembly 68 by first opening the valve 54 at the outlet of the feed tube 36 and the valve 50 upstream of the vacuum chamber 48, followed by slowly opening the valve 52 at the inlet of the vacuum chamber 48. This allowed a small amount of heated 3-HP solution to enter into the vacuum chamber 48. A thermocouple at the bottom of the vacuum chamber 48 monitored the temperature, which was always at least about 130° C. When the feed tube 36 pressure dropped below about 60 psi, the nitrogen regulator (set to about 55 psi) valve 37 was opened to the inlet of the feed tube 36, to maintain pressure as the feed tube 36 emptied. Samples of condensed solution were collected in the vacuum flask 40.

During the experiment, the temperature of the heated glass flash vessel 47 decreased to about 250° C. as the vaporization occurred. The temperature of the heating tape along line 44 dropped to between about 98° C. and about 120° C. The thermocouple 58 at the feed tube 36 outlet indicated a temperature between about 140° C. and about 150° C. The pressure of the feed tube 36 was maintained at about 60 psi. Three samples were collected from the vacuum flask 40 via line 66.

Figure 3:
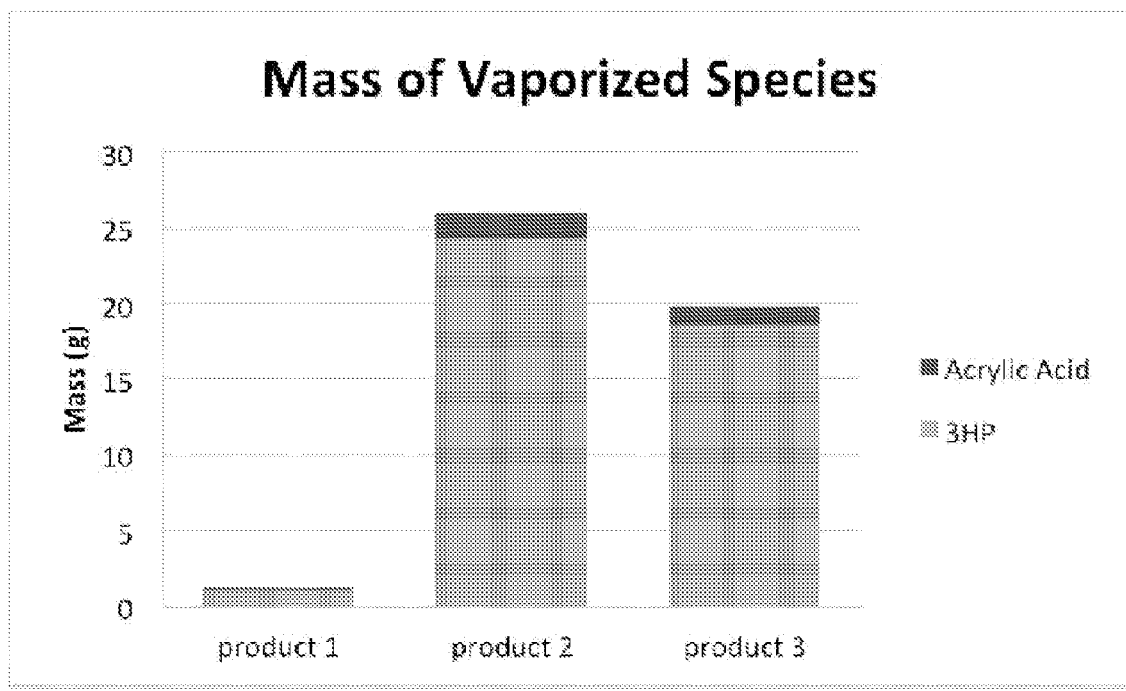
FIG. 3 shows the mass of vaporized species obtained as described in Example 1.

FIG. 3 shows the mass of 3-HP and AA (plus water generated during dehydration) present in the three collected product samples. Product 1 was collected at 1.75 hours. Product 2 was collected at 2.0 hours. Product 3 was collected at 2.5 hours. The three samples show approximately 1%, 5%, and 6% conversion to AA, respectively, as determined by reversed-phase HPLC. The overall conversion to AA, based on the mass collected in the samples, was approximately 7%. Dehydration is most likely to have occurred on the surface of the glass flash vessel 47 and it is likely that maintaining the temperature of this vessel below 250° C. would minimize or eliminate the conversion of 3-HP to AA.

Figure 4:
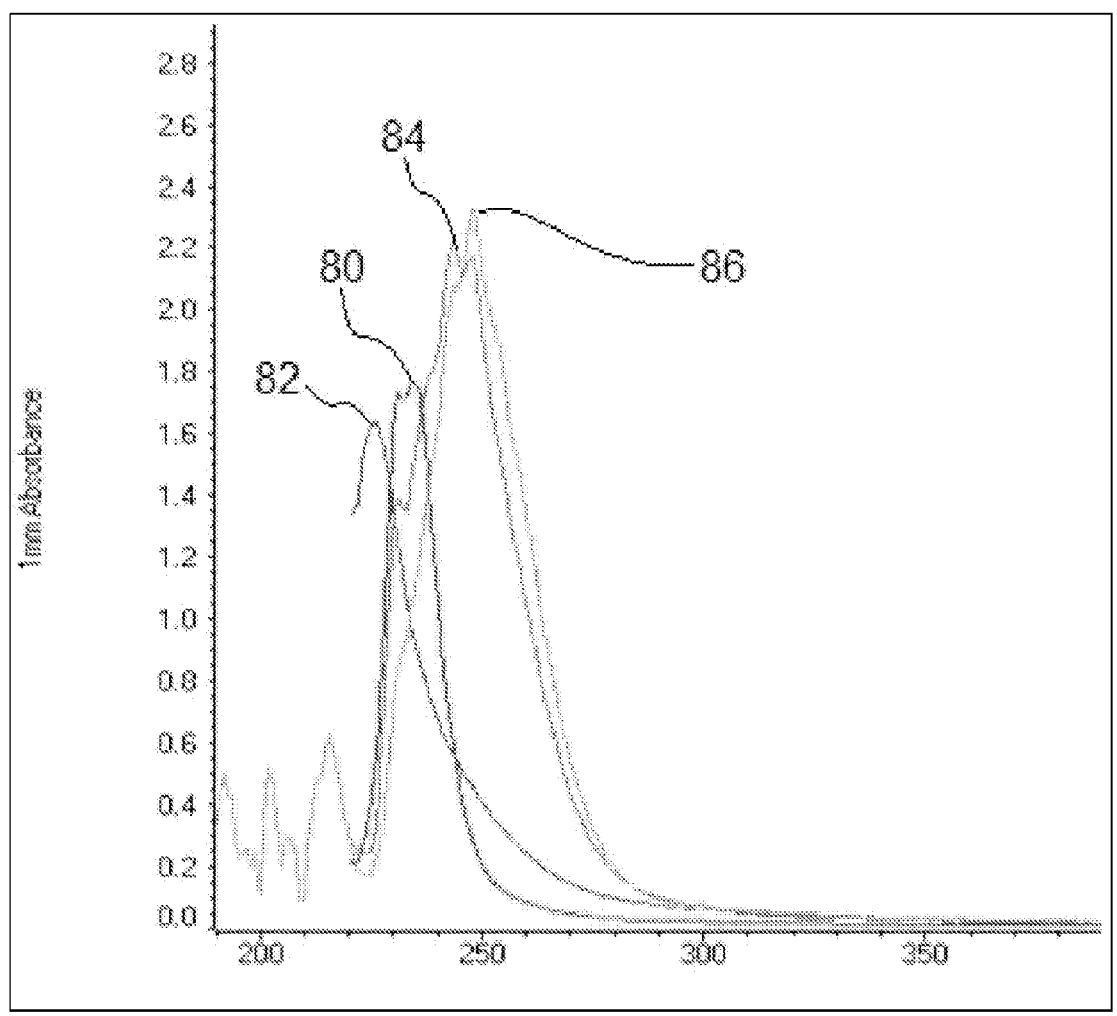
FIG. 4 shows UV/Vis spectra of feed and three product samples, as described in Example 1.

The feed and the three product samples were then analyzed by ultraviolet/visible (UV/Vis) absorption spectroscopy. The spectra are shown in FIG. 4. With reference to FIG. 4, the feed is represented by line 80, and product 1 (1.75 hr), product 2 (2 hr) and product 3 (3 hr) are represented by lines 82, 84, and 86, respectively. Feed line 80 shows a moderately clean peak at 230 nm, representing 3-HP. Peaks to the left of 230 nm are indicative of dilute 3-HP solutions (e.g., product 1, line 82, at 1.75 h). Peaks between 230 nm (3-HP) and 275 nm (AA) indicate solutions with low levels of AA, with or without 3-HP. In this experiment, the samples from 2.0 hours (product 2, line 84) and 2.5 hours (product 3, line 86) each exhibit peaks between 230 nm and 275 nm, and contain high levels of 3-HP with very low levels of AA.

The mass balance used above was based on 150 mL of 3-HP solution, at a concentration of approximately 500 g/L. For this example, 63% of the mass fed was measured in the product. The mass of AA formed includes the mass of water generated during dehydration, such that 100% mass balance would be expected even if dehydration occurred. Due to the condenser configuration, substantial liquid volume (~50 mL) remained inside the condenser and was therefore not analyzed. Because the glass-portion of the system was warmed by boiling water at atmospheric pressure, Product 1 was substantially diluted by water that collected in the condenser. As a result, the mass balance was not expected to fully close.

Example 2

Effect of pH on Recovery of 3-HP and AA

This experiment sought to determine an optimal pH for evaporation of 3-HP from fermentation broth. Surprisingly, the results showed that more 3-HP was recovered from solutions adjusted to a pH of 5.0 than solutions adjusted to pH 2.0, 3.0, 4.0, or 6.0. This result was unexpected because the pKa of 3-HP is approximately 4.5, and 3-HP is expected to exist substantially in its salt form at a pH of 5.0.

Figure 5:
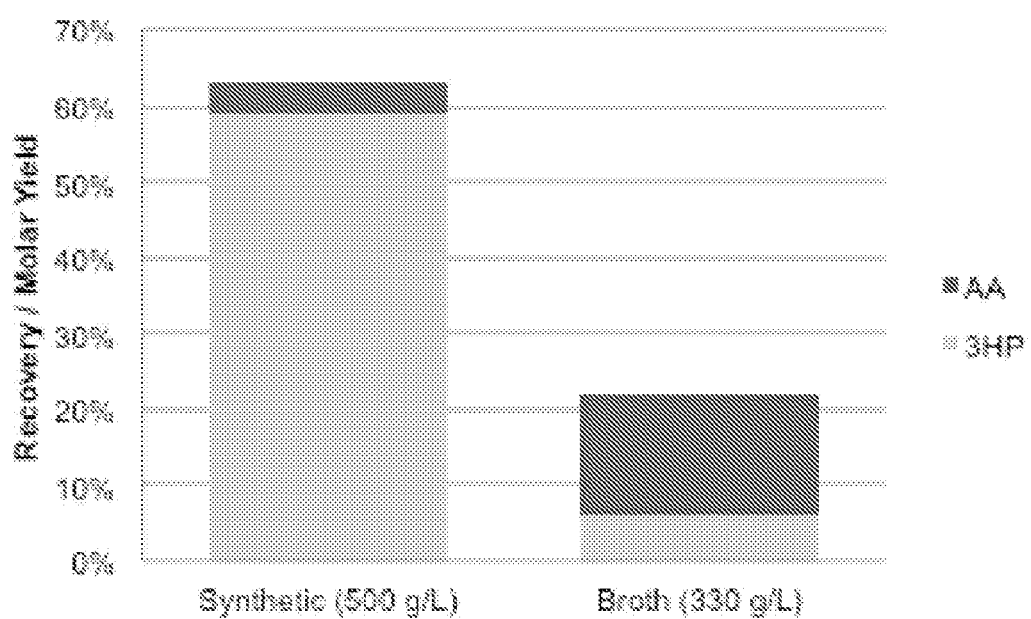
FIG. 5 shows recovery of synthetic 3-HP from aqueous medium vs. recovery of 3-HP from clarified fermentation broth. The difference in recovery is due to the accumulation of solids in the flash evaporator when fermentation broth is used.

Additionally, this experiment sought to determine the effect of pH on the consistency of the solids formed during evaporation. These solids can accumulate on the walls of the evaporative chamber, reducing the effectiveness of flash evaporation and impeding 3-HP recovery (e.g., FIG. 5). In order to optimize the process, evaporation can optionally be performed in a rotary evaporation vessel (e.g., ROTO-THERM®, Artisan Industries, Inc.) designed to provide mechanically-assisted removal of the solids that accumulate during evaporation. This can reduce or eliminate the accumulation of solids on the walls of the flash chamber, resulting in more effective evaporation and enhanced 3-HP recovery.

Two-hundred-fifty milliliters of concentrated fermentation broth containing 3-HP was divided into five 50 mL aliquots. The pH of the aliquots was adjusted, using concentrated sulfuric acid, to 2.0, 3.0, 4.0, 5.0, or 6.0. All samples were brown, with no visible suspended solids. The color was uniform and the viscosities similar to water.

Each of the samples was dried in a vacuum oven at 200° C., under full vacuum, for approximately two hours. Samples were dried independently, to allow capture of the distillate from each sample in a cold trap that was installed between the vacuum oven and the vacuum pump. After drying, the remaining net weight of each sample was recorded.

Based on the loss-in-weight, an average of 91% of each sample was evaporated. All samples dried to brittle solids that could be crushed to a powder. The dried residue from the pH 4.0 sample had a more powdery consistency than the other samples. This sample was dried for four hours, which may have resulted in removal of residual moisture that may have still been present in other dried residues. All dried residues emitted a dark, acrid vapor when they were removed from the oven. All of the dried residues were suitable for processing in a rotary flash evaporator, indicating that this equipment could be used as part of the process.

Figure 6:
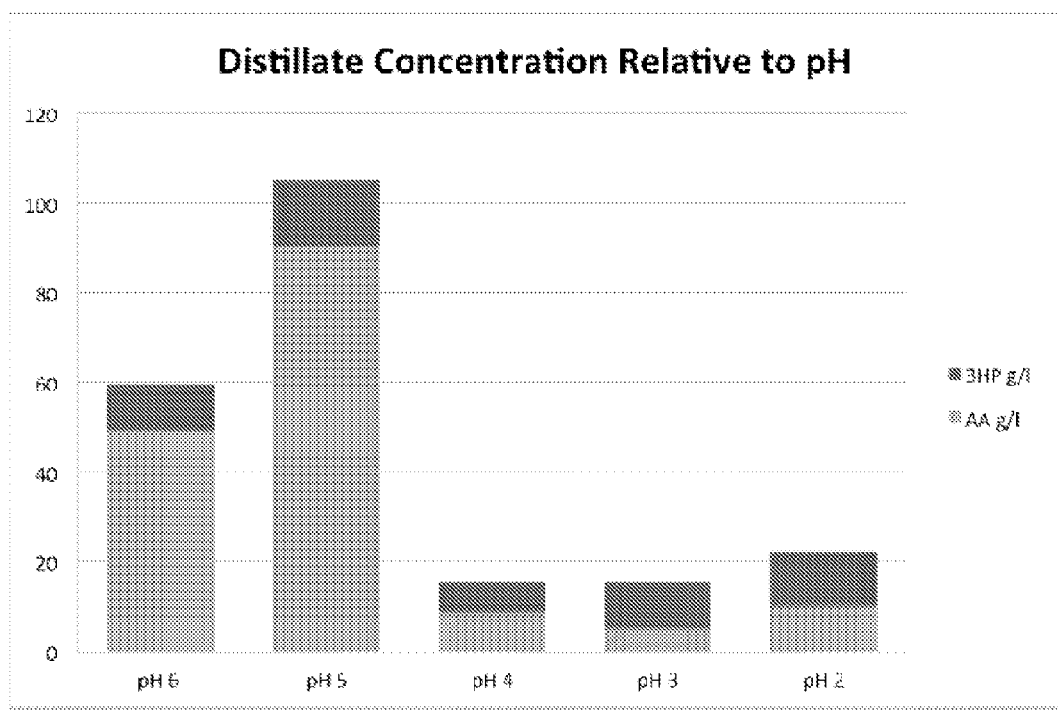
FIG. 6 shows the pH-dependence of concentration of 3-HP and AA in the distillate, as described in Example 2.

All five pH conditions resulted in the recovery of 3-HP and AA (FIG. 6). The distillates contained mostly AA, as expected for a system using a vacuum oven with a long residence time at high temperature. However, surprisingly, the greatest amount of distillate was collected from the sample adjusted to pH 5.0. The pKa of 3-HP is about 4.5, so the sample adjusted to pH 5.0 should contain 3-HP primarily in the ammonium salt form, which was not previously thought to be volatile. Nevertheless, it volatilized readily.

Figure 7:
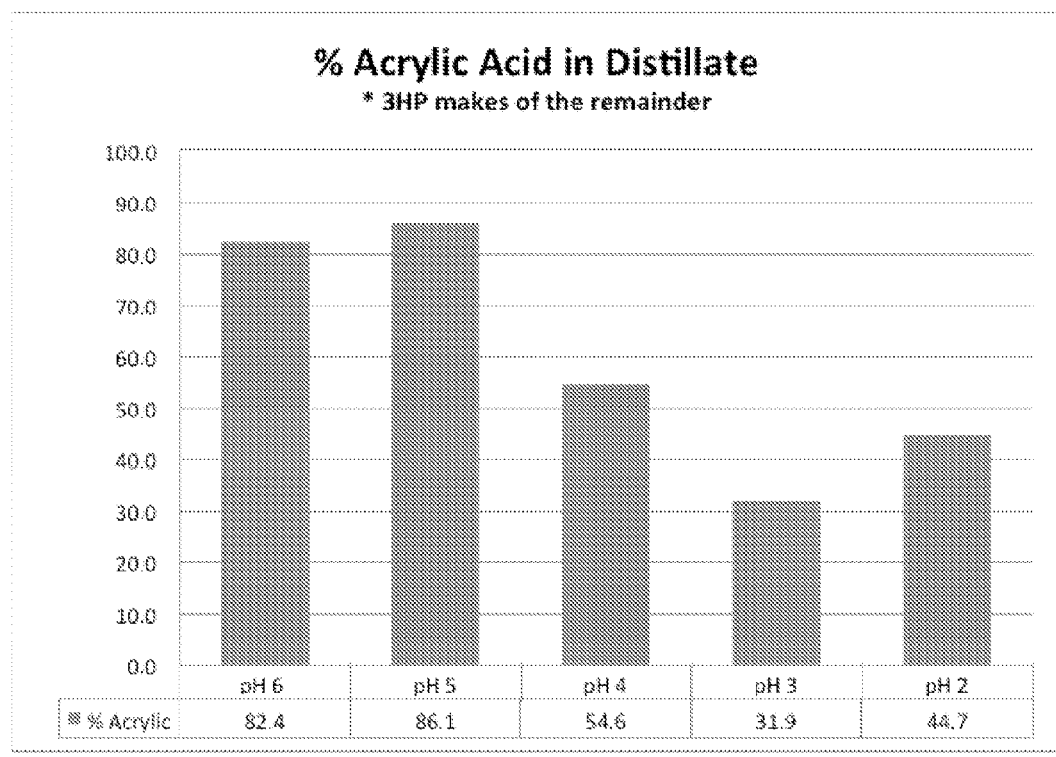
FIG. 7 shows the percent acrylic acid in distillate at different pHs, as described in Example 2.

The distillate from the pH 5.0 sample contained the highest concentrations of 3-HP and AA, at 14.6 g/l and 90.5 g/l respectively. Distillate from the pH 2.0 sample contained 12.2 g/l 3-HP and 9.9 g/l AA. Of the detectable volatile compounds, the sample at pH 5.0 resulted in the highest ratio of AA at 86%. The samples at pH 2.0 and 4.0 resulted in a nearly equal distribution of 3-HP to AA (FIG. 7).

These results indicate that the recovery of 3-HP and the dehydration of 3-HP to AA can be performed using a less acidic medium than previously considered possible. This provides several advantages, such as lower consumption of acid, less generation of ammonium sulfate waste, the ability to build processing equipment using less expensive materials, and higher recoveries of the desired product.

Example 3

Effect of pH on Evaporation of 3-HP in Short Path Rolled Film Evaporator

This experiment sought to determine the effect of pH on the evaporation of 3-HP from concentrated clarified fermentation broth using a short path rolled film evaporator. Samples of concentrate were adjusted to pH 2.5, 4.5, 6.04, or 6.5 and evaporated in a short path rolled film evaporator. Distillate was recovered and analyzed for the concentration of 3-HP, AA, and other degradation products. Surprisingly, the results showed that the distillate recovered from the medium adjusted to pH 4.5 contained the highest levels of 3-HP.

One to two liters of 3-HP in concentrate was adjusted to pH 2.5, 4.5, or 6.04, or 6.5 using sulfuric acid, followed by centrifugation (3250 G for 5 minutes) to remove solids. The pH-adjusted 3-HP concentrate was placed in the short path rolled film evaporator at a temperature of 80° C., 90° C., 100° C., 110° C., or 120° C. and a pressure of 25 mbar. The operating temperature of the evaporator used in this experiment was restricted to 120° C. Because the short path rolled film evaporator is not equipped to handle the solids that accumulate during evaporation (unlike the rotary flash evaporator, described above), glycerin was used as necessary to reduce the viscosity of the medium.

Figure 8A:
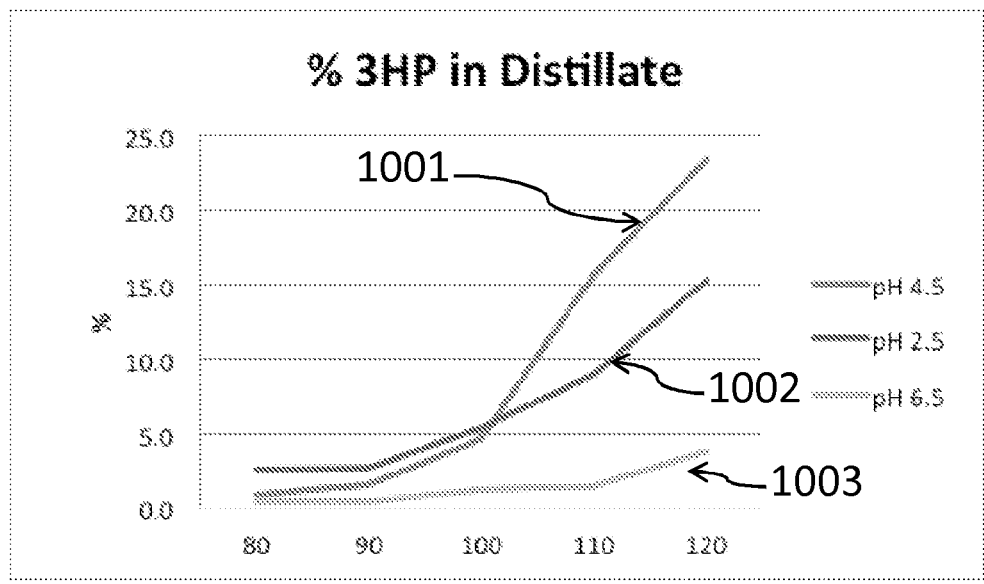
FIG. 8A shows the effect of pH on recovery of 3-HP by short path rolled film evaporation, at pHs 4.5, 2.5, and 6.5, as described in Example 3.
Figure 8B:
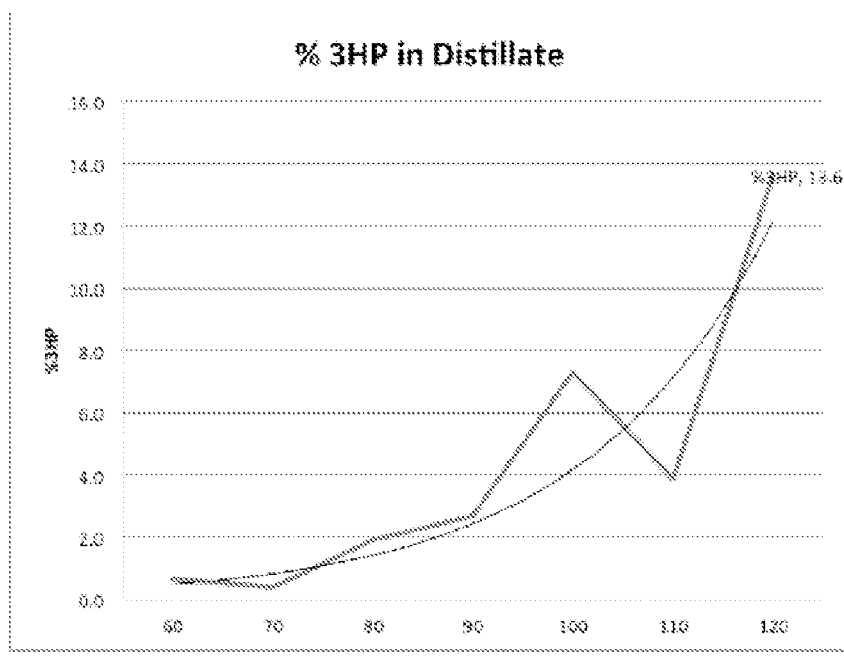
FIG. 8B shows recovery of 3-HP by short path rolled film evaporation at pH 6.04.

FIG. 8A shows that more 3-HP was recovered from the distillate of medium adjusted to pH 4.5 (1001) than from distillates of media adjusted to pH 6.5 (1003) or 2.5 (1002). The recovery of 3-HP at pH 6.04 was intermediate between the recovery at pH 2.5 and pH 6.5 (FIG. 8B).

Figure 9:
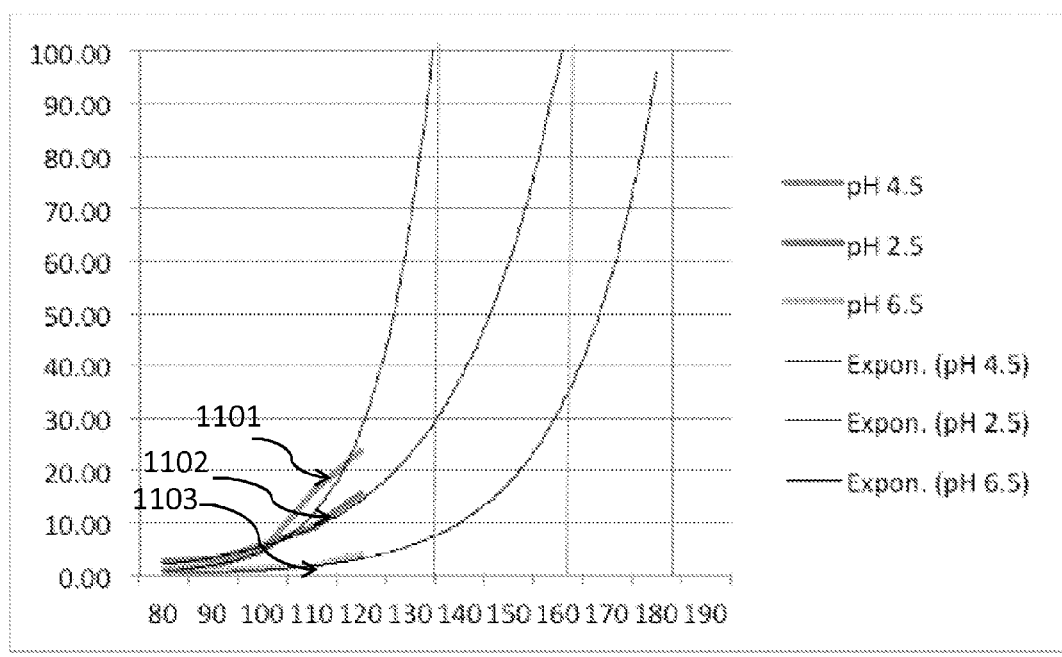
FIG. 9 shows actual and projected 3-HP recovery at three different pHs, as described in Example 3.

As expected, in view of the relatively low temperatures employed in this experiment, there was incomplete recovery of 3-HP from the medium. However, the data show an exponential increase in the amount of 3-HP recovery as the temperature is increased, indicating that a high percentage of 3-HP can likely be recovered at temperatures above about 130° C. (FIG. 9). FIG. 9 shows percent 3-HP recovery (and projected percent 3-HP recovery) for pH 4.5 (1101), pH 2.5 (1102), and pH 6.5 (1103).

Tables 1, 2, and 3 show that the vast majority of the 3-HP recovered in the distillate in the experiments described above was in the monomeric form, and that the formation of AA and other byproducts (e.g., ester dimer; ester trimer; ether dimer) was minimal. In Tables 1-3, the amount of 3-HP monomer is shown as compared to the amount of these byproducts for samples taken at various distillate temperatures. Increased AA formation is expected at higher temperatures, e.g., between 170° C. and 190° C.

TABLE 1

Percentage by weight of 3-HP monomer and byproducts in distillate at pH 2.5.

| Sample | Distillate Temp (° C.) | 3-HP Monomer | Byproducts | | | |
| --- | --- | --- | --- | --- | --- | --- |
| | | | 3-HP Ester Dimer | 3-HP Ester Trimer | 3H-P Ether Dimer | AA |
| 1 | 80 | 5.52 | 0.65 | 0.14 | | 0.05 |
| 2 | 90 | 6.43 | 0.43 | 0.11 | 0.01 | 0.05 |
| 3 | 100 | 10.73 | 0.69 | 0.18 | 0.01 | 0.05 |
| 4 | 110 | 14.82 | 0.82 | 0.20 | | 0.05 |
| 5 | 120 | 20.32 | 1.06 | 0.26 | | 0.04 |

TABLE 2

Percentage by weight of 3-HP monomer and byproducts in distillate at pH 4.5.

| Sample | Distillate Temp (° C.) | 3-HP Monomer | Byproducts | | | |
|---|---|---|---|---|---|---|
| | | | 3H-P Ester Dimer | 3-HP Ester Trimer | 3-HP Ether Dimer | AA |
| 1 | 80 | 1.49 | | | | 0.00 |
| 2 | 90 | 2.59 | | | | 0.00 |
| 3 | 100 | 5.65 | 0.03 | 0.07 | | 0.01 |
| 4 | 110 | 16.58 | 0.29 | 0.20 | 0.24 | |
| 5 | 120 | 20.34 | 0.26 | | 0.21 | |

TABLE 3

Percentage by weight of 3-HP monomer and byproducts in distillate at pH 6.04.

| Sample | Distillate Temp (° C.) | 3-HP Monomer | Byproducts | | | |
|---|---|---|---|---|---|---|
| | | | 3-HP Ester Dimer | 3-HP Ester Trimer | 3-HP Ether Dimer | AA |
| 1 | 60 | 0.65 | | | | |
| 2 | 70 | 0.4 | | | | |
| 3 | 80 | 1.93 | | | | 0.001 |
| 4 | 90 | 2.69 | | | | 0.001 |
| 5 | 100 | 7.32 | 0.04 | | 0.04 | 0.002 |
| 6 | 110 | 3.86 | | | | 0.004 |
| 7 | 120 | 13.65 | | | 0.11 | |
| 8 | Cold Trap Distillate | 23.26 | 0.14 | | 0.14 | 0.005 |

Example 4

Effectiveness of Flash Evaporation to Purify 3-HP

Table 4 summarizes the experimental design for an experiment designed to illustrate that 3-HP can be purified by flash evaporation using a rotary evaporator and result in minimal conversion of 3-HP to byproducts such as AA. Four batches of 3-HP fermentation broth were combined to form a 3-HP feedstock that was approximately 30 weight percent 3-HP. The feedstock was divided into five runs and the feedstock pH was adjusted for each run as indicated in Table 4. As also indicated in Table 4 all other process parameters were essentially the same for each run except for the flash evaporation temperature (i.e., the second vessel temperature).

TABLE 4

Conditions for Pilot Plant Test

| | Run 1 | Run 2 | Run 3 | Run 4 | Run 5 |
|---|---|---|---|---|---|
| Batches 7,14,15,16 | ———————————→ | | | | |
| 3-HP Conc. | ~30 wt. % ———————————→ | | | | |
| pH | 6.5 | 4.5 | 4.5-2.5 | 2.5 | 0.6 |
| Flash Temp Range (° C.) | 120-240 | 120-220 | ———————→ | | |
| Feed Rate | 0.1-0.3 gpm ———————————→ | | | | |
| Vacuum | <100 mbar ———————————→ | | | | |
| RPM | 1200 ———————————→ | | | | |
| Pre-Heat Temp* (° C.) | 80 ———————————→ | | | | |
| Chiller 1 Temp (° C.) | 15 ———————————→ | | | | |
| Chiller 2 Temp (° C.) | -40 ———————————→ | | | | |
| Skin Temp** (° C.) | 120 | 180 | 200 | 220 | 240 |

*First vessel temperature
**Inlet process heating oil temperature (i.e., second vessel temperature)

Figure 10:
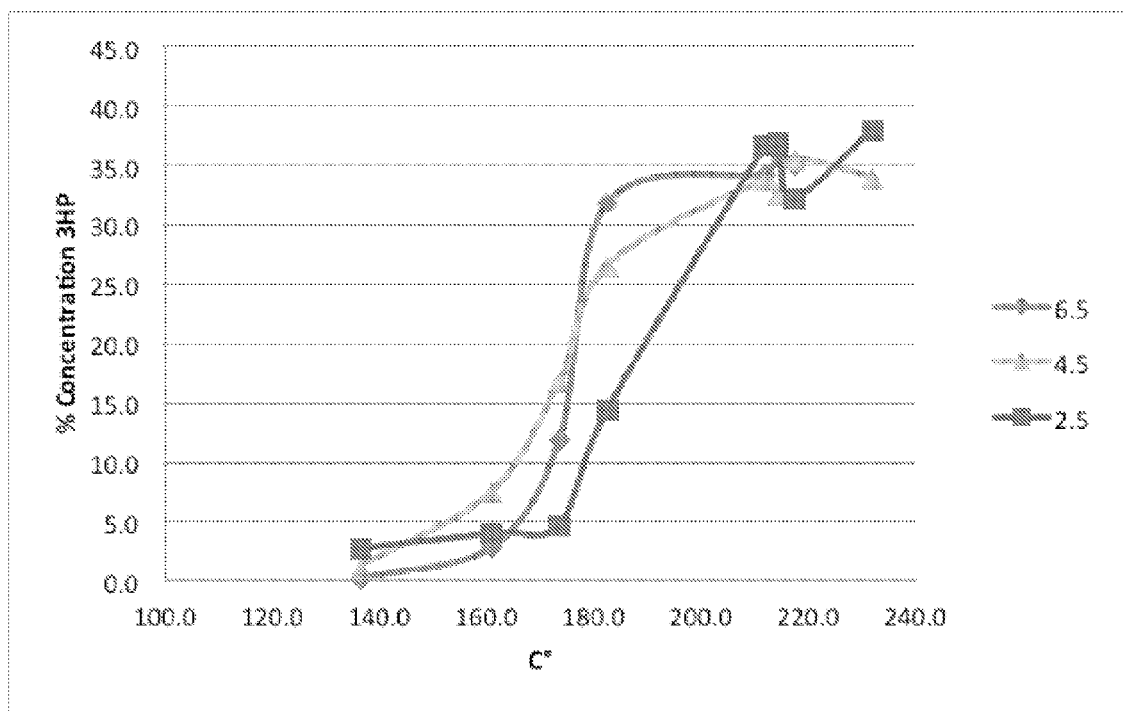
FIG. 10 shows the concentration of 3-HP in distillate by weight at three different pHs, as described in Example 4.

The results of this experiment are shown in FIGS. 10-20. FIG. 10 shows the concentration of 3-HP in distillate by weight at three different pHs. At all three pHs, 3-HP was purified by flash evaporation and then condensed at about 16° C. to a purified liquid state. The maximum concentration of 3-HP in the distillate in all three cases occurred at temperatures above 200° C. At lower temperatures, for example, 140° to 170° C., the most concentrated samples occurred at pH 4.5. At 180° C., samples from the pH 6.5 feed resulted in the highest 3-HP concentration. The sharpest inflection point in 3-HP volatility occurred between about 173° C. and 182° C. at pH 6.5.

Figure 11:
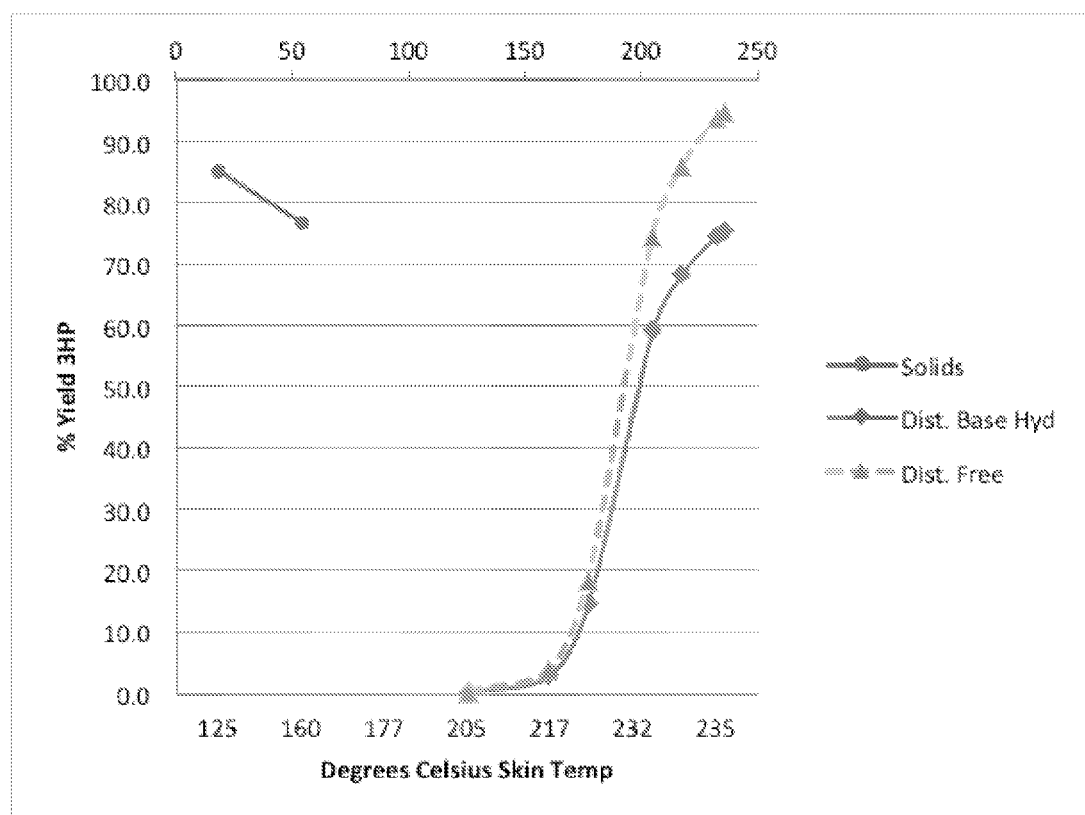
FIG. 11 shows the percent yield of 3-HP in distillate from a pH 6.5 feed at different second vessel temperatures, as described in Example 4.

FIG. 11 shows the percent yield of 3-HP in distillate from a pH 6.5 feed at different skin temperatures (i.e., second vessel temperatures). The dotted line represents the percent recovery of 3-HP based on the assay of monomeric 3-HP available in the starting feed. Oligomers of 3-HP are not volatile and not taken into account when calculating this curve. The yield of 3-HP was less than 5% at or below 205° C. and the distillate samples collected were basic (pH 11-pH 10), which indicated free ammonia was volatilized in this range. At temperatures above 217° C. an exponential increase in 3-HP volatility was observed with a maximum percent recovery of about 95% monomeric 3-HP occurring at about 235° C. The calculated recovery was reduced to about 76% when a base hydrolysis of the starting material was performed ("Dist. Base Hyd"). This procedure liberated monomeric 3-HP from oligomeric 3-HP, effectively increasing the starting 3-HP concentration. It was assumed that the 3-HP starting titers in this analysis were partially unavailable in a distillation process because they were in a non-volatile form.

Figure 12:
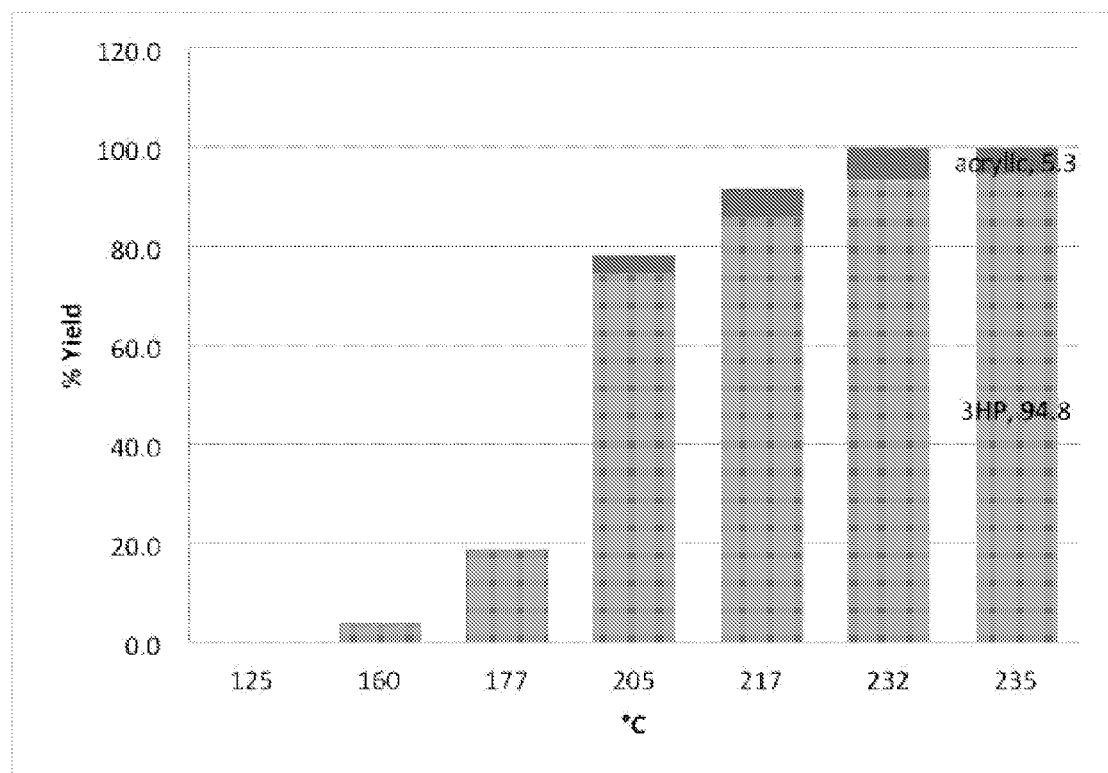
FIG. 12 shows that at or above 232° C., nearly 100% percent of monomeric 3-HP was recovered in the distillate from pH 6.5 feed, in the forms of 3-HP or acrylic acid, as described in Example 4.

FIG. 12 shows that at or above 232° C., nearly 100% percent of monomeric 3-HP was recovered in the distillate from pH 6.5 feed, in the forms of 3-HP or acrylic acid. For example, at 235° C., the total recovery is about 99.8% with 94.8% 3-HP and 5.3% AA.

Figure 13:
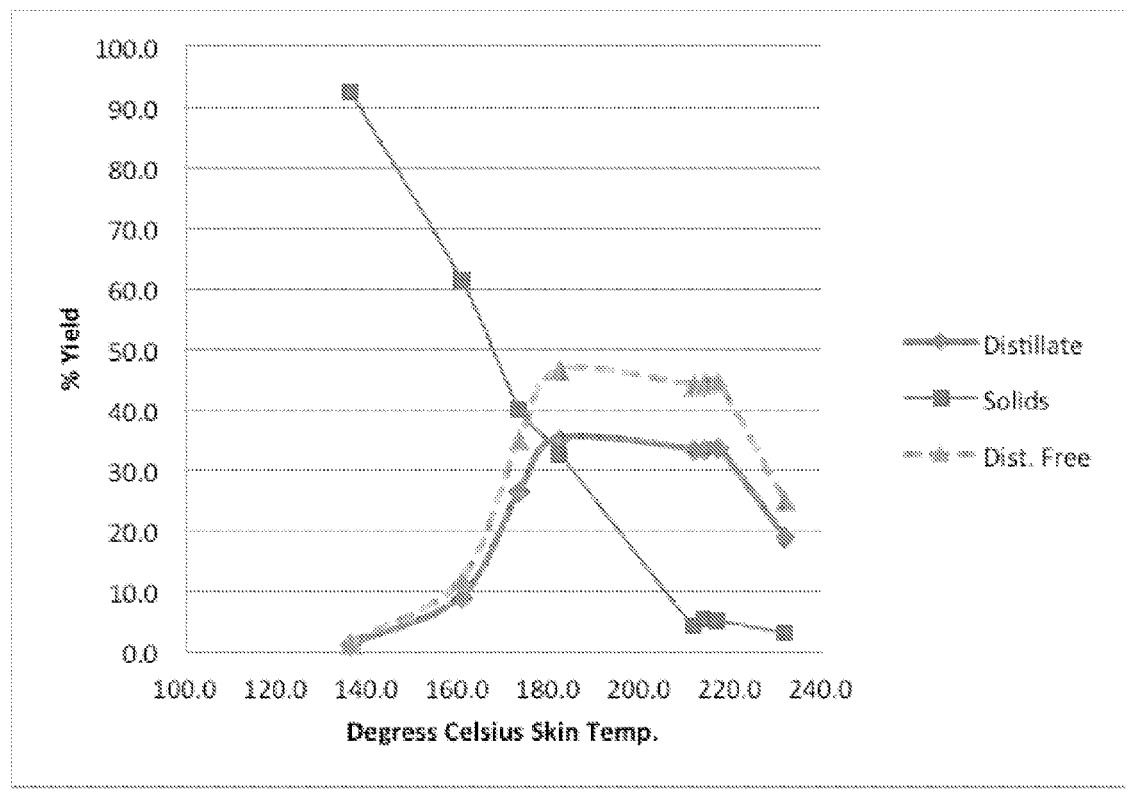
FIG. 13 shows the percent yield of 3-HP in distillate from a pH 4.5 feed at different skin temperatures (i.e., second vessel temperatures), as described in Example 4.

FIG. 13 shows the percent yield of 3-HP in distillate from a pH 4.5 feed at different skin temperatures (i.e., second vessel temperatures). At pH 4.5, 3-HP began to volatilize at nearly about 20° C. lower temperature than other pH conditions, such as pH 6.5 and 2.5. This trend unexpectedly changed above 180° C. where 3-HP in the distillate plateaus at a maximum of about 47% recovery of monomeric 3-HP. As temperature increased the percent of recovery decreased. This suggests that 3-HP was probably oligomerizing under these conditions and was no longer available in a volatile form. Further evidence supporting this was that the trend lines in the solids and distillate rates contradict the expected trends. In the case of the solids mass balance, nearly as much weight was recovered at 136° C. as at 232° C. Given the volatility of water alone leaving the system, material from previous conditions may be accumulating and extruding during the high temperature collection times. The pH of the distillate varied from acidic to basic back to acidic as temperature increased. Again this suggests a reaction is taking place, potentially with ammonia itself. The pKa of 3-HP is about 4.5. Without being bound by theory, it is possible that the increased volatility of 3-HP under these conditions may be due to an equilibrium of the acidic form of 3-HP converting to the gas phase. As the acid leaves, the equilibrium is shifted away from the ammonium salt back to the acid which is again volatilized. Strong acids, such as sulfuric acid, may potentially have a negative effect due to the ability of the acid to complex with water and potentially 3-HP. This could suppress the vapor pressure of 3-HP even though it is fully protonated. At temperatures above 210° C., less than 5% of the 3-HP is detected in the solids. Roughly half of the 3-HP is reacted at higher temperatures at this pH. Although this may be a relatively poor condition for 3-HP recovery, it may be favorable conditions for polymerization.

Figure 14:
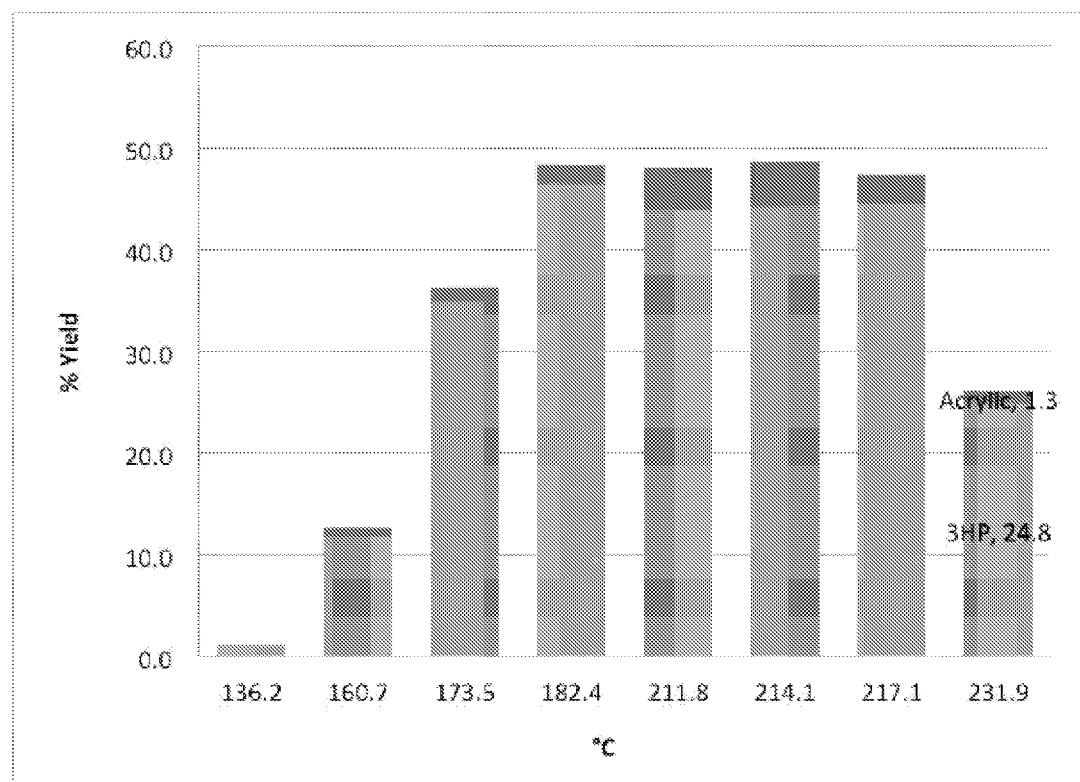
FIG. 14 shows the yields of 3-HP and AA in distillate from a pH 4.5 feed at different second vessel temperatures, as described in Example 4.

FIG. 14 shows the yields of 3-HP and AA in distillate from a pH 4.5 feed at different second vessel temperatures. The maximum recovery of monomeric 3-HP (almost 50%) in the forms of 3-HP and AA was achieved in a temperature range of about 180 to about 217° C. At a higher temperature (e.g., about 232° C.), the percent of recovery dropped significantly.

Figure 15:
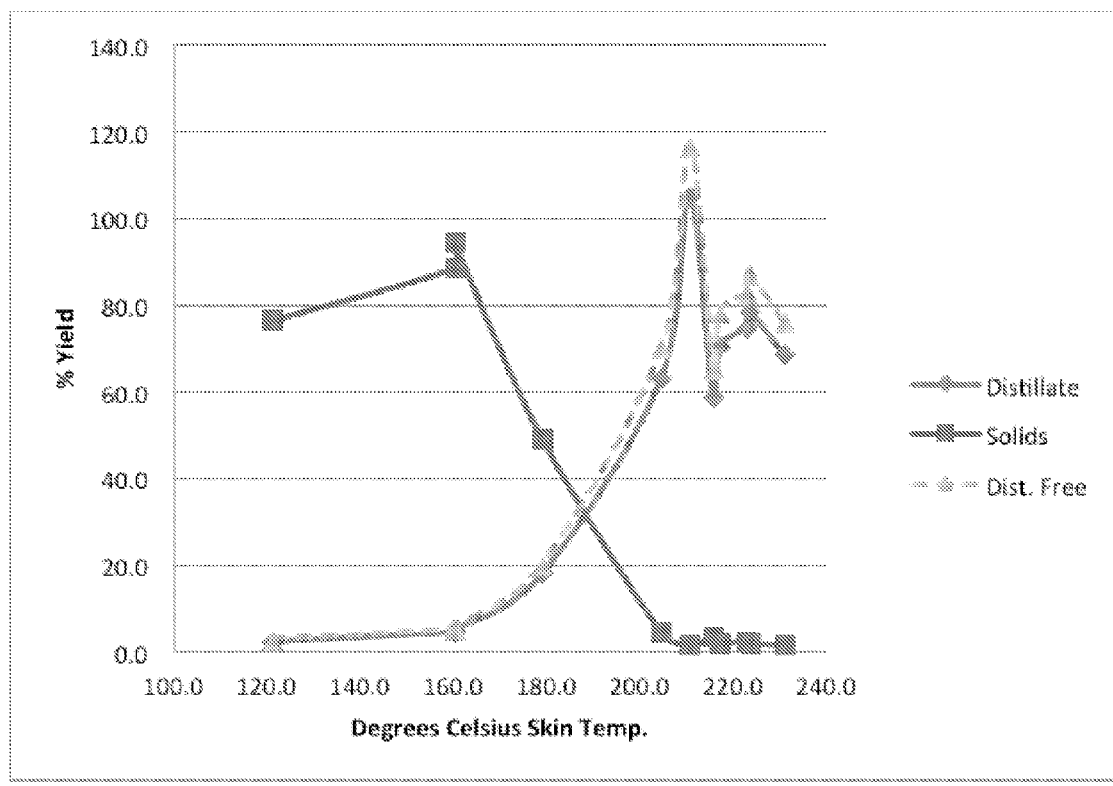
FIG. 15 shows the yield of 3-HP from a pH 2.5 feed at different skin temperatures, as described in Example 4.
Figure 16:
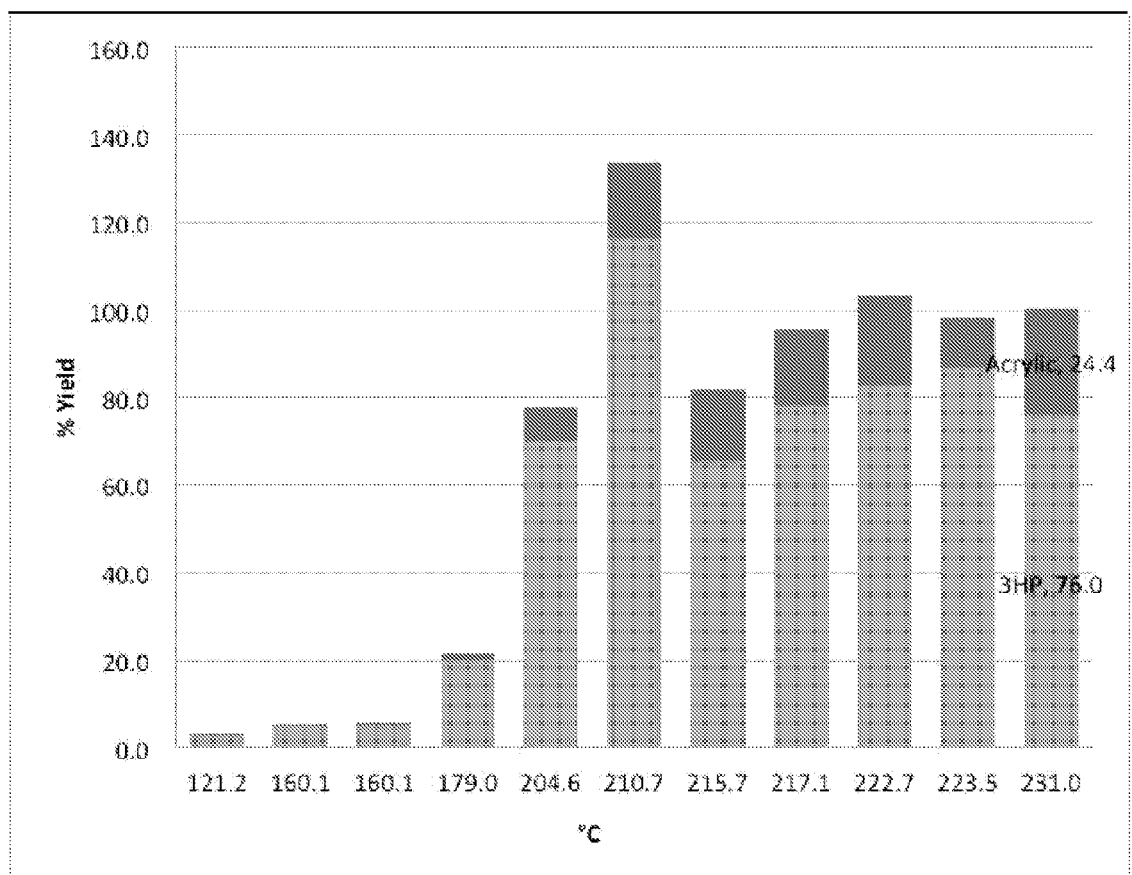
FIG. 16 shows yields of 3-HP and AA in distillate from a pH 2.5 feed, as described in Example 4.

FIG. 15 shows the yield of 3-HP from a pH 2.5 feed at different skin temperatures. The volatility of 3-HP at pH 2.5 was similar to the trends observed at pH 6.5, with the biggest exception being the pH of the distillate. At pH 2.5, ammonium ions are paired with the sulfate from the sulfuric acid to form ammonium sulfate. The ammonium sulfate is not readily converted to free ammonia and any volatile acids would contribute to the low pH of the distillate. It appeared that the protonated form of 3-HP volatilized the same way under both high pH (pH 6.5) and low pH (pH 2.5) conditions which further strengthened the supposition that the acid form of 3-HP exists at pH 6.5 (FIG. 16).

Figure 17:
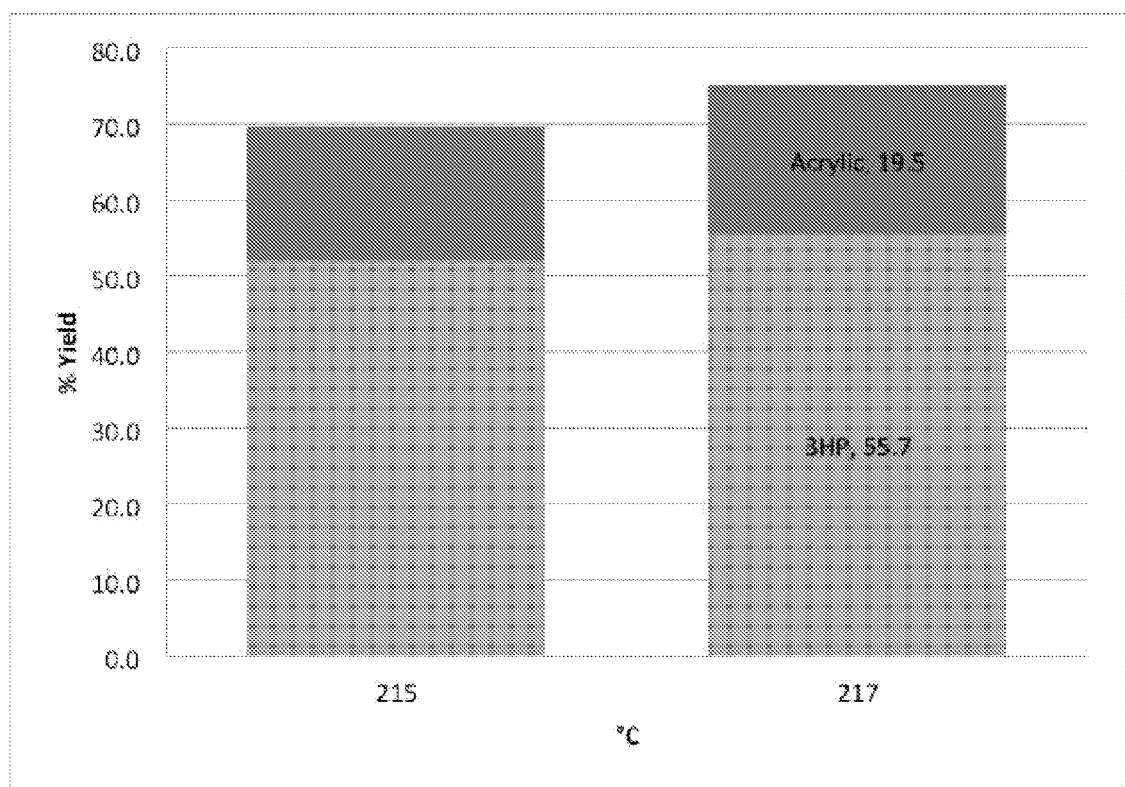
FIG. 17 shows yields of 3-HP and AA in distillate from a pH 0.6 feed, as described in Example 4.

At pH 2.5, 3-HP mass balance was at about 100% in the temperature range of about 222 to about 231° C. The highest percentage conversion to acrylic acid was about 24.4% at about 231° C. (FIG. 16). These conditions exceeded the percent of 3-HP converted to acrylic acid at pH 0.6 (FIG. 17). The highest conversion of 3-HP to AA observed at pH 0.6 was 19.5%. Because nearly 25% of the 3-HP was unaccounted for, it was assumed that pH 0.6 conditions again favored oligomer formation.

Figure 18:
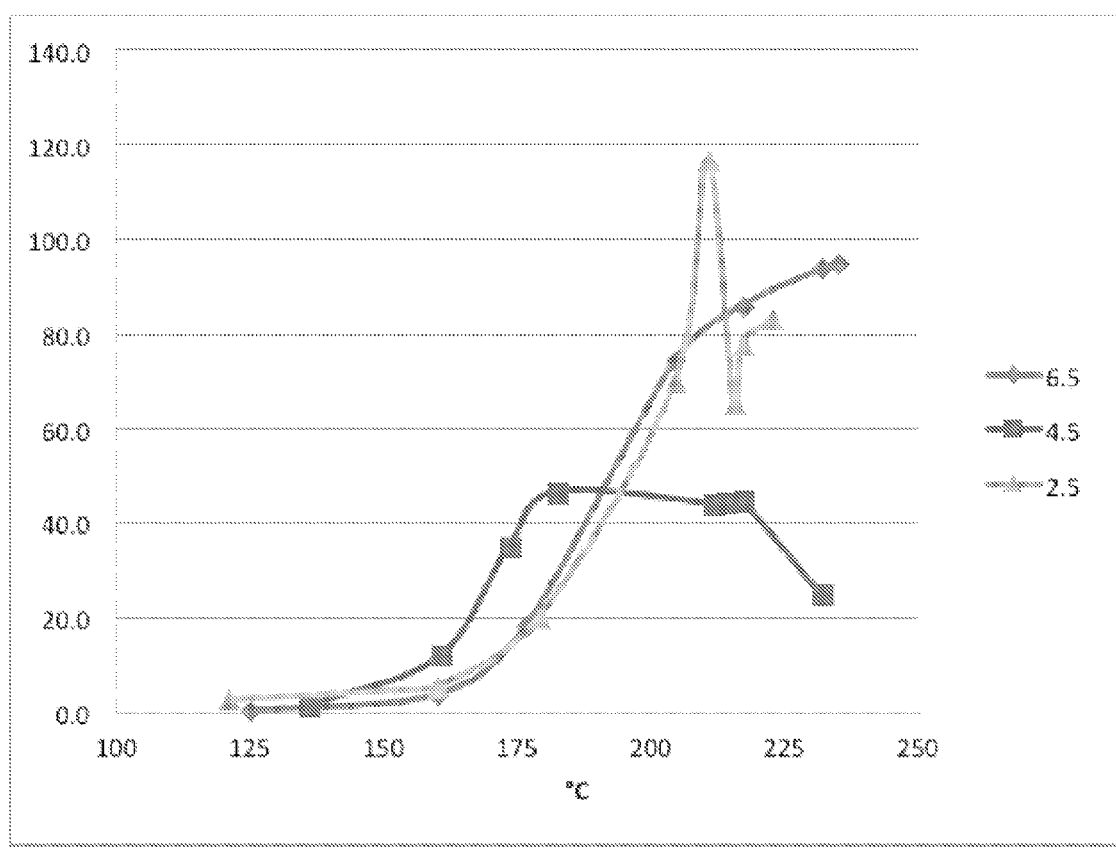
FIG. 18 shows a comparison of percent yield of 3-HP by weight in distillate at different pHs, as described in Example 4.
Figure 19:
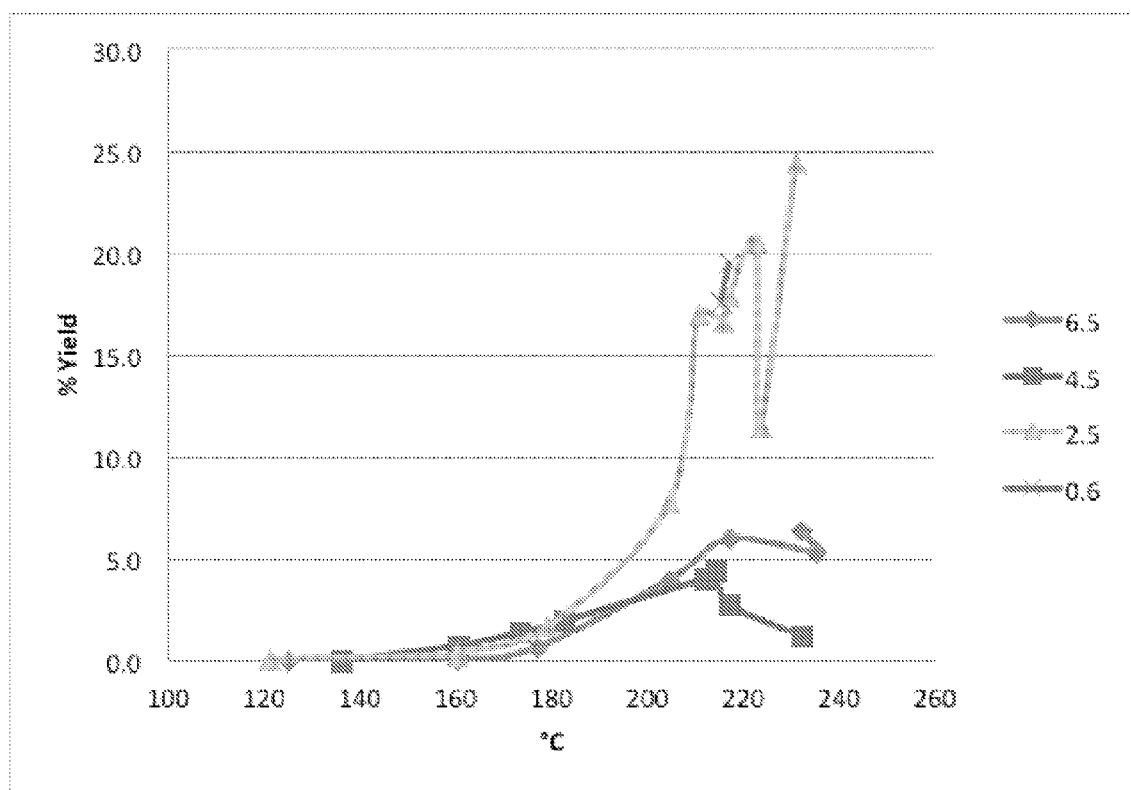
FIG. 19 shows a comparison of percent of 3-HP converted to acrylic acid in distillate on a molar basis at different pHs, as described in Example 4.
Figure 20:
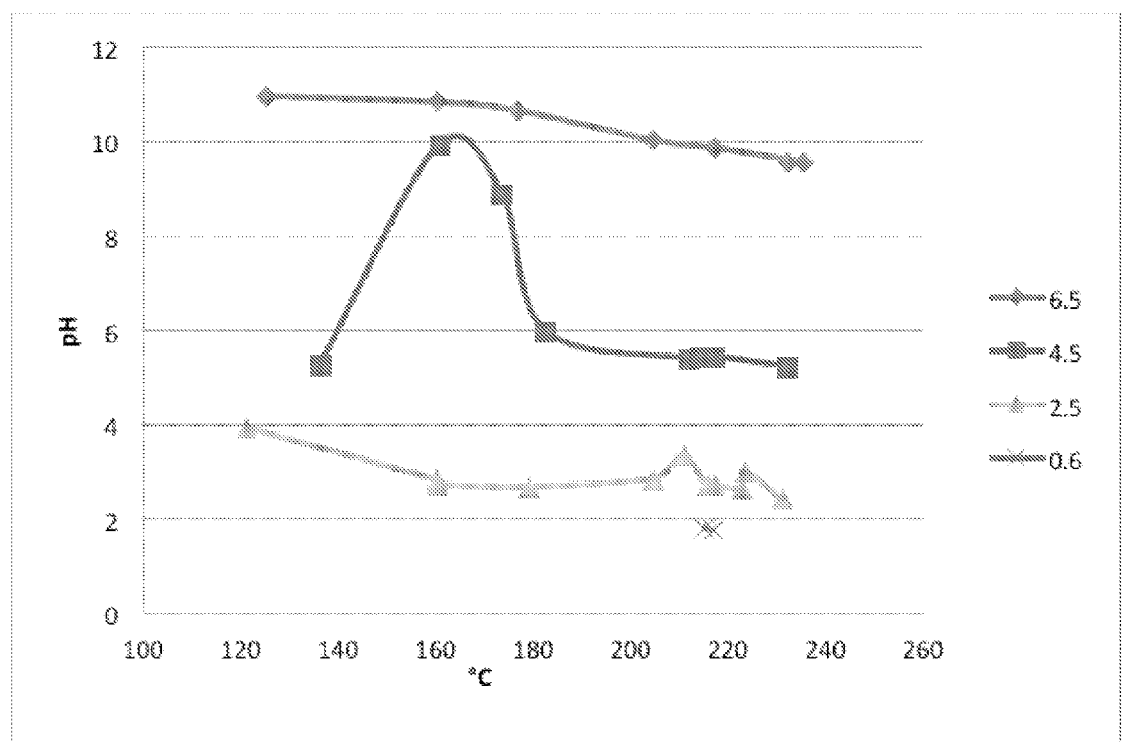
FIG. 20 shows a comparison of pH of the distillates at different pHs, as described in Example 4.

FIGS. 18-20 show a comparison of percent yield of 3-HP by weight in distillate (FIG. 18), percent of 3-HP converted to acrylic acid in distillate on a molar basis (FIG. 19), and pH of the distillates (FIG. 20) from feeds at pHs 2.5, 4.5, and 6.5.

Example 5

Thermal Salt Splitting and 3-HP Vaporization in a Rolled Film Evaporator (RFE)

In some cases, 3-HP may be recovered by thermal salt splitting and 3-HP vaporization in a rolled film evaporator. An exemplary system is depicted in FIG. 21.

Clarified fermentation broth was pre-concentrated using a rotary evaporator to a 3HP concentration of 46-52 wt % by removing water. Before the pre-concentration step in the rotary evaporator, the pH of the fermentation broth was near neutral at 7. The pH of the concentrated clarified fermentation broth was 5.2 after the pre-concentration step. During the pre-concentration step, the rotary evaporator temperature was maintained at a temperature 60° C. and a pressure 15-60 mbar. Under these conditions, at least 20% of the ammonium 3HP salt was split to produce a mixture of protonated 3-HP and residual ammonium 3HP salt. However, the salt splitting could not be improved beyond 20-22% in the rotary evaporator even after extending the run longer under these conditions. The ammonium ion removal yield was quantified using the colorimetry method. The colorimetry method measured the concentration of ammonium ion in the aqueous mixture. This pre-concentrated broth was then fed to the flash vaporizer, the rolled film evaporator, to carry out the thermal salt splitting of residual ammonium 3HP salt and simultaneous vaporization and purification of protonated 3HP, ammonia and water.

The flash vaporizer was operated at three different temperatures (120° C., 170° C. and 220° C.) to determine the impact of temperatures on thermal salt splitting yield and 3-HP vaporization in the overhead. The pressure was atmospheric in all runs. With reference to FIG. 21, the internal condenser, 14, temperature was maintained at 15° C.

Figure 21:
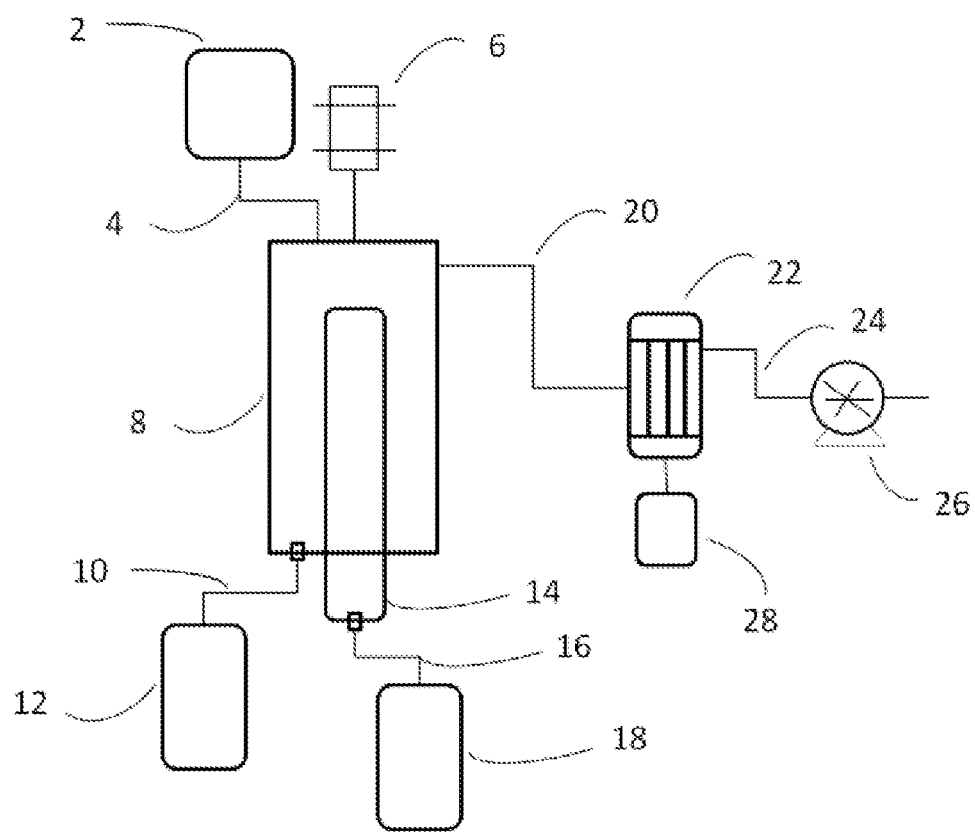
FIG. 21 shows an exemplary system for thermal salt splitting and 3-HP vaporization in a rolled film evaporator (RFE). The system comprises a first vessel 2 which acts as a feed tank, a second vessel 8 that is a rolled film or wiped-film evaporator, a third vessel 12 acts as residue collection tank, a fourth vessel 18 acts as distillate collection tank, a fifth vessel 22 acts as cold trap, a sixth vessel 28 acts as cold trap collection pot and 26 is an optional vacuum pump. Feed vessel 2 is configured to receive an aqueous feed of a composition comprising a mixture of ammonium salt of 3-HP and protonated 3-HP. The aqueous feed is a fermentation broth. The aqueous 3-HP in vessel 2 is maintained at a first temperature under atmospheric pressure. The aqueous feed from vessel 2 is fed to the second vessel 8, a flash vaporizer (rolled film evaporator), maintained at a second temperature and pressure. The feed line 4 is pre-heated. The flash vaporizer comprises an internal condenser 14 that is configured to condense 3HP vapor. During operation, the condensate from the internal condenser 14 is collected in the condensate collection pot 18. The residue from the flash vaporizer is collected in the residue collection pot 12. The vent from the flash vaporizer goes to the cold trap 22 and finally to the vacuum pump 26.

With continued reference to FIG. 21, three hundred grams of pre-concentrated fermentation broth was fed to the feed vessel 2. The pre-concentrated material was highly viscous. In order to keep the material flowable from the feed tank 2 to the flash vaporizer 8, the feed tank and transfer line 4 were kept at a temperature of 60° C. The flash vaporizer roller speed was kept constant at 270 rpm. The feed flow rate was varied from 6 g/min to 18 g/min. The average residence time was 160 at 6 g/min and 45 s at 18 g/min. The flash vaporizer surface area was 0.06 m$^2$ which gave a flux of 1 kg/m$^2$-hr at 1 g/min feed rate.

The salt splitting yield % was calculated as, $$\% \text{ Salt split} = \frac{\text{Wt of residue} * [\text{NH4+}]}{\text{Wt of feed} * [\text{NH4+}]} * 100\%$$

The [NH4+] concentration in the feed and in the residue was measured by the colorimetry method.

Table 5 summarizes the experimental results. No thermal salt splitting was observed at 120° C. The thermal salt splitting (TSS) yield improved to 86.5% at 220° C. for a flow rate of 6 g/min. However, the TSS yield decreased to 49.2% when the flow rate was increased to 18 g/min. The reduced thermal salt splitting yield at the higher flow rate was attributed to the shorter residence time of the material in the flash vaporizer.

The 3-HP boiling point is 217° C. at atmospheric pressure. Although the feed contained some amount of protonated acid, no 3-HP was observed in the overheads at 120° C. Hence, no thermal salt splitting was observed 120° C.

However, when the flash vaporizer skin temperature was increased to 220° C., 62.1% 3-HP equivalent in the feed was recovered in the distillate at 6 g/min feed flow rate. When the feed flow rate was increased to 18 g/min, a smaller amount of 3-HP equivalent in the feed was recovered in the distillate. With reference to FIG. 21, these experiments clearly demonstrated that at higher salt splitting yield, an increased amount of protonated 3-HP was vaporized and condensed in the internal condenser 14 and was collected in distillate collection pot 18. Moreover, the flash vaporizer skin temperature at of 220° C. was marginally above the boiling point of 3HP under atmospheric pressure (3-HP boiling point 217 C). The high skin temperature of the flash vaporizer was therefore expected to enhance the salt splitting yield and vaporization of 3HP.

Some 3-HP dehydration to acrylic acid was observed at a flash vaporizer skin temperature of 220° C. Based on the evaporated equivalents, around 14 to 24 mol. % of 3-HP equivalents collected in the distillate was acrylic acid. This corresponded to 7 to 10 wt % of the initial 3-HP present in the feed dehydrated to acrylic acid.

The pH of the distillate was 9 to 10. Therefore, the protonated 3-HP from the flash vaporizer recombined with ammonia during the condensation on the internal condenser surface at 15° C.

TABLE 5

Summary of flash vaporization results in a rolled film evaporator

| RFE skin temperature & flow rate | Salt splitting yield % | 3 HP (monomer) conc. wt % in the residue | Ester dimer wt % in the residue | % of 3 HP equiv. in the feed recovered in the distillate | % 3 HP accountability |
|---|---|---|---|---|---|
| Feed concentration: 3-HP monomer 56 wt % | | | | | |
| 120 C. & 6 g/min | 0.0 | 62.3 | 1.2 | 0.0 | 111.4 |
| 120 C. & 18 g/min | 0.0 | 60.9 | 1.2 | 0.0 | 108.8 |
| 220 C. & 6 g/min | 86.5 | 66.3 | 9.6 | 62.1 | 97.5 |
| 220 C. & 18 g/min | 49.2 | 62.8 | 6.5 | 31.7 | 81.5 |

The residue was highly viscous and it was difficult to obtain homogeneous sample analysis. As a result, the mass balance did not fully close for some of the experiments.

Example 6

Thermal Salt Splitting of Ammonium 3-HP and 3-HP Purification from Water and Ammonia Using a Partial Condenser In some cases, 3-HP may be recovered by thermal salt splitting of ammonium 3-HP and 3-HP purification from water and ammonia using a partial condenser. An exemplary system is depicted in FIG. 22.

Clarified fermentation broth was pre-concentrated using a rotary evaporator to remove water to achieve a 3HP concentration of 42-55 wt %. Before the pre-concentration step in the rotary evaporator, the fermentation broth pH was about 7. The concentrated clarified fermentation broth pH was 5.2. During pre-concentration, the rotary evaporator temperature was maintained at 60° C. and 15-60 mbar. Under these conditions, at least 20% of the ammonium 3HP salt was split to produce a mixture of protonated 3HP and residual ammonium 3HP salt. This pre-concentrated broth was then fed to the flash vaporizer, the rolled film evaporator, to carry out the thermal salt splitting of residual ammonium 3HP and simultaneous vaporization and purification of protonated 3HP, ammonia, and water.

The flash vaporizer was operated at a constant skin temperature of 195° C. The pressure was maintained at 70-80 mbar. The first overhead partial condenser was operated at a temperatures from 110 to 130° C. to determine the effect on 3HP recovery efficiency and the extent of recombination between the ammonia and 3-HP. The second overhead condenser 24 was operated at 5° C. to condense the remaining volatiles leaving the first condenser such as propionic acid, acetic acid, water and ammonia.

Figure 22:
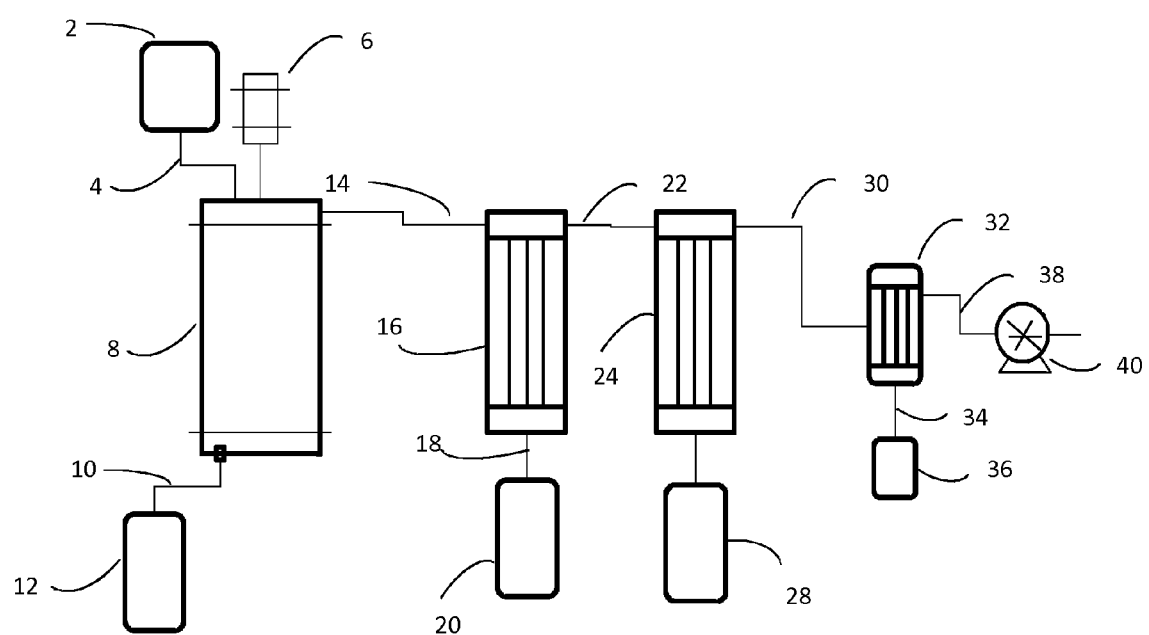
FIG. 22 shows an exemplary system for thermal splitting of ammonium 3-HP and 3-HP purification from water and ammonia using a partial condenser. The system comprises a first vessel 2 which acts as a feed tank, a second vessel 8 that is a rolled-film or wiped-film evaporator, a third vessel 12 acts as residue collection tank, a fourth vessel 16 acts as the first overhead condenser, a fifth vessel 20 acts as first overhead condenser condensate collection tank, a sixth vessel 24 acts as the second overhead condenser, a seventh vessel 28 acts as the second overhead condenser condensate collection tank, an eighth vessel 32 acts as cold trap, a ninth vessel 36 acts as cold trap collection pot and 40 is a vacuum pump. Feed vessel 2 is configured to receive an aqueous feed of composition comprising a mixture of ammonium salt of 3-HP and protonated 3-HP. The aqueous feed is a fermentation broth. The aqueous 3-HP in vessel 2 is maintained at a first temperature under atmospheric pressure. The aqueous feed from vessel 2 is fed to the second vessel 8, a flash vaporizer (rolled-film or wiped-film evaporator), maintained at the second temperature and pressure. The feed line 4 is pre-heated to a temperature that facilitates the pumping of the feed. The flash vaporizer is attached to a first overhead condenser 16 that is configured to condense at least a portion of the 3HP vapor from the second vessel. The first overhead condenser is operated at a higher temperature than the second condenser (from 80-140 C) to act as a partial condenser to preferentially condense the 3-HP vapor and to allow the major portion of water vapor and ammonia to leave the first condenser. The first overhead condenser is set at a temperature which is low enough to condense the 3HP vapor and at the same time sufficiently high to minimize the condensation of absorption of ammonia that leads to the recombination of ammonia and 3HP to reform ammonium 3-HP. The vent gas from the first condenser is passed through a second condenser 24 to condense all the volatiles leaving the first condenser. The second condenser is operated at room temperature or below to condense all the volatiles. The vent from the second condenser goes to a cold trap 32 to condense all residual vapors prevent them from reaching the vacuum pump. The system is operated below atmospheric pressure by using the vacuum pump 40.

With reference to FIG. 22, around 600-700 g of pre-concentrated fermentation broth was fed to feed vessel 2. The pre-concentrated material was highly viscous. In order to keep the material flowable from the feed tank 2 to the flash vaporizer 8, the feed tank and the transfer line 4 were kept at a temperature between 70-60° C. The flash vaporizer roller speed was 300 rpm. The feed flow rate was 18 g/min.

Table 6 summarizes the results. In Run A1 and A2 the first overhead condenser coolant temperature was 130° C. The 3-HP concentrations in the feed (as a mixture of ammonium salt and protonated 3-HP) were 46.6 and 45.5 wt % and the corresponding water concentrations were 7.7 wt % and 11.0 wt % respectively. The recovery of 3-HP in 1st condenser relative to the total 3-HP equivalent collected in the first and the second condenser was 63-66%. The molar ratio of ammonia to 3-HP was a measure of the extent of recombination between ammonia and protonated 3-HP in the first overhead condenser. When the pH was neutral, this ratio was 1. With increasing salt splitting yield, this ratio decreased with continuous removal of ammonia from the salt. A ratio of 0.38-0.42 indicated about 60% of the 3-HP present in the protonated form with the remainder as ammonium salt. In the second set of experiments, the second overhead condenser was operated at 110° C. The 3-HP concentrations in the feed (as a mixture of ammonium salt and protonated 3-HP) were 42 and 46.3 wt %, and the corresponding water concentrations were 9.4 wt % and 9.2 wt % respectively. The recovery of 3-HP relative to the combined total 3-HP equivalent collected in the first and the second condenser increased to 73-80% in the first condenser when it was operated at 110° C. compared with the 63-66% 3-HP recovered in the first condenser when operated at 130° C. However, the molar ratio of ammonia to 3-HP increased to 0.48-0.52 indicating a 50:50 ratio of 3-HP present in the protonated and in the salt form.

3-HP dehydration to acrylic acid was observed in all runs. The dehydration yield was between 7-11% of the initial amount of 3-HP fed to the flash vaporizer. Acrylic acid was only collected in the second overhead condenser flask as the temperature in the first overhead condenser (either 110 or 130° C.) was higher than the boiling point of Acrylic acid at the system pressure.

The pH of the first condensate varied between 4.2 to 4.6 depending on the condenser temperature and the extent of recombination between ammonia and 3-HP. The pH of the second condensate was 10 to 11.

TABLE 6

Results from experiment described above.

|  | Run-A1 | Run-A2 | Run-B1 | Run B2 |
|---|---|---|---|---|
| Flow rate (g/min) | 18 | 18 | 18 | 18 |
| Skin temp. C. | 195 C. | 195 C. | 195 C. | 195 C. |
| First overhead condenser Temp C. | 130 C. | 130 C. | 110 C. | 110 C. |
| 3-HP wt % in the feed | 46.6% | 45.5% | 42.0% | 46.3% |
| Water wt % in the feed | 7.70% | 11.0% | 9.40% | 9.20% |
| Total (residue + all condensates) 3 HP recovered | 81.0% | 92% | 62% | 96% |
| % recovery of 3 HP in 1st cond. relative to the total 3 HP collected in 1st and 2nd cond | 65.4% | 63% | 73% | 80% |
| AA yield | 7.1% | 10% | 13% | 11% |
| mols of ammonia/mols of 3-HP from the first overhead condenser | 0.42 | 0.38 | 0.48 | 0.52 |

The residue was highly viscous and it was difficult to obtain homogeneous sample analysis. As a result, the mass balance did not fully close for some of the experiments.

Other Embodiments

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising nonaqueous components that are at least about 90% by weight of a biologically produced 3-HP, wherein said 3-HP has a $^{14}C$ concentration of at least 1 part per trillion carbon and wherein said composition consists essentially of about 1 to about 60% water by weight and about 40% to about 99% nonaqueous components.

2. The composition of claim 1, wherein said 3-HP has a $^{14}C$ concentration of about 1.2 parts per trillion carbon.

3. The composition of claim 1, wherein said nonaqueous components comprise at least about 95% by weight of said biologically produced 3-HP.

4. The composition of claim 1, wherein said nonaqueous components comprise at least about 98% by weight of said biologically produced 3-HP.

5. The composition of claim 1, wherein said composition comprises less than about 30% water by weight.

6. The composition of claim 1, wherein said composition comprises less than about 10% by weight of acrylic acid.

7. The composition of claim 1, wherein said composition comprises less than about 5% by weight of acrylic acid.

8. The composition of claim 1, wherein said composition comprises less than about 1% by weight of acrylic acid.

9. A downstream chemical product produced from the composition of claim 1, wherein said downstream chemical product is selected from the group consisting of acrylic acid (AA), 1,3-propanediol, methyl acrylate, acrylamide, propiolactone, ethyl-3-3-HP, malonic acid, acrylonitrile, butyl acrylate, 3-HP amide, and ethyl acrylate.

10. A consumer product produced using the downstream chemical product of claim 9.

11. The consumer product of claim 10, wherein said consumer product comprises a downstream chemical product with a $^{14}C$ concentration of at least 1 part per trillion carbon.

* * * * *